US009738712B2

(12) United States Patent
Lafaye et al.

(10) Patent No.: US 9,738,712 B2
(45) Date of Patent: Aug. 22, 2017

(54) CAMELID SINGLE-DOMAIN ANTIBODY DIRECTED AGAINST AMYLOID BETA AND METHODS FOR PRODUCING CONJUGATES THEREOF

(71) Applicants: F. HOFFMANN-LA ROCHE AG, Basel (CH); INSTITUT PASTEUR, Paris (FR); CENTRE NATIONAL DE LA RECHERCHE SCIENTIFIQUE, Paris (FR); COMMISSARIAT A L'ENERGIE ATOMIQUE ET AUX ENERGIES ALTERNATIVES, Paris (FR)

(72) Inventors: Pierre Lafaye, Malakoff (FR); Sylvie Bay, Paris (FR); Benoit Delatour, Cachan (FR); Marc Dhenain, Limours (FR); Charles Duyckaerts, Saint-mande (FR); Tengfei Li, Courbevoie (FR); Matthias Vandesquille, Fontenay-aux-roses (FR); Christian Czech, Grenzach-wyhlen (DE); Fiona Grueninger, Arlesheim (CH)

(73) Assignees: F. HOFFMAN-LA ROCHE AG, Basel (CH); CENTRE NATIONAL DE LA RECHERCHE SCIENTIFIQUE (CRNS), Paris (FR); INSTITUT PASTEUR, Paris (FR); COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/035,582

(22) PCT Filed: Nov. 13, 2014

(86) PCT No.: PCT/IB2014/066019
§ 371 (c)(1),
(2) Date: May 10, 2016

(87) PCT Pub. No.: WO2015/071856
PCT Pub. Date: May 21, 2015

(65) Prior Publication Data
US 2016/0347831 A1   Dec. 1, 2016

(30) Foreign Application Priority Data
Nov. 13, 2013   (EP) .................................... 13306553

(51) Int. Cl.
| | |
|---|---|
| C07K 16/18 | (2006.01) |
| G01N 33/68 | (2006.01) |
| A61K 49/16 | (2006.01) |
| C07H 21/04 | (2006.01) |
| A61K 47/48 | (2006.01) |
| A61K 51/10 | (2006.01) |
| A61K 49/00 | (2006.01) |
| A61K 49/10 | (2006.01) |
| A61K 39/00 | (2006.01) |

(52) U.S. Cl.
CPC ........ *C07K 16/18* (2013.01); *A61K 47/48538* (2013.01); *A61K 49/0058* (2013.01); *A61K 49/108* (2013.01); *A61K 49/16* (2013.01); *A61K 51/1018* (2013.01); *G01N 33/6896* (2013.01); *A61K 2039/505* (2013.01); *C07K 2317/22* (2013.01); *C07K 2317/51* (2013.01); *C07K 2317/565* (2013.01); *C07K 2317/569* (2013.01); *C07K 2317/92* (2013.01); *G01N 2333/4709* (2013.01); *G01N 2800/2821* (2013.01); *G01N 2800/387* (2013.01); *G01N 2800/52* (2013.01)

(58) Field of Classification Search
CPC ............ C07K 2317/22; C07K 2317/51; C07K 2317/565; C07K 2317/92; A61K 51/1018; A61K 49/16; A61K 19/108; A61K 49/0058; A61K 47/48538; A61K 2039/505; G01N 33/6896; G01N 2333/4709
See application file for complete search history.

(56) References Cited

U.S. PATENT DOCUMENTS

2013/0177568 A1   7/2013   Bhatt et al.

FOREIGN PATENT DOCUMENTS

| EP | 2 008 666 A1 | 12/2008 |
|---|---|---|
| EP | 2 009 445 A1 | 12/2008 |
| WO | 2004/044204 A2 | 5/2004 |

OTHER PUBLICATIONS

Rutgers et al: "Differential recognition of vascular and parenchymal beta amyloid deposition", Neurobiology of Aging, vol. 32, No. 10, Oct. 1, 2011 (Oct. 1, 2011), pp. 1774-1783.
Nabuurs et al: "In Vivo Detection of Amyloid-[beta] Deposits Using Heavy Chain Antibody Fragments in a Transgenic Mouse Model for Alzheimer's Disease", PLOS ONE, vol. 7, No. 6, Jun. 1, 2012 (Jun. 1, 2012), p. e38284.
European Patent Office, International Search Report, PCT/IB2014/066019, Mar. 2, 2015.
European Patent Office, Written Opinion of ISA, PCT/IB2014/066019, Mar. 2, 2015.

*Primary Examiner* — Kimberly A. Ballard
(74) *Attorney, Agent, or Firm* — Arrigo, Lee & Guttman LLP

(57) ABSTRACT

The present invention relates to variable domain of a camelid heavy-chain antibodies directed to amyloid β and conjugates thereof. The present invention also relates to the use of these antibody conjugates for treating or diagnosing disorders mediated by amyloid β deposits.

32 Claims, 25 Drawing Sheets

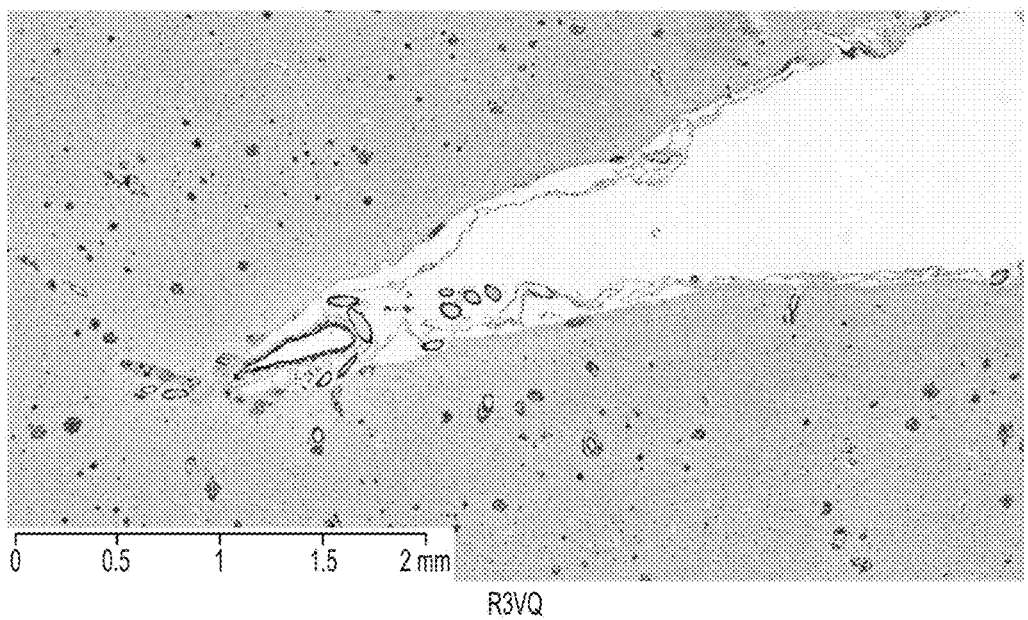
R3VQ
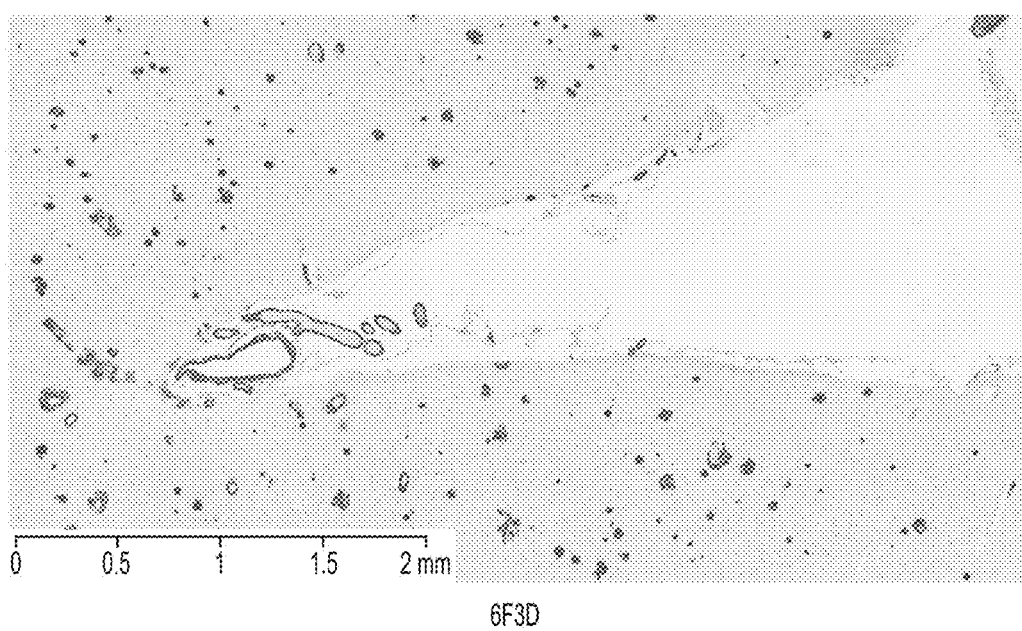
6F3D
FIG. 1

```
A7    MAEVQLQASGGGLVQAGGSRRLSCAVSGRTFSSYNMGWFRQAPGEEREFVAAINWS-ASTYYAD
B10   MAEVQLQASGGGLVQAGGSLRLSCAVSGRTFSSYNMGWFRQAPGKEREFVAAINWS-ASTYYAD
R3VE  MAEVQLEASGGGLVQTGDSLRLSCADSGSTFRNYNIGWFRQTPGQAREFVAAVSRTGISTHVAD
R3VQ  MAEVQLQASGGGLVQTGDSLRLSCADSGSTFRNYNIGWFRQTPGQAREFVAAVSRTGISTHVAD
F12   MADVQLQASGGGLVQPGGSLELSCAASGSTFSINVMGWYRQSPDGVRDLVATITAN-GVTNYAA

A7    SVKGRFTISRDNAKNTVYLQMNSLKPEDTAVYYCNLHVATTSYFQTSDY---WGQGTQVTVSS
B10   SVKGRFTISRDNAKNTVYLQMNSLKPEDTAVYYCNLHVATTSYFQTSDY---WGQGTQVTVSS
R3VE  SLQGRFTISRDNAKNTVYLQMNSLKPEDTAVYSCAAGRPGVGAVNRAMDYDYWGQGTQVTVSS
R3VQ  SLQGRFTISRDNAKNTVYLQMNSLKPEDTAVYSCAAGRPGVGAVNRAMDYDYWGQGTQVTVSS
F12   SVKGRFTISKDNAKNTVFLQMNSVKPEDTAVYICNVEGEYSGSYVADFDS--WGQGTQVTVSS
```

A7: SEQ ID NO. 14
B10: SEQ ID NO. 15
R3VE: SEQ ID NO. 5
R3VQ: SEQ ID NO. 4
F12: SEQ ID NO. 16

*FIG. 10A*

MGSSHHHHHHSSGLVPRGSAAAVQLQASGGGLVQTGDSLRLSCADSGSTFRNY
NIGWFRQTPGQAREFVAAVSRTGISTHVADSLQGRFTISRDNAKNTVYLQMNSL
KPEDTAVYSCAAGRPGVGAVNRAMDYDYWGQGTQVTVGGGSCSA (SEQ ID NO: 8)

*FIG. 10B*

MGSSHHHHHHSSGLVPRGSAAAEVQLEASGGGLVQTGDSLRLSCADSGSTFRNY
NIGWFRQTPGQAREFVAAVSRTGISTHVADSLQGRFTISRDNAXNTVYLQMNSL
KPEDTAVYSCAAGRPGVGAVNRAMDYDYWGQGTQVTVGGGSCSA (SEQ ID NO : 18)

*FIG. 10C*

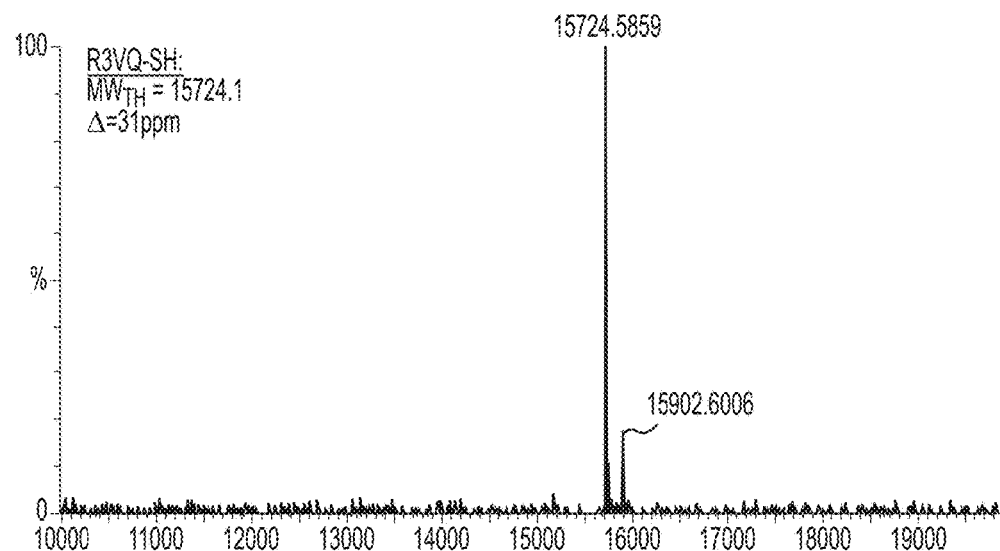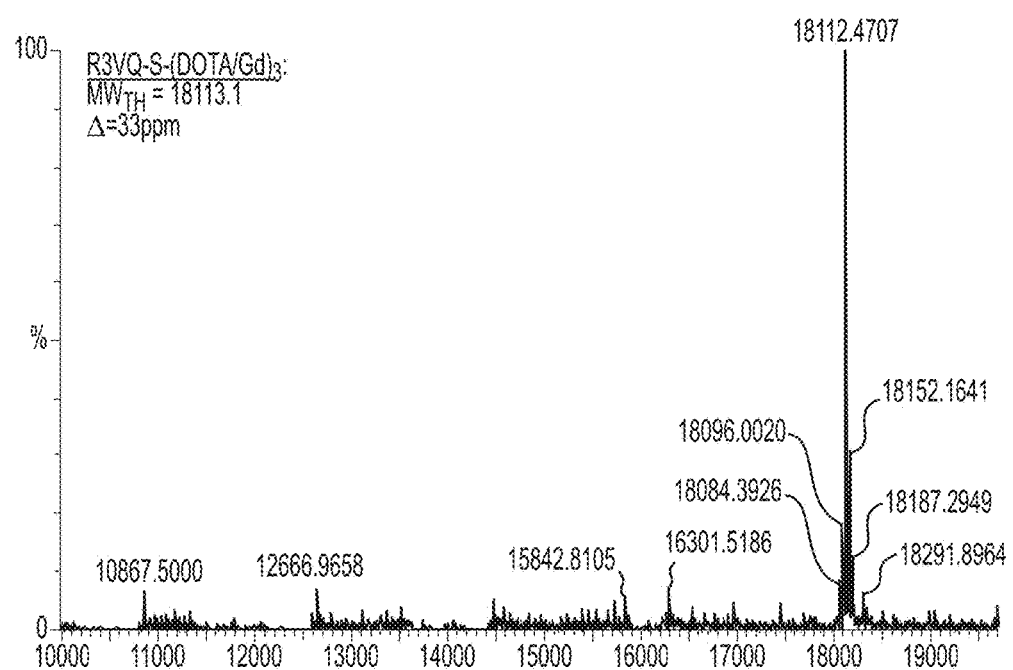
FIG. 11A

CAMELID SINGLE-DOMAIN ANTIBODY DIRECTED AGAINST AMYLOID BETA AND METHODS FOR PRODUCING CONJUGATES THEREOF

SEQUENCE LISTING

The instant application contains a Sequence Listing which has been filed electronically in ASCII format and is hereby incorporated by reference in its entirety. Said ASCII copy, created on Aug. 15, 2016, is named PCT00003490_SL.txt and is 13,204 bytes in size.

The present invention relates to antibodies directed to amyloid β and conjugates thereof. The present invention also relates to the use of these antibody conjugates for treating or diagnosing disorders mediated by amyloid β deposits. Finally, the present invention also relates to coupling methods for obtaining VHH coupled with a substance of interest (functional conjugates), and more generally to an oligopeptide coupled with a substance of interest.

About 70% of all cases of dementia are due to Alzheimer's disease (AD) which is associated with selective damage of brain regions and neural circuits critical for cognition. Alzheimer's disease is characterized by neurofibrillary tangles in particular in pyramidal neurons of the hippocampus and numerous amyloid plaques containing mostly a dense core of amyloid deposits and diffuse halos.

The extracellular neuritic plaques contain large amounts of a pre-dominantly fibrillar peptide termed "amyloid β", "A-beta", "amyloid P", "AP4", "Aβ", "βA4", "P-A4" or "AP"; see Selkoe (1994), Ann. Rev. Cell Biol. 10, 373-403; Koo (1999), PNAS Vol. 96, pp. 9989-9990; U.S. Pat. No. 4,666,829 or Glenner (1984), BBRC 12, 1131. This β amyloid is derived from "Alzheimer precursor protein/β-amyloid precursor protein" (APP). APPs are integral membrane glycoproteins (see Sisodia (1992), PNAS Vol. 89, pp. 6075) and are endoproteolytically cleaved within the Aβ sequence by a plasma membrane protease, α-secretase. Further secretase activity, in particular β-secretase and γ-secretase activity leads to the extracellular release of amyloid-β comprising proteins of different size such as 39 amino acids (Aβ39), 40 amino acids (Aβ40), 42 amino acids (Aβ42) or 43 amino acids (Aβ43); see Sinha (1999), PNAS 96, 11094-1053; Price (1998), Science 282, 1078-1083; WO 00/72880 or Hardy (1997), TINS 20, 154. It is of note that Aβ has several naturally occurring forms, whereby the human forms are referred to as the above mentioned Aβ39, Aβ40, Aβ41, Aβ42 and Aβ43. The form Aβ42 has the amino acid sequence (starting from the N-terminus): DAEFRHDS-GYEVHHQKLVFFAEDVGSNKGAIIGLMVGGVVIA (SEQ ID NO. 12). In Aβ41, Aβ40, Aβ39, the C-terminal amino acids A, IA and VIA are missing, respectively. In the Aβ43-form an additional threonine residue is comprised at the C-terminus of the above depicted sequence (SEQ ID NO. 12). Mutation of the APP gene can lead to modification of the Aβ sequence and to an increased accumulation of aggregated Aβ.

The major components of these extracellular neuritic plaques are the water-soluble forms Aβ40 or Aβ42. However, the initial focus on the water-insoluble fibrillar amyloid as the central structure in AD pathology has evolved during the last 15 years. This was due to several outstanding discoveries such as the finding of a water-soluble fraction of oligomeric Aβ in the human brain (Kuo Y. M. et al., 1996, J Biol Chem, 271, 4077-81). These isolated soluble oligomers were toxic to neurons in culture. The presence and toxicity of oligomeric Aβ was then confirmed and the name of ADDLs (Aβ-derived diffusible ligands) was proposed for these structures (Lambert M. P. et al., 1998, Proc Natl Acad Sci U.S.A., 95, 6448-53). Depending on conditions, ADDL compositions can contain predominantly trimers-hexamers, with larger structures of up to 24-mers. ADDLs show important regionally selective neurotoxicity, sparing neurons in the cerebellum while selectively killing neurons in hippocampal CA1 region and entorhinal cortex (Klein W. L. et al., 2001, Trends in Neurosciences, 24, 219-224). Moreover, oligomers are able to inhibit hippocampal long-term potentiation (LTP) in rats in vivo (Walsh D. M. et al., 2002, Nature, 416, 535-9) and in hippocampal slices (Wang H. W. et al., 2002, Brain Res., 924, 133-40; Wang Q. et al., 2004, J Neurosci., 24, 3370-8). It has been shown that cognitive deficits are directly attributable to low amounts of soluble oligomeric forms of Amyloid β; trimers and at a lesser extent, dimers and tetramers being particularly active (Cleary J. P. et al., 2005, Nat Neurosc., 8, 79-84; Townsend M. et al., 2006, J Physiol, 572, 477-92).

Amyloid plaques occur a long time (up to 30 years) before the occurrence of Alzheimer's disease (Sperling R. A., 2011, Alzheimer's and Dementia, 7:280-92; Villemagne V. L., 2013, Lancet Neurol., 12:357-67) and according to the amyloid cascade hypothesis, amyloid is responsible for the cascade of events leading to all the lesions of AD (Hardy J. A., 1992, Science, 256:184-5). The early detection of amyloid is thus critical for the follow-up of Alzheimer's disease and its therapy. Imaging of amyloid plaques is also critical in animal models to screen new drugs.

Amyloid deposits can also be associated to vascular lesions (amyloid angiopathy). Amyloid accumulates under similar forms in the course of other diseases such as Down's syndrome.

Several methods have been developed to detect the lesions of amyloid diseases, in particular Alzheimer's disease. To date, in humans, the most widely used method is based on positron emission tomography (PET) imaging. Amyloid load can be for instance evaluated in vivo in patients but with more difficulties in animals by using PET radioligands such as the $^{11}$C-PIB (Klunk W. E., 2004, Ann Neurol., 55:306-19) or the $^{18}$F-AV-45 (Doraiswamy P. M., 2012, Neurology, 79:1636-44). The need to radiolabel the compound is the main disadvantage of PET-based methods. In humans, this leads to an exposure to ionizing radiation. In preclinical studies, as only a limited number of centers are allowed to manipulate radioactive compounds, PET exams cannot be used for large scale evaluation of new drugs and for routine diagnosis. Also, the short half-life of isotopes such as $^{11}$C (20 minutes) requires the presence of a cyclotron on site when one use ligands based on $^{11}$C such as the PIB. Ligands based on $^{18}$F have a longer half-life (110 min), but this half-life is still relatively short. This requires a strong logistic associated with the supply, handling and administration of a radiotracer that has a limited shelf-life requiring careful planning. Moreover, PET imaging suffers from a low resolution, hampering its use for routine pre-clinical research in small brain-sized AD animal models. In summary it can be stated that new alternatives have to be found with no delay to image in vivo AD and Down's syndrome brain lesions both in patients and in animal models of the disease.

Besides PET imaging, nuclear magnetic resonance (NMR) imaging or Magnetic Resonance Imaging (MRI) can also be used to detect AD brain lesions. During the last decade many efforts have been made to develop new approaches that enable plaque detection by MRI. Protocols without contrast agents allow the visualization of some Aβ deposits due to the naturally occurring deposition of circulating iron within amyloid plaques. However, iron accumulation in amyloid deposits can be low in humans (Dhenain M., 2002, NMR Biomed., 15:197-203) and only occurs in the late stages of the disease or in focal brain regions in mice (Dhenain M., 2009, Neurobiol Aging 30:41-53). Several protocols are based on the use of specific contrast agents. Some groups have for instance developed contrast agents using Aβ-derived peptides, magnetically labeled with either gadolinium (Gd) or monocrystalline iron oxide nanoparticles (MION) (Wadghiri, Y. Z., 2003, Magn Reson Med., 50:293-302; Poduslo, J. F., 2002, Neurobiol Dis., 11:315-329). Ex vivo and in vivo detection has been achieved with these methods but still requires permeation of the blood-brain barrier (BBB), which cannot be performed with high efficiency and reproducibility and which can be harmful (e.g., use of mannitol to transiently open the blood-brain barrier). Hence these methods suffer from the necessity to open the BBB and are thus not used in non-experimental situations. Other groups developed methods to target the amyloid thanks to antibodies targeting amyloid plaques (Ramakrishnan, M., 2008, Pharm Res., 25:1861-1872). Recent approaches to detect amyloid plaques by MRI are based on the use of small antibody fragments displaying an increased potential to cross the BBB (polyamine modified Fab fragments) and targeting amyloid plaques. These antibodies are linked to a contrastophore allowing their detection by MRI (Ramakrishnan, M., 2008, Pharm Res., 25:1861-1872). However, antibodies, like other large plasma proteins such as albumin, do not readily traverse the BBB and remain generally confined to the plasmatic compartment of the circulation. One potential mechanism of enhanced delivery of antibodies molecules through the BBB is cationization, where surface carboxyl groups are conjugated with primary amino groups and the isoelectric point (pI) of the antibody is raised (Bickel U. et al., 2001, Adv Drug Deliv Rev., 46:247-279). The positive charges of cationized proteins bind to negative charges on cellular surfaces and this interaction triggers absorptive-mediated endocytosis of the cationized protein into the cell. With respect to cationization of immunoglobulins, recent studies have shown that this procedure results in enhanced absorptive mediated endocytosis by isolated brain capillaries in vitro and that this endocytosis process leads to the net transcytosis of the cationized IgG into the brain in vivo. A major limitation in the application of cationized antibodies is the decrease of their antigen binding properties. Indeed, the affinity of cationized monoclonal antibodies is affected because arginine and lysine, usually involved in the binding with the antigen, are modified by the cationization process (Triguero D. et al., 1991, J Pharmacol Exp Ther. 258:186-192).

Conventional immunoglobulins are heterotetramers composed of two heavy chains and two light chains with a combined molecular weight of about 150 kDa. In members of the family Camelidae a significant proportion of serum antibodies are homodimeric IgGs with a molecular weight of about 80 kD (Hamers-Casterman C. et al., 1993, Nature, 363:446-448). These heavy chain immunoglobulins (Ig) contain three domains and their variable region is referred to as VHH. Recombinant VHHs (~12-14 kD in size) constitute intact antigen-binding domains and exhibit a broad antigen-binding repertoire. Their hypervariable regions are expanded and exhibit unique characteristics, such as the substitution of three to four hydrophobic framework residues (which interact with the $V_L$ in conventional antibodies) by more hydrophilic amino acids. To stabilize the enlarged CDRs, VHHs may possess in addition of the canonical disulfide bond, an extra disulfide bound between CDR1 and CDR3 in dromedaries and CDR2 and CDR3 in llamas (Harmsen, M. M. and De Haard H. J., 2007, Appl Microbiol Biotechnol., 77:13-22; Muyldermans S., 2001, J Biotechnol., 74:277-302). The extended CDR3 loop can adopt a convex conformation, whereas conventional paratopes are limited to concave or flat structures (Muyldermans S., 2001, J Biotechnol., 74:277-302). These features allow VHHs to recognize unique epitopes that are poorly immunogenic for conventional antibodies (Lafaye P. et al., 2009, Mol Immuno., 46:695-704; Wernery U., 2001, J Vet Med B Infect Dis Vet Public Health., 48:561-568). Although VHHs are by definition monovalent antibodies, which by default exclude any avidity effect, their biological activity measured as $IC_{50}$ in vitro can be similar to conventional, bivalent antibody molecules (Thys B. et al., 2010, Antiviral Research., 87:257-264).

It was proposed that homodimeric VHHs offer new perspectives for in vivo immunodiagnosis. Methods, such as phage display, have been described to select antigen-specific VHH from the VHH repertoire of immunized camels or llamas. The VHH genes are cloned in phage display vectors, the antigen binders are obtained by panning and selected VHH are expressed in bacteria. The recombinant VHHs have a number of advantages compared with the conventional antibody fragments (Fab or scFv), because only one domain has to be cloned and because these VHHs are well expressed, highly soluble in aqueous environments and are stable at high temperature. Because of their small size of about 12-14 kDa, VHHs rapidly pass the renal filter, which has a cutoff of about 60 kDa, resulting in rapid blood clearance. In addition, the small size results in a fast tissue penetration. The VHH short serum half-life of about 2 h, compared to 4 h for scFv and 50 h for IgG, is advantageous for in vivo diagnosis using imaging and for the targeting of VHHs coupled to a substance of interest for treating a disorder, as one can expect that unspecifically bound VHH will be quickly removed from the tissues.

Li T. et al. (2012, Faseb J., 26:3969-3979) have obtained VHHs directed against GFAP, an intermediate filament protein specific for astrocytes. Using intra-carotid injections in living mice, the authors have shown that these native VHHs act as <<transbodies>> since they are naturally able to cross the BBB, to diffuse in the brain tissues, to penetrate into astrocytes and to bind specifically GFAP epitopes (see also International Application WO 2010/004432).

More generally, a VHH having an isoelectric point of at least 8.5 is able to transmigrate across the BBB by micro-pinocytosis and absorptive-mediated endocytosis. Such a VHH can be used for the preparation of a peptide vector for delivering a substance of interest across a mammal blood-brain barrier (International Applications WO 2009/004495 and WO 2010/004432).

International Application WO 2004/044204 discloses the preparation of a library of variable fragments of camelid single-chain antibodies (VHHs) capable to specifically bind the amyloid β peptide 42 (Aβ42) in vitro. These VHHs have been obtained by immunizing a *Lama pacos* with Aβ42. Among these VHHs, one particular VHH, referred to as VHH V31-1, has been described to specifically recognize the carboxy terminal end of Aβ42 peptide (Aβ42) in its fibrillar form by ELISA and intraneuronal Aβ42 deposits by immunohistochemistry. However, in International Application WO 2009/004494, the inventors of WO 2004/044204 have clearly shown by immunohistochemistry that contrary to what was described in WO 2004/044204, VHH V31-1 does not recognize Aβ42 in its water-insoluble fibrillar form but specifically recognizes water-soluble low-molecular oligomers (i.e., mono-, di-, tetra- and dodeca-mers) of Aβ42 (see also Lafaye P. et al., 2009, Mol Immunol., 46:695-704). In International Application WO 2009/004494, the inventors of WO 2004/044204 have further studied two VHHs disclosed in WO 2004/044204, namely VHH 61-3 and VHH L1-3. They have shown by immunohistochemistry that stained AD brain tissue slices revealed very faint intraneuronal immunoreactivity for VHH 61-3 and an undetectable intraneuronal immunoreactivity for VHH L1-3.

Rutgers K. S. et al. (2011, Neurobiol. Aging, 32:1774-83) report the selection by phage display of 8 llama-derived heavy chain antibody fragments (VHHs) specific for amyloid from non-immune and immune libraries and the determination of their affinity and specificity for amyloid β by phage-ELISA, immunohistochemistry and surface plasmon resonance. The authors have shown that the 8 VHHs recognize distinct amyloid β epitopes in vitro, which is consistent with the distinct immunogens. The authors have also shown that 3 of these VHHs recognize vascular and parenchymal amyloid β deposits, while the remaining 5 VHHs recognize vascular amyloid β specifically (failing to bind to parenchymal amyloid β). The authors conclude that vascular and parenchymal amyloid β deposits are heterogeneous in epitope presence/availability and that VHHs specific for amyloid β can be used as reagents for in vivo imaging to discriminate between vascular and parenchymal amyloid β deposits.

Nabuurs R. J. A. et al. (2012, PLoS One, 7:e38284) have further characterized in vivo two of the VHHs disclosed by Rutgers et al., namely VHHs ni3A and pa2H. The authors have found that contrary to what was reported in Rutgers et al. both VHHs showed affinity for parenchymal and vascular amyloid β deposits. Indeed, Rutgers K. S. et al. reported that in immunohistochemistry on human tissue, ni3A specifically targeted only vascular amyloid β. Nabuurs R. J. A. et al. further report that VHHs ni3A and pa2H have a too low brain uptake to be used for in vivo imaging.

There is therefore a need to provide means and methods for diagnosing disorders mediated by amyloid β deposits and monitoring disease progression of such disorders, in particular Alzheimer's disease and Down's syndrome, in vivo by neuroimaging. There is also a need to provide means and methods for treating such disorders.

Within the framework of research that has led to the present invention, the inventors have immunized an alpaca with Aβ42. They have obtained two VHHs referred to as R3VQ and R3VE. R3VQ and R3VE have the amino acid sequence SEQ ID NO. 4 and SEQ ID NO. 5 respectively and both comprise a CDR1 (Complementarity Determining Region 1) of amino acid sequence SEQ ID NO. 1, a CDR2 of amino acid sequence SEQ ID NO. 2 and a CDR3 of amino acid sequence SEQ ID NO. 3. R3VQ differs from R3VE by only one amino acid at position 7 of the amino acid sequence: residue 7 of R3VQ and R3VE is respectively glutamine (Q) and glutamic acid (E). The 3 first amino acid residues (M-A-E) and the 2 last amino acid residues (S-S) of the amino acid sequence of both VHHs R3VQ and R3VE can be deleted without modifying the properties of these VHHs. The VHHs R3VQ and R3VE lacking these amino acid residues are indifferently referred to as R3VQ and R3VE respectively. R3VQ and R3VE have similar properties.

When assessed by ELISA and immunohistochemistry in vitro, R3VQ and R3VE have similar binding properties for Aβ. VHH R3VQ is able to recognize specifically the fibrillar form of amyloid β but not the oligomeric (i.e., non-fibrillar) form. Using immunohistochemistry techniques the inventors have found that this VHH (as well as VHH R3VE) labels specifically amyloid plaques present on human AD brain tissue samples as well as on brain sections from dedicated mouse models harboring amyloid deposits.

VHH R3VQ is also able to cross a mammal non-compromised blood brain barrier in vivo.

Further, VHH R3VQ was conjugated to a substance of interest, such as a MRI contrast agent, and a chelating agent, following two strategies:

The first strategy was to use a non-site specific approach and comprising a conjugation step of a chelating agent, such as 1,4,7,10-tetraazacyclododecane-1,4,7,10-tetraacetic acid (DOTA), with lysine residues of VHH or VHH derivatives according to the invention, followed by a chelation step of the obtained ligand with a substance of interest, such as MRI contrast agent like the paramagnetic agent gadolinium (Gd). When assessed in vivo by IHC and MRI, the R3VQ-N-(DOTA/Gd)$_{n'}$ conjugate (FIG. 9, Compound 2) was able to recognize amyloid plaques in mouse after intra cerebro-ventricular injection.

The second strategy was to use a site specific approach which involves the conjugation of the VHH R3VQ, and more generally the labeling of any VHH comprising a cystein residue at the C- or N-terminus, by thio-addition (conjugation step) with a thiol-reactive compound bearing a substance of interest, and preferably a maleimido compound bearing a substance of interest.

Whereas the non-site specific conjugation required an initial buffer exchange, the site-specific conjugation between the R3VQ-SH 3 and the maleimido-(DOTA/Gd)$_3$ 4 can implemented directly in a PBS/NaCl/imidazole buffer. Specific thio-addition on cystein could be efficiently controlled in mild conditions, said strategy allowing a reduction of the number of step reaction and an improvement of the overall yield of the process, without any of the potential side reactions previously mentioned in A. Papini et al., Int. J. Pept. Protein Res., 1992, 39, 348-355; B. Rudolf et al., J. Organomet. Chem, 1996, 522, 313-315; J. Paulech et al., Biochim. Biophys. Acta, 2013, 1834, 372-379. It is thus surprising to improve the overall yield in a so significant manner, without any side reaction on the lysine or the histidine of the VHH, and with an overall maintenance of the function and the 3D structure of the VHH.

Recombinant proteins are routinely expressed with a His-Tag which allows their purification by immobilized metal affinity chromatography (IMAC). When using a $Ni^{2+}$ nitrilotriacetic acid resin, they are typically eluted in a PBS buffer containing 500 mM imidazole. In the non-site specific approach (FIG. 9A), the nitrogens of the imidazole can promote the NHS ester hydrolysis (i.e. degrade the reactive species), and thereby interfere with the conjugation (G. T. Hermanson, Bioconjugate Techniques, Academic Press, 2013; P. Cuatrecasas et al., Biochemistry, 1972, 11, 2291-2299). A buffer exchange step must therefore be included in the process between the upstream affinity purification and the conjugation to remove the imidazole. The overall yields range from 60 to 67%. First site specific experiments (FIG. 9B) were also performed after a buffer exchange (FIG. 9B, Method 1) resulting in the conjugate R3VQ-S-(DOTA/Gd)$_3$ 5 in a 70% yield. Side-reaction between imidazole and maleimide groups was expected as previously reported by several groups showing the histidine side-chain alkylation (A. Papini et al.; B. Rudolf et al.; J. Paulech et al.). Nonetheless, the maleimido-(DOTA/Gd)$_3$ 4 could be directly conjugated to the R3VQ-SH VHH 3 in the affinity column elution buffer (FIG. 9B, Method 2), with limited excess of maleimide reagent and despite a large molar excess of imidazole. This second strategy leads to an overall yield of 83%.

Accordingly, the present invention provides an isolated variable domain of a camelid heavy-chain antibody (referred to as VHH) directed against the fibrillar form of amyloid β, characterized in that its amino acid sequence comprises, from the N-terminus to the C-terminus, the amino acid sequence SEQ ID NO. 1 (corresponding to the CDR1), the amino acid sequence SEQ ID NO. 2 (corresponding to the CDR2) and the amino acid sequence SEQ ID NO. 3 (corresponding to the CDR3).

In a preferred embodiment, said VHH comprises or consists of the amino acid sequence selected from the group consisting of:
SEQ ID NO. 4, corresponding the full-length form of R3VQ,
SEQ ID NO. 5, corresponding the full-length form of R3VE,
SEQ ID NO. 6, corresponding the short form of R3VQ, and
SEQ ID NO. 7, corresponding the short form of R3VE, preferably selected from the group consisting of SEQ ID NO. 4 and SEQ ID NO. 6.

As used herein, the term "isolated" refers to a VHH which has been separated from a component of its natural environment. In some embodiments, a VHH is purified to greater than 95% or 99% purity as determined by, for example, electrophoretic (e.g., SDS-PAGE, isoelectric focusing (IEF), capillary electrophoresis) or chromatographic (e.g., gel filtration, ion exchange or reverse phase HPLC). For review of methods for assessment of antibody purity, see, e.g., Flatman et al., 2007, J. Chromatogr. B 848:79-87.

As used herein, the term "VHH" refers to the variable antigen-binding domain from a camelid (camel, dromedary, llama, alpaca, etc.) heavy-chain antibody (See Nguyen V. K. et al., 2000, The EMBO Journal, 19, 921-930; Muyldermans S., 2001, J Biotechnol., 74, 277-302 and for review Vanlandsehoot P. et al., 2011, Antiviral Research 92, 389-407). A VHH can also be named Nanobody (Nb).

Advantageously, the VHH according to the present invention has a basic isoelectric point, preferably between 8.5 and 9.5.

The invention encompasses natural, recombinant or synthetic VHHs as defined above.

As used herein, the term "recombinant" refers to the use of genetic engineering methods (cloning, amplification) to produce said VHH.

As used herein, the term "synthetic" refers to the production of said VHH by in vitro chemical or enzymatic synthesis.

The VHH according to the present invention can be in the form of a monomer or a homomultimer, such as a homodimer or a homotrimer.

The present invention also provides an isolated camelid serum, preferably an alpaca serum, comprising a VHH according to the present invention.

The present invention also provides an oligopeptide of formula P-C-Z or Z-C-P, preferably P-C-Z, wherein:
P is a 8 to 800 amino acid peptide having no reduced cystein residue,
C is a cystein residue,
Z represents a 1-10 amino acid spacer, preferably a 1-10 neutral or negatively charged amino acid spacer, wherein the amino acid residues of Z are identical or different and wherein Z does not contain a cystein residue.

Advantageously, the amino acid residues of the amino acid spacer Z are selected from the group consisting of alanine, valine, serine, leucine, isoleucine, phenylalanine, glycine, serine, threonine, tyrosine, asparagine and glutamine, preferably alanine, valine and serine.

In a preferred embodiment, the oligopeptide has the formula P-C-Z or Z-C-P, preferably P-C-Z, wherein:
P is a 8 to 800 amino acid peptide having no reduced cystein residue,
C is a cystein residue,
Z represents
a) a 2-10 amino acid spacer, preferably a 2 amino acid spacer, wherein the amino acid residues of Z are selected from the group consisting of serine (S), alanine (A), valine (V) and glycine (G), and more preferably serine (S), alanine (A) and valine (V), and wherein at least two amino acid residues of Z are different, or
b) a 2-10 amino acid spacer, preferably a 2-10 neutral or negatively charged amino acid spacer, wherein Z comprises the dipeptide serine-alanine (S-A) or serine-valine (S-V) and wherein Z does not contain a cystein residue.

Advantageously, the cystein residue C is sterically accessible.

Advantageously, when Z is defined in a), the amino acid spacer Z comprises 1 or at least 1 serine.

Advantageously, when Z is defined in a), the amino acid spacer Z consists in serine and alanine residues only or in serine and valine residues only.

In a preferred embodiment of this oligopeptide, the amino acid spacer Z consists of a 2 amino acid sequence, such as the amino acid sequences S-A or S-V.

The amino acid peptide P can also be by order of increasing preference a 50 to 800, 100 to 800, 100 to 700, 100 to 500, 100 to 400, 100 to 300 or 100 to 250 amino acid peptide.

Advantageously, the amino acid peptide P comprises or consists of a peptide P' able to selectively bind an antigen. P' is preferably selected from the group consisting of a variable domain of a camelid heavy-chain antibody (VHH), a Fab fragment of a conventional antibody, a F(ab)'$_2$ fragment of a conventional antibody, a Fv fragment of a conventional antibody, scFv fragment of a conventional antibody, an immunoglobulin new antigen receptor (IgNAR), a nanofitin, a DARPin, an anticalin, an affibody, an affilin, an avimer, a monobody and a kunitz domain.

Fab, F(ab)'$_2$, Fv and scFv fragments of a conventional antibody are well known to the person skilled in the art. IgNARs are reviewed in Dooley H. et al., 2006, Dev Comp Immunol., 30:43-56. Nanofitins (e.g., affitin) are reviewed in Mouratou B. et al., 2007, Proc Natl Acad Sci U.S.A., 104:17983-8. DARPins are reviewed in Binz H. K. et al., 2003, J. Mol. Biol., 332: 489-503. Anticalins are reviewed in Skerra A, 2008, FEBS J., 275:2677-83. Affibodies are reviewed in Nord K. et al., 1997, Nature Biotechnol., 15:772-777. Affilins are reviewed in Ebersbach H. et al., 2007, J. Mol. Biol., 372:172-185. Avimers are reviewed in Silverman J. et al., 2005, Nature Biotechnol., 23:1556-1561. Monobodies (or adnectins) are reviewed in Koide A. et al., 1998, J. Mol. Biol., 284:1141-51. Kunitz domains are reviewed in Lehmann A., 2008, Expert opinion on biological therapy, 8:1187-99.

In a preferred embodiment, P' is a VHH, such as a VHH according to the present invention.

The amino acid peptide P of the oligopeptide of formula P-C-Z can have at its C-terminus a 1-10 amino acid spacer Y, preferably a 1-10 neutral or negatively charged amino acid spacer, wherein the amino acid residues of said amino acid spacer Y are identical or different, and wherein said amino acid spacer Y does not contain a cystein residue.

The amino acid peptide P of the oligopeptide of formula Z-C-P can have at its N-terminus a 1-10 amino acid spacer Y, preferably a 1-10 neutral or negatively charged amino acid spacer, wherein the amino acid residues of said amino acid spacer Y are identical or different, and wherein said amino acid spacer Y does not contain a cystein residue.

Advantageously, the amino acid residues of the amino acid spacer Y are selected from the group consisting of alanine, valine, serine, leucine, isoleucine, phenylalanine, glycine, serine, threonine, tyrosine, asparagine and glutamine, preferably alanine, valine, serine and glycine.

Preferably, the amino acid spacer Y represents a 4 neutral amino acid spacer, such as the amino acid sequence G-G-G-S(SEQ ID NO. 11).

The amino acid peptide P of the oligopeptide of formula P-C-Z can also have at its N-terminus a 1-50 amino acid sequence X, wherein the amino acid residues of said amino acid sequence X are identical or different, and wherein said amino acid sequence X does not contain a cystein residue.

The amino acid peptide P of the oligopeptide of formula Z-C-P can also have at its C-terminus a 1-50 amino acid sequence X, wherein the amino acid residues of said amino acid sequence X are identical or different, and wherein said amino acid sequence X does not contain a cystein residue.

The amino acid sequence X can comprise a tag such as a 6×His tag (SEQ ID NO. 9) and an enzyme cleavage site, such as the thrombin cleavage site of amino acid sequence LVPRGS (SEQ ID NO. 10).

In a preferred embodiment, the oligopeptide according to the present invention has the formula P'-C-Z, P'-Y-C-Z, X-P'-C-Z, X-P'-Y-C-Z, Z-C-P', Z-C-Y-P', Z-C-P'-X, or Z-C-Y-P'-X, wherein P' is preferably a VHH, such as a VHH according to the present invention.

The present invention also provides a VHH derivative consisting of a polypeptide comprising a VHH according to the present invention, provided that said VHH comprised in said polypeptide is able to bind the fibrillar form of amyloid β.

In a particular embodiment, said VHH derivative comprises, from the N-terminus to the C-terminus, an amino acid tag such as a 6×His tag, an enzyme cleavage site, such as a thrombin cleavage site, a VHH, an amino acid spacer, a cystein and a second amino acid spacer. Such a VHH derivative corresponds to an oligopeptide according to the present invention having the formula X-P'-Y-C-Z, wherein P' is a VHH.

In a preferred embodiment, said VHH derivative has the amino acid sequence SEQ ID NO. 8 (R3VQ-SH).

The present invention also provides an isolated polynucleotide encoding an oligopeptide, a VHH, or a VHH derivative according to the present invention.

An example of polynucleotide encoding a VHH derivative according to the present invention is the sequence SEQ ID NO: 17 (nucleotide sequence encoding R3VQ-SH).

A polynucleotide according to the present invention may be obtained by well-known methods of recombinant DNA technology and/or of chemical DNA synthesis.

The present invention also provides a recombinant expression cassette comprising a polynucleotide according to the present invention under the control of a transcriptional promoter allowing the regulation of the transcription of said polynucleotide in a host cell. Said polynucleotide can also be linked to appropriate control sequences allowing the regulation of its translation in a host cell.

The present invention also provides a recombinant vector (e.g., a recombinant expression vector) comprising a polynucleotide according to the present invention. Advantageously, said recombinant vector is a recombinant expression vector comprising an expression cassette according to the present invention.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The present invention also provides a host cell containing a recombinant expression cassette or a recombinant vector according to the present invention. The host cell is either a prokaryotic or eukaryotic host cell.

The terms "host cell" refers to a cell into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A prokaryotic host cell expressing VHH R3VQ of amino acid sequence SEQ ID NO. 4 was deposited on Nov. 12, 2013, at the Collection Nationale de Cultures de Microorganismes (CNCM), 28 rue du Dr Roux, 75724 Paris Cedex 15, France, under the number I-4818.

A prokaryotic host cell expressing VHH R3VQ-SH of amino acid sequence SEQ ID NO: 8 was deposited on Nov. 12, 2013, at the Collection Nationale de Cultures de Microorganismes (CNCM), 28 rue du Dr Roux, 75724 Paris Cedex 15, France, under the number I-4819.

The present invention also provides a method for producing in a host cell as defined above an oligopeptide of formula P-C-Z or Z-C-P according to the present invention, comprising the steps of:
  providing a host cell containing a recombinant expression cassette or a recombinant vector according to the present invention,
  culturing said host cell,
  and optionally purifying the oligopeptide of formula P-C-Z or Z-C-P.

Methods for purifying an oligopeptide are well known in the art, such as chromatography (e.g., ion exchange chromatography, gel permeation chromatography and reversed phase chromatography).

The present invention also provides a diagnostic or therapeutic agent comprising a VHH, a VHH derivative or an oligopeptide according to the present invention, linked, directly or indirectly, covalently or non-covalently to a substance of interest.

The substance of interest according to the present invention may or may not permeate the mammal or human blood-brain barrier. If the substance of interest permeates said blood-brain barrier, then the use of a VHH, a VHH derivative or an oligopeptide according to the present invention can allow enhancing the delivery of said substance of interest across the blood-brain barrier.

In an embodiment, said substance of interest is a diagnostic or therapeutic compound.

In another embodiment, said substance of interest is a liposome or a polymeric entity comprising a diagnostic or therapeutic compound (A. J. L. Villaraza et al., Chem Rev. 2010, 110, 2921-2959).

Advantageously, said diagnostic compound is selected from the group consisting of:
- an enzyme such as horseradish peroxidase, alkaline phosphatase, glucose-6-phosphatase or beta-galactosidase;
- a fluorophore such as green fluorescent protein (GFP), blue fluorescent dyes excited at wavelengths in the ultraviolet (UV) part of the spectrum (e.g. AMCA (7-amino-4-methylcoumarin-3-acetic acid); Alexa Fluor® 350), green fluorescent dyes excited by blue light (e.g. FITC, Cy2, Alexa Fluor® 488), red fluorescent dyes excited by green light (e.g. rhodamines, Texas Red, Cy3, Alexa Fluor® dyes 546, 564 and 594), or dyes excited with far-red light (e.g. Cy5) to be visualized with electronic detectors (CCD cameras, photomultipliers);
- a radioisotope such as $^{18}$F, $^{11}$C, $^{13}$N, $^{15}$O, $^{68}$Ga, $^{82}$Rb, $^{44}$Sc, $^{64}$Cu, $^{86}$Y, $^{89}$Zr, $^{124}$I, $^{152}$Tb that can be used for PET imaging or $^{67}$Ga, $^{81m}$Kr, $^{99m}$Tc, $^{111}$In, $^{123}$I, $^{125}$I, $^{133}$Xe, $^{201}$Tl, $^{155}$Tb, $^{195m}$Pt that can be used for SPECT/scintigraphic studies, or $^{14}$C, $^{3}$H, $^{35}$S, $^{32}$P, $^{125}$I that can be used for autoradiography or in situ hybridisation, or $^{211}$At—, $^{212}$Bi—, $^{75}$Br—, $^{76}$Br—, $^{131}$I—, $^{111}$In, $^{177}$Lu—, $^{212}$Pb—, $^{186}$Re—, $^{188}$Re—, $^{153}$Sm—, $^{90}$Y that can be used to label the compounds;
- a NMR or MRI contrast agent such as the paramagnetic agents gadolinium (Gd), dysprosium (Dy) and manganese (Mn), and the superparamagnetic agents based on iron oxide (such as MION, SPIO or USPIO) or iron platinium (SIPP), and X-nuclei such as $^{18}$F, $^{13}$C, $^{23}$Na, $^{17}$O, $^{15}$N;
- a nanoparticle such as gold nanoparticles (B. Van de Broek et al., ACSNano, Vol. 5, No. 6, 4319-4328, 2011) or quantum dots (A. Sukhanova et al., Nanomedicine, 8 (2012) 516-525).

In a preferred embodiment, said diagnostic compound is a MRI contrast agent, more preferably gadolinium.

When the diagnostic agent is used for detection, it may comprise a radioactive atom for scintigraphic studies, for example $^{99}$Tc or $^{123}$I, or a spin label for nuclear magnetic resonance (NMR) imaging (also known as MRI), such as $^{13}$C, $^{9}$F, Fe, Gd, $^{123}$I, $^{111}$In, Mn, $^{15}$N or $^{7}$O.

Advantageously, said therapeutic compound is selected from a peptide, an enzyme, a nucleic acid, a virus and a chemical entity. It can be an analgesic compound, an anti-inflammatory compound, an antidepressant compound, an anticonvulsant compound, a cytotoxic compound or an anti-neurodegenerative compound.

The substance of interest as defined above can be directly and covalently or non-covalently linked to the VHH, VHH derivative or oligopeptide according to the present invention either to one of the terminal ends (N or C terminus) of said VHH, VHH derivative or oligopeptide, or to the side chain of one of the amino acids of said VHH, VHH derivative or oligopeptide. The substance of interest can also be indirectly and covalently or non-covalently linked to said VHH or VHH derivative by means of a spacer either to one of the terminal ends of said VHH or VHH derivative, or to a side chain of one of the amino acids of said VHH or VHH derivative. Conventional linking methods of a substance of interest to a peptide, in particular an antibody, are known in the art (e.g., See TERNYNCK and AVRAMEAS, 1987, "Techniques immunoenzymatiques" Ed. INSERM, Paris or G. T. Hermanson, Bioconjugate Techniques, 2010, Academic Press).

Many chemical cross-linking methods are also known in the art. Cross-linking reagents may be homobifunctional (i.e., having two functional groups that undergo the same reaction) or heterobifunctional (i.e., having two different functional groups). Numerous cross-linking reagents are commercially available. Detailed instructions for their use are readily available from the commercial suppliers. A general reference on polypeptide cross-linking and conjugate preparation is: WONG, Chemistry of protein conjugation and cross-linking, CRC Press (1991).

The VHH, VHH derivative or oligopeptide according to the present invention may be labeled with specific radioisotopes or NMR or MRI contrast agents or fluorophores or nanoparticles or enzymes using general organic chemistry techniques known to the art. See, e.g., March, J. ADVANCED ORGANIC CHEMISTRY: REACTIONS, MECHANISMS, AND STRUCTURE (3rd Edition, 1985) or G. T. Hermanson, Bioconjugate Techniques, 2010, Academic Press.

In addition, the VHH, VHH or oligopeptide derivative according to the present invention also may be labeled with any suitable radioactive iodine isotope, such as, but not limited to $^{131}$I, $^{125}$I, or $^{123}$I, by iodination of a diazotized amino derivative directly via a diazonium iodide (see Greenbaum, 1936, F. Am. J. Pharm., 108:17), or by conversion of the unstable diazotized amine to the stable triazene, or by conversion of a non-radioactive halogenated precursor to a stable tri-alkyl tin derivative which then can be converted to the iodo compound by several methods well known to the art. See, Satyamurthy and Barrio, 1983, J. Org. Chem., 48: 4394; Goodman et al., 1984, J. Org. Chem., 49:2322, and Mathis et al., 1994, J. Labell. Comp. and Radiopharm., 905; Chumpradit et al., 1991, J. Med. Chem., 34: 877; Zhuang et al., 1994, J. Med. Chem. 37:1406; Chumpradit et al., 1994, J. Med. Chem. 37:4245.

In particular, the VHH, VHH derivative or oligopeptide according to the present invention can be labeled with $^{123}$I for SPECT by any of several techniques known to the art. See, e.g., Kulkarni, 1991, Int. J. Rad. Appl. & Inst. (Part B) 18: 647.

The VHH or VHH derivative according to the present invention also may be radiolabeled with known metal radiolabels, such as Technetium-99m ($^{99m}$Tc). Modification of the substituents to introduce ligands that bind such metal ions can be effected without undue experimentation by one of ordinary skill in the radiolabeling art. The metal radiolabeled VHH or VHH derivative according to the present invention can then be used to detect amyloid β deposits. Preparing radiolabeled derivatives of $^{99m}$Tc is well known in the art. See, for example, Zhuang et al., 1999, Nuclear Medicine & Biology, 26:21 7-24; Oya et al., 1998, Nuclear Medicine & Biology, 25: 135-40; Horn et al., 1997, Nuclear Medicine & Biology, 24:485-98.

The invention also relates to coupling methods for obtaining a VHH or VHH derivative according to the invention coupled, directly or indirectly, with a substance of interest (functional conjugate).

According to a first strategy, a VHH or VHH derivative according to the invention is conjugated to a substance of interest by using a non-site specific approach. Said non-site specific method comprises a conjugation step of a substance of interest with a VHH or VHH derivative according to the invention.

When the substance of interest is a metal, such as a NMR or MRI contrast agent (for example, paramagnetic agents gadolinium (Gd), dysprosium (Dy) and manganese (Mn), and superparamagnetic agents based on iron oxide or iron platinium, and X-nuclei such as $^{18}$F, $^{13}$C, $^{23}$Na, $^{17}$O, $^{15}$N, or such as a metallic radioisotope (for example, $^{90}$Y, $^{177}$Lu, $^{64}$Cu, $^{99m}$Tc, $^{111}$In, $^{212}$Pb, $^{212}$Bi) the non-site specific method implements a chelating agent and comprises the following steps:

(i) the conjugation of a chelating agent activated in the form of an ester or an anhydride, preferably in the form of an ester, with lysine residues of VHH or VHH derivative according to the invention, and (ii) the chelation of the ligand of step (i) with a substance of interest.

An alternative of the non-site specific method implementing a chelating agent is a method in which the substance of interest is "pre-chelated" with a chelating agent, such method comprising the following steps:

(i') the chelation of the substance of interest with a chelating agent activated in the form of an ester or an anhydride, preferably in the form of an ester, and (ii') the conjugation of the pre-chelated substance of interest of step (i') with lysine residues of VHH or VHH derivative according to the invention.

During the conjugation step (i) or (ii'), the temperature may varied from 1 to 40° C., and preferably from 4 to 20° C. The solution may be stirred from 1 to 6 hours. Preferably, the pH is maintained between 7 and 8.5 during the conjugation step (i) or (ii').

The conjugation step (i) or (ii') can be performed in PBS/NaCl with or without imidazole, and preferably in presence of imidazole.

During the conjugation step (i) or (ii'), the chelating agent activated in the form of an ester or an anhydride may be dissolved in a buffer solution, such as a phosphate buffered saline (PBS) solution.

In a preferred embodiment, the molar ratio between the chelating agent activated in the form of an ester or an anhydride and the amino functions of the lysine residues of VHH or VHH derivative ranges from 1 to 10, and is preferably of 4.

Between the conjugation step (i) and the chelation step (ii), or between the chelation step (i') and the conjugation step (ii'), there may have a buffer exchange step by diafiltration or dialyse. Advantageously, the solution is diafiltrated, for example with a Vivaspin™ device. During this buffer exchange step, the medium is cooled at a temperature ranging from 1 to 5° C. During this buffer exchange step, the buffer solution is exchanged for example with a sodium acetate solution, preferably under stirring from 0 to 6 hours, and more preferably from 2 to 3 hours.

During the chelation step (ii) or (i'), the solution is stirred from 1 to 4 hours, preferably from 2 to 3 hours. The chelation step is preferably performed from 1 to 60° C., and more preferably at 4° C.

Then, there may have a second buffer exchange step by diafiltration or dialyse. Advantageously, the solution is diafiltrated, for example with a Vivaspin™ device. During this second buffer exchange step, the medium is cooled at a temperature ranging from 1 to 5° C. During this second diafiltration step, the buffer solution is exchanged for example with a mixture PBS/NaCl, and may be concentrated by the same method (diafiltration).

Depending on the number of lysine, the substance of interest average density per VHH or VHH derivative may vary between 0 and the number of lysine+1. Preferably, the substance of interest average density per VHH or VHH derivative may vary between 0 and 5.

The non-site specific method according to the invention applies to the VHH and VHH derivative according to the invention, and can be extended to other VHH.

According to a second strategy, an oligopeptide according to the invention, including preferably a VHH derivative according to the present invention, is conjugated to a substance of interest by using a site specific approach. The site specific approach has the following advantages:

the labeled oligopeptide is chemically-defined as this method affords well-defined conjugates which is an essential feature in the perspective of human use (quality control, safety . . . ), the method is easy and standard as the oligopeptide labeling with the substance of interest can be performed in a single step with short reaction time and straightforward procedure. There is no need for in-process monitoring and no trade-off to achieve between the labeling degree and the binding properties. These are key advantages for further optimization, experiment repeatability, and production scale-up, the method does not affect oligopeptide key properties: for instance, when P comprises or consists of a VHH, the pI of the conjugate is maintained above 8.5 which should allow for the BBB crossing; in the final sample. Furthermore, there is no remaining unlabeled oligopeptide which may compete with the conjugate for the target; the mild conditions with short reaction time at physiological pH prevent the oligopeptide from potential degradation and/or loss of activity, the method is versatile as it allows a flexible and modular approach where various oligopeptides and contrast agents, or other molecules of interest, can be prepared separately, and then combined in a single step. As a result, a set of conjugates are easily accessible for optimization and downstream evaluation by IHC and MRI, and above all the method allows an improvement of the overall yield whilst reducing the number of steps reaction, without side reactions on the lysine or the histidine of the VHH, and with an overall maintenance of the function and the 3D structure of the VHH.

The site specific method according to the invention comprises a conjugation step between an oligopeptide according to the invention with a substance of interest bearing a thiol-reactive function.

In a preferred embodiment of the site specific method, the conjugation step is carried out between an oligopeptide according to the invention and a thiol-reactive compound bearing said substance of interest.

Advantageously, the thiol-reactive compound bearing a substance of interest is a maleimido compound, and preferably a maleimido compound of formula (I) or (I') as defined below.

The thio-addition between the cystein of the oligopeptide and the thiol-reactive compound can be performed at a temperature ranging from 0 to 20° C., preferably 4° C., for instance from 2 to 4 hours.

The thio-addition between the cystein of the oligopeptide and the thiol-reactive compound, such as the maleimido compound of formula (I) or (I') defined below, is preferably realized at a pH ranging from 4 to 7.5, and more preferably at 6.8. Below pH=4, the reaction does not work, and above 7.5 the reaction is non specific (reaction on lysine). To adjust the pH, the conjugation step (i) or (ii') can be performed in PBS/NaCl with or without imidazole, and preferably in presence of imidazole. The identification of such specific conditions for a thio-addition of a maleimido compound to a protein directly eluted from the purification column is surprising as it allows to save a step and to increase the overall yield of the process.

Then, there may have a buffer exchange step by diafiltration or dialyse. Advantageously, the solution is diafiltrated, for example with a Vivaspin™ device. Then, the solution may be concentrated by the same method (diafiltration).

However, when the conjugation step (i) or (ii') is performed in PBS/NaCl with imidazole, it is preferable not to perform subsequent diafiltration or dialyse step (in order not to remove the imidazole).

Whether it is for the non-specific method of for the specific method, the substance of interest may be as defined above.

According to a preferred embodiment, the substance of interest is a therapeutic or diagnostic compound as defined above, preferably a diagnostic compound selected from the group consisting of fluorophore, radioisotope and NMR or MRI contrast agent as defined above.

The Inventors have observed that when the substance of interest is a NMR or MRI contrast agent, the synthesized conjugates retain the critical functional properties of the unlabelled VHH.

According to a preferred embodiment, the substance of interest is a NMR or MRI contrast agent, such the paramagnetic agents gadolinium (Gd), dysprosium (Dy) and manganese (Mn), and the superparamagnetic agents based on iron oxides (such as MION, SPIO or USPIO) or iron platinium (SIPP), and X-nuclei such as $^{18}$F, $^{13}$C, $^{23}$Na, $^{17}$O, $^{15}$N, and more preferably the substance of interest is a NMR or MRI contrast agent selected from the paramagnetic agents gadolinium (Gd), dysprosium (Dy) and manganese (Mn).

The chelating agent may be chosen among 1,4,7,10-tetraazacyclododecane-1,4,7,10-tetracetic acid (DOTA), diethylene triamine penta-acetic acid (DTPA), 1,4,7-tris (carboxymethylaza)cyclododecane-10-azaacetylamide (DO3A), nitrilotriacetic acid (NTA) (Chong et al., 2008, 19, 1439), D-penicillamine (Pen), 2,3-dimercaptosuccinic acid (DMSA), 2,3-dimercapto-1-propanesulfonic acid (DMPS) (O. Andersen, Chem. Rev., 1999, 99, pp. 2683-2710), 2,3-dimercaptopropanol (BAL), triethylenetetramine (Trien), the ammonium tetrathiomolybdate (TTM) anion (G. J. Brewer, F. K. Askari, J. Hepatol., 2005, 42, pp. S13-S21), ethylenediaminetetraacetic acid (EDTA), 2-(p-isothiocyanatobenzyl)-6-methyl-diethylenetriaminepentaacetic acid (1B4M) (Nwe et al., J. Inorg. Biochem, 2011, 105, 722), hydroxypyridinone (HOPO) (Villaraza et al., Chem. Rev., 2010, 110, 2921).

When the substance of interest is gadolinium, DOTA is the preferred chelating agent.

The present invention also provides an oligopeptide of formula P-C-Z or Z-C-P as defined above wherein said cystein residue C is linked to at least one substance of interest through a sulphide bond, preferably through a thioether or disulfide bond. Advantageously, said cystein residue C is linked to at least one substance of interest through a thiol-reactive compound bearing said substance of interest.

In the sense of the invention, a thiol-reactive compound is a maleimido, a haloacetyl, an alkyl halide or an aziridine compound, an acryloyl derivative, an arylating agent, or a thiol-disulfide exchange reagent (Bioconjugate Techniques, G. T. Hermanson, 2010, Academic Press).

In the sense of the invention, a maleimido compound is a compound bearing at least one maleimide function, preferably from 1 to 6 maleimide functions, and more preferably one maleimide function.

Preferably, the thiol-reactive compound is a maleimido compound reacting with the cystein residue C through the C—C double bond of the maleimide function.

The maleimido compound of the invention may be of formula (I) as follows:

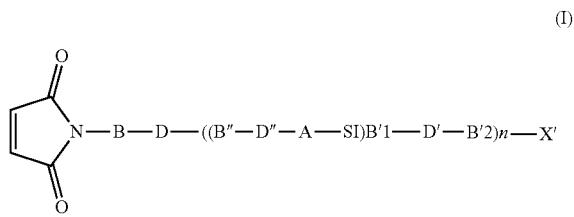

wherein:
B, B'$_1$, B'$_2$ and B", identical or different, are independently single bonds or spacers selected from polyols, such as polyethylene glycol (PEG) preferably having 2 to 12 oxyethylene (OE) units, polyolefins preferably having 2 to 12 aromatic rings, polyalkyls preferably having 2 to 12 carbon atoms, vinyl polymers such as poly(alkyl methacrylate) preferably having 2 to 12 methacrylate groups, polyaldehydes preferably having 2 to 12 carbonyl groups, polyacid esters preferably having 2 to 12 ester groups, D, D' and D", identical or different, are independently selected from amine, amide, amino-alcohol, urea, thiourea, carbamate, carbonate, ester, ether, thioether, aryl, heteroaryl such as triazole, oxime groups, A is a single bond or a chelating agent, SI is a substance of interest, X' is an acid, amine, amide, ester, ether, alkyl, alkenyl, alkynyl, aryl or heteroaryl function, and n=1 to 100, and preferably n=1, 2 or 3.

In the sense of the present invention:

Alkyl groups are chosen among ($C_1$-$C_{12}$)alkyl groups, and preferably ($C_1$-$C_6$)alkyl groups such as methyl, ethyl, n-propyl, isopropyl, n-butyl, sec-butyl, tert-butyl and isobutyl radicals;

Alkenyl groups are chosen among hydrocarbon chains of 2 to 12 carbon atoms, preferably 2 to 6, having at least one carbon-carbon double bond. Examples of alkenyl groups include ethenyl, propenyl, isopropenyl, 2,4-pentadienyl;

Alkynyl groups are chosen among hydrocarbon chains of 2 to 12 carbon atoms, preferably 2 to 6, having at least one carbon-carbon triple bond;

Aryl groups means any functional group or substituent derived from at least one simple aromatic ring; an aromatic ring corresponding to any planar cyclic compound having a delocalized π system in which each atom of the ring comprises a p-orbital, said p-orbitals overlapping themselves. More specifically, the term aryl includes, but is not limited to, phenyl, biphenyl, 1-naphthyl, 2-naphthyl, anthracyl, pyrenyl, and the substituted forms thereof. The aryl groups of the invention comprise preferably 4 to 12 carbon atoms, and more preferably 5 or 6 carbon atoms;

Heteroaryl groups means any functional group or substituent derived from at least one aromatic ring as defined above and containing at least one heteroatom selected from P, S, O and N. The term heteroaryl includes, but is not limited to, furan, pyridine, pyrrole, thiophene, imidazole, pyrazole, oxazole, isoxazole, triazole, thiazole, isothiazole, tetrazole, pyridazole, pyridine, pyrazine, pyrimidine, pyridazine, benzofurane, isobenzofurane, indole, isoindole, benzothiophene, benzo[c]thiophene, benzimidazole, indazole, benzoxazole, benzisoxazole, benzothiazole, quinoline, isoquinoline, quinoxaline, quinazoline, cinnoline, purine and acridine. The aryl and heteroaryl groups of the invention comprise preferably 4 to 12 carbon atoms, and more preferably 5 or 6 carbon atoms;

The acid, amine, amide, ester, ether and thioether groups according to the invention have preferably 1 to 12, and more preferably 1 to 6 carbon atoms.

According to a preferred embodiment, A is a chelating agent and the substance of interest SI is a NMR or MRI contrast agent.

Advantageously, the chelating agent A is selected from 1,4,7,10-tetraazacyclododecane-1,4,7,10-tetracefic acid (DOTA), diethylene triamine pentaacetic acid (DTPA), 1,4,7-tris(carboxymethylaza)cyclododecane-10-azaacethylamide (DO3A), nitrilotriacetic acid (NTA), D-penicillamine (Pen), 2,3-dimercaptosuccinic acid (DMSA), 2,3-dimercapto-1-propanesulfonic acid (DMPS), 2,3-dimercaptopropanol (BAL), triethylenetetramine (Trien), the ammonium tetrathiomolybdate (TTM) anion, ethylenediaminetetraacetic acid (EDTA), 2-(p-isothiocyanatobenzyl)-6-methyl-diethylenetriaminepentaacetic acid (IB4M) or hydroxypyridinone (HOPO).

Advantageously, the substance of interest SI is gadolinium, and the chelating agent is DOTA.

According to a particularly preferred embodiment, the maleimido compound of the invention may be of formula (I'):

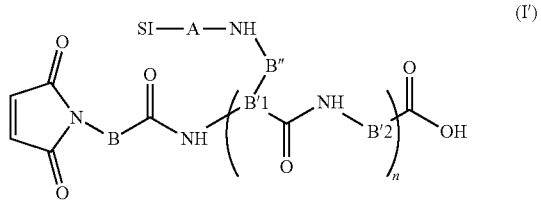

wherein B, B'$_1$, B'$_2$, B", A, SI and n are as defined above.

The maleimido compound of formula (I) or (I') may be synthesized through a solid-phase method, preferably using Fmoc chemistry, and more preferably on a Fmoc-Gly-Wang resin.

The maleimido compound of formula (I'):

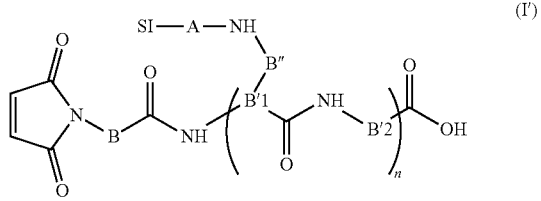

wherein B, B'$_1$, B'$_2$, B", A, SI and n are as defined above is also part of the invention.

Another object of the invention is an oligopeptide with a cystein residue linked to at least one substance of interest, and preferably linked to at least one substance of interest through a thiol-reactive compound, and more preferably a maleimido compound as defined according to the invention, said oligopeptide being obtainable according to the site specific method of the invention.

The present invention also provides a VHH or VHH derivative conjugated to a substance of interest obtainable according to the non-site specific method of the invention, and also a VHH conjugated to a thiol-reactive compound bearing a substance of interest obtainable according to the site specific method of the invention.

If the substance of interest is a peptide, the VHH or VHH derivative according to the present invention and said substance of interest can be produced by genetic engineering as a fusion polypeptide that includes the VHH or VHH derivative according to the invention and the suitable peptide. This fusion polypeptide can conveniently be expressed in known suitable host cells.

The VHH, the VHH derivative, the oligopeptide, the therapeutic or diagnostic agent, according to the present invention can be administered to a subject (a mammal or a human) by injection, such as intravenous, intraarterial, intrathecally (via the spinal fluid), intraperitoneal, intramuscular or subcutaneous injection, or by intranasal instillation.

When the VHH according to the present invention is administered to a human subject, then it can be humanized in order to reduce immunogenicity in human. Methods for producing humanized antibodies or fragments thereof are known in the art (Vincke C. et al., 2009, J Biol Chem., 284, 3273-84).

A diagnostic agent according to the present invention can be used in brain imaging, in diagnosing or monitoring a disorder mediated by amyloid β deposits, such as Alzheimer's disease (AD) and Down's syndrome.

The present invention also provides a kit comprising a VHH, a VHH derivative or an oligopeptide according to the present invention and a substance of interest as defined above.

In particular, the present invention also provides a kit for brain imaging, or for diagnosing or monitoring a disorder mediated by amyloid β deposits, such as Alzheimer's disease and Down's syndrome, comprising at least a VHH or VHH derivative and a diagnostic agent as defined above.

The present invention also provides the use of a diagnostic agent according to the present invention for diagnosing or monitoring a disorder mediated by amyloid β deposits, such as Alzheimer's disease and Down's syndrome, in a subject.

As used herein, a "subject" is a mammal, preferably a human, and most preferably a human suspected of having a disorder mediated by amyloid β deposits, such as Alzheimer's disease and Down's syndrome.

The present invention also provides an in vitro or ex vivo method for diagnosing a disorder mediated by amyloid β deposits, such as Alzheimer's disease and Down's syndrome, in a subject, comprising the steps of:

a) contacting in vitro an appropriate biological sample from said subject with a diagnostic agent according to the present invention, and b) determining the presence or the absence of amyloid β deposits, such as amyloid plaques, in said biological sample, the presence of said amyloid β deposits indicating that said subject has a disorder mediated by amyloid β deposits, such as Alzheimer's disease and Down's syndrome.

Step b) can be carried out by determining the presence or the absence of the VHH-antigen complex (i.e., VHH directed to the fibrillar form of amyloid β).

The present invention also provides an in vitro or ex vivo method for monitoring the progression or regression of a disorder mediated by amyloid β deposits, such as Alzheimer's disease and Down's syndrome, in a subject, comprising the steps of:

a) contacting in vitro an appropriate biological sample from said subject with a diagnostic agent according to the present invention, b) determining the amount of fibrillar form of amyloid β in said biological sample, and c) comparing the amount determined in step (b) with the amount of fibrillar form of amyloid β previously obtained for said subject, a significant increase in amount of fibrillar form of amyloid β constituting a marker of the progression of said disorder mediated by amyloid β deposits and a significant decrease of fibrillar form of amyloid β constituting a marker of the regression of said disorder mediated by amyloid β deposits.

As used herein the terms "significant increase" and "significant decrease" refer to a higher amount or lower amount respectively of fibrillar form of amyloid β in an appropriate biological sample with respect to the amount of fibrillar form of amyloid β in an appropriate biological sample from said subject, that was previously determined and used as a reference amount.

Step b) can also be carried out by determining the presence or the absence of the VHH-antigen complex.

Said appropriate biological sample can be a brain biopsy or post-mortem brain tissue.

According to the aspect of the invention which relates to a method of detecting amyloid β deposits in brain biopsy or post-mortem brain tissue, the method may involve incubating formalin-fixed tissue with a solution of a diagnostic agent according to the invention. Upon incubation, the diagnostic compound labels the amyloid β deposit in the tissue, and the stained or labeled amyloid β deposit can be detected or visualized by any standard method. Such detection means include microscopic techniques such as brightfield, fluorescence, laser-confocal and cross-polarization microscopy. The method of quantifying the amount of amyloid β in biopsy or post-mortem tissue involves, for example, incubating a diagnostic agent according to the present invention, or a water-soluble, non-toxic salt thereof, with homogenate of biopsy or post-mortem tissue. The tissue is obtained and homogenized by methods well known in the art. Advantageously the diagnostic compound is a radioisotope-labeled compound, although other diagnostic compounds such as enzymes, fluorophores or NMR or MRI contrast agents can be used.

The present invention also provides a method for in vivo imaging amyloid deposits in a subject comprising the steps of:

a) administering a detectable quantity of a diagnostic agent according to the present invention in a subject, preferably a human and, b) detecting the diagnostic agent in said subject by an imaging method.

This method according to the present invention allows determining the presence and location of amyloid deposits in brain of a subject, preferably a human.

As used herein a "detectable quantity" means that the amount of the diagnostic agent that is administered is sufficient to enable detection of binding of the diagnostic agent to amyloid β.

As used herein an "imaging effective quantity" means that the amount of the diagnostic agent that is administered is sufficient to enable imaging of binding of said diagnostic agent to amyloid β.

Imaging methods include non-invasive neuroimaging techniques such as magnetic resonance spectroscopy (MRS) or imaging (MRI), or gamma imaging such as positron emission tomography (PET) or single-photon emission computed tomography (SPECT), used to detect amyloid β deposits in vivo.

For purposes of in vivo imaging, the type of detection instrument available is a major factor in selecting a given label. For instance, gadolinium, iron or manganese based contrast agents can be used to detect the VHH or VHH derivative according to the present invention linked to said substances of interest by magnetic resonance spectroscopy (MRS) or imaging (MRI). Radioactive isotopes such as $^{19}$F are also particularly suitable for in vivo imaging in the methods of the present invention. The type of instrument used will guide the selection of the substances of interest. For instance, the radionucleide chosen must have a type of decay detectable by a given type of instrument. Another consideration relates to the half-life of the contrast agent or radionuclide. For radioisotopes, the half-life should be long enough so that it is still detectable at the time of maximum uptake by the brain, but short enough so that the subject does not sustain deleterious radiation. The radiolabeled VHH or VHH derivative according to the present invention can be detected using gamma imaging wherein emitted gamma irradiation of the appropriate wavelength is detected. Methods of gamma imaging include, but are not limited to, SPECT and PET. Preferably, for SPECT detection, the chosen radioisotope will lack a particulate emission, but will produce a large number of photons in a 140-200 keV range. For PET detection, the radiolabel will be a positron-emitting radionuclide such as $^{19}$F which will annihilate to form two 511 keV gamma rays which will be detected by the PET camera.

Generally, the dosage of the detectable diagnostic agent will vary depending on considerations such as age, condition, sex, and extent of disorder in the patient, contraindications, if any, concomitant therapies and other variables, to be adjusted by a physician skilled in the art. Administration to the subject may be local or systemic and accomplished intravenously, intraarterially, intrathecally (via the spinal fluid) or the like. Administration may also be intradermal or intracavitary, depending upon the body site under examination. After a sufficient time has elapsed for the compound to bind with the amyloid β, for example 30 minutes to 48 hours, the area of the subject under investigation is examined by routine imaging techniques such as MRS/MRI, SPECT, planar scintillation imaging, PET, and any emerging imaging techniques, as well. The exact protocol will necessarily vary depending upon factors specific to the patient, as noted above, and depending upon the body site under examination, method of administration and type of label used; the determination of specific procedures would be routine to the skilled artisan.

The present invention also provides an oligopeptide linked to a diagnostic compound according to the present invention as a diagnostic agent.

The present invention also provides a pharmaceutical composition comprising a therapeutic agent as defined above and a pharmaceutically acceptable carrier.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, Ringer's solutions, dextrose solution, and 5% human serum albumin. Liposomes, cationic lipids and non-aqueous vehicles such as fixed oils may also be used. The use of such media and agents for pharmaceutically active substances is well known in the art. Except insofar as any conventional media or agent is incompatible with a therapeutic agent as defined hereabove, use thereof in the composition of the present invention is contemplated.

The present invention also provides a VHH, a VHH derivative, a therapeutic agent or a pharmaceutical composition according to the present invention as a medicament, in particular for use in the treatment of a disorder mediated by amyloid β deposits, such as Alzheimer's disease and Down's syndrome.

The present invention also provides a method for preventing or treating a disorder mediated by amyloid β deposits, such as Alzheimer's disease and Down's syndrome, comprising administering to a subject in need thereof a therapeutic agent or a pharmaceutical composition according to the present invention.

As used herein, the terms "treatment" or "treating" includes the administration of the VHH, the VHH derivative, the therapeutic agent or the pharmaceutical composition according to the present invention to a patient who has a disorder, a symptom of disorder or a predisposition toward a disorder, with the purpose to cure, heal, alleviate, relieve, alter, remedy, ameliorate, improve or affect the disorder, the symptoms of the disorder, or the predisposition toward disorder.

The term "preventing" means that the progression of a disorder mediated by amyloid deposits, such as Alzheimer's disease is reduced and/or eliminated, or that the onset of a disorder mediated by amyloid β deposits, such as Alzheimer's disease is delayed or eliminated.

In another aspect, the present invention relates to the use of a VHH or a VHH derivative according to the invention, for the preparation of a peptide vector for delivering a substance of interest as defined above across a mammal blood-brain, preferably a human blood-brain barrier.

The present invention also provides an oligopeptide linked to a therapeutic compound according to the present invention as a therapeutic agent.

In addition to the preceding features, the invention further comprises other features which will emerge from the following description, which refers to examples illustrating the present invention, as well as to the appended figures.

FIG. 1 shows the immunohistochemical staining of amyloid plaques using the VHH R3VQ on human paraffin sections. 6F3D (Akiyama H. et al., 1996, Neurosci lett., 206:169-72) was used as a reference anti-Aβ antibody.

Figure 7A:
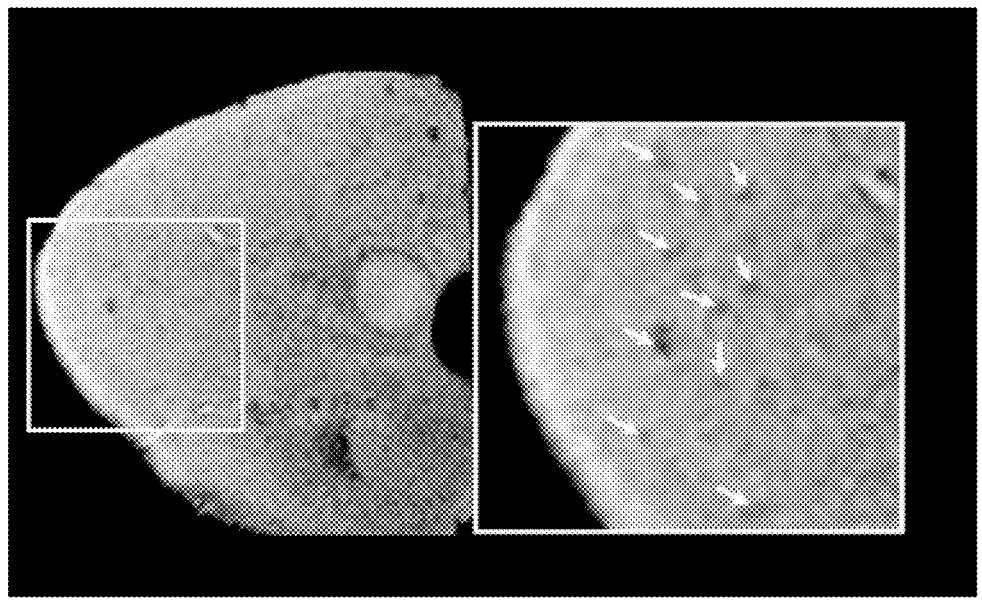

FIG. 7A: After soaking of a transgenic TauPS2APP mouse brain in a solution of anti-Aβ VHH-Gd 2e (R3VQ-N-(DOTA/Gd)$_{1-2}$ contrast agent (0.02 mg/ml, equivalent to a 0.01 mM of Gd), in vitro MR images shows hypointense spots (white arrows).

Figure 7B:
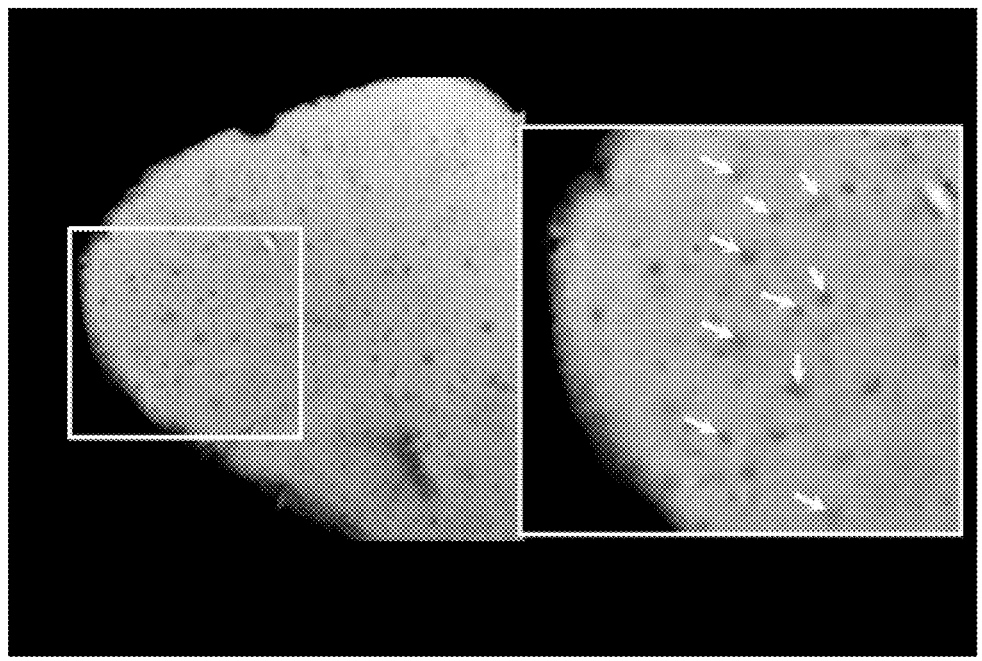

FIG. 7B shows the MRI detection of amyloid plaques on the same mouse revealed by the Gd-staining.

FIG. 7B shows the MRI colocalization of amyloid β plaques revealed by the Gd-staining on the same mouse (arrows).

Figure 7C:
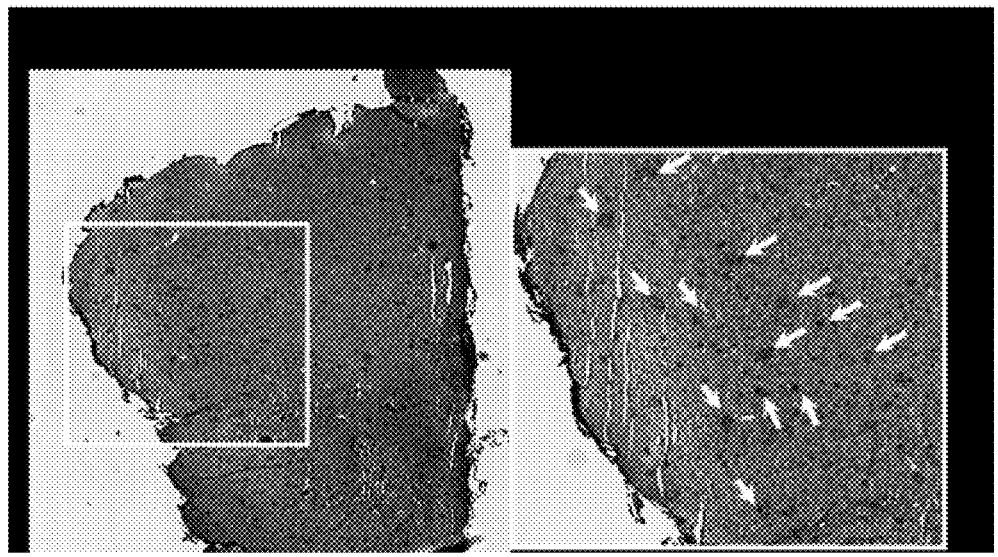

FIG. 7C shows the immunohistochemical staining of amyloid β plaques of the same mouse (arrows).

Figure 7D:
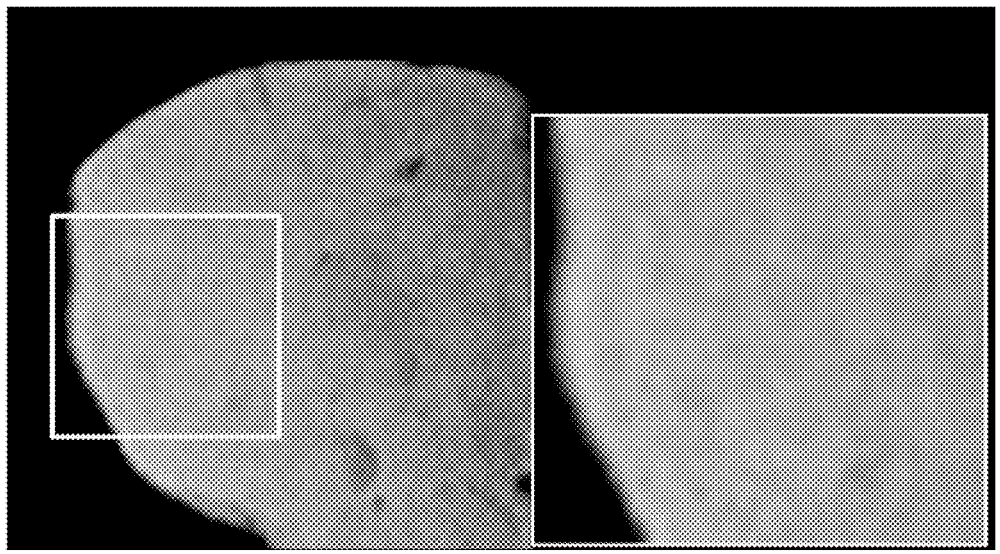

FIG. 7D is a control of a transgenic TauPS2APP mouse brain soaked with a Gadolinium solution at the same concentration (0.01 mM) used with R3VQ-N-(DOTA/Gd)$_{1-2}$ 2e.

Figure 8A:
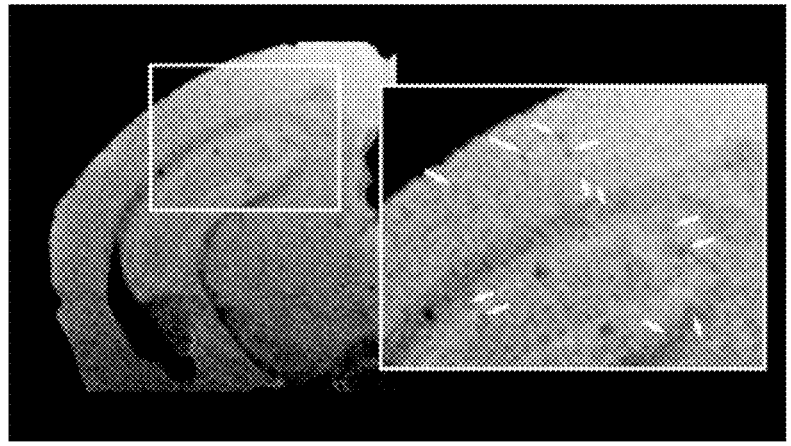

FIG. 8A: After intracerebroventricular injection, the anti-Aβ VHH-Gd 2e (R3VQ-N-(DOTA/Gd)$_{1-2}$; 1 µl/side at 1 µg/µl) showed hypointense spots on ex vivo MR images in the hippocampus (white arrows).

Figure 8B:
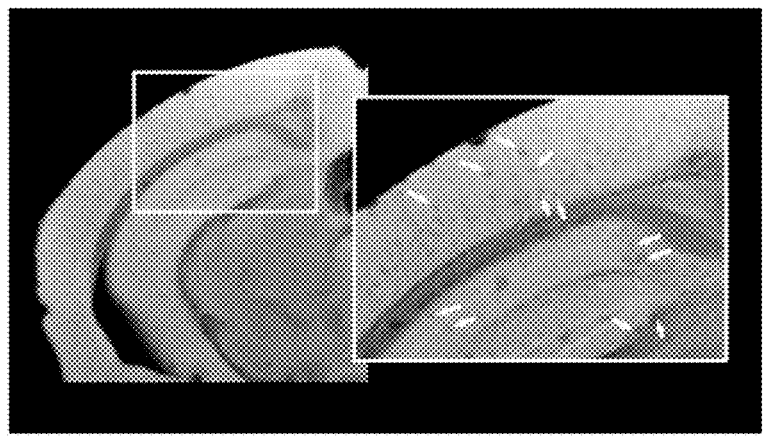

FIG. 8B shows the MRI colocalization of amyloid plaques revealed by the Gd-staining on the same mouse (arrows).

Figure 8C:
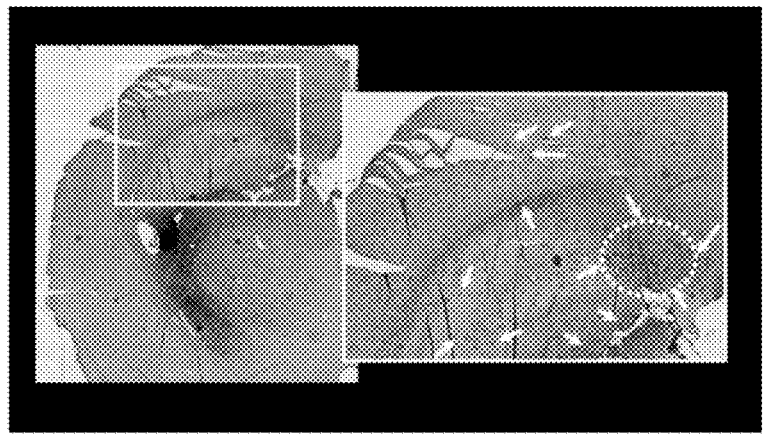

FIG. 8C shows the immunohistochemical staining of amyloid β plaques of the same mouse (arrows).

Figure 8D:
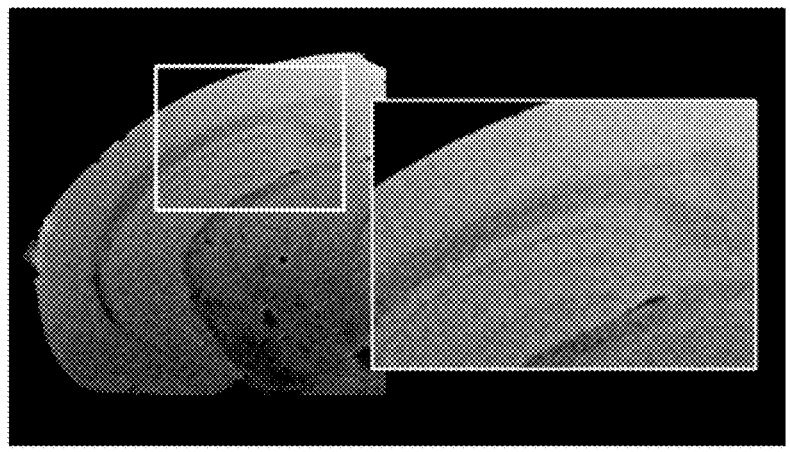

FIG. 8D is a control with the injection in a transgenic TauPS2APP mouse of a Gadolinium solution at the same concentration (0.1 mM) used with R3VQ-N-(DOTA/Gd)$_{1-2}$.

Figure 9A:
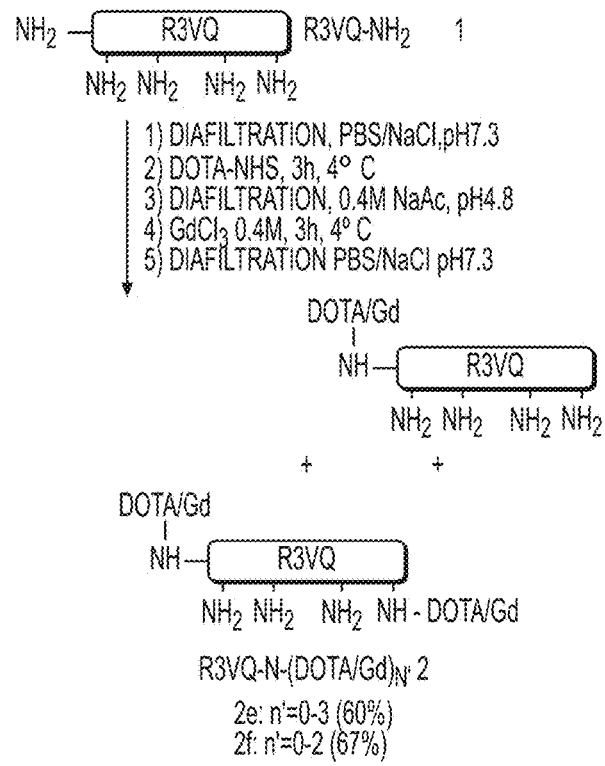
Figure 9B:
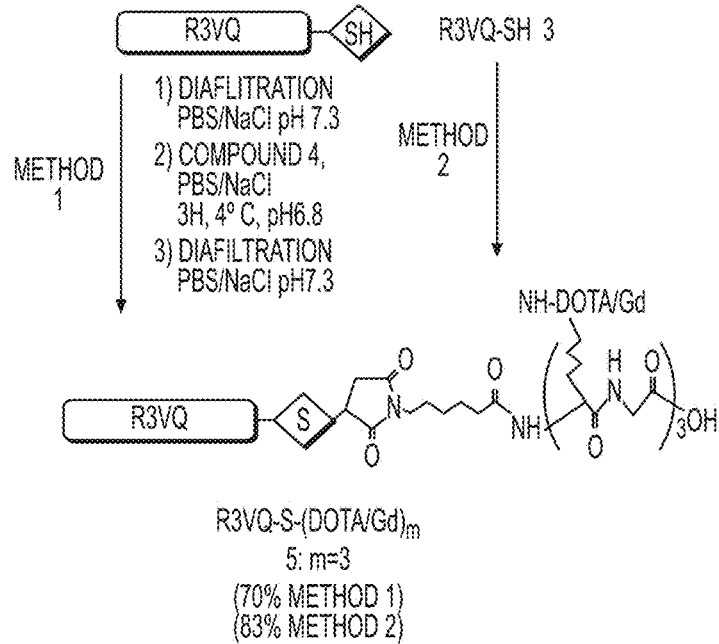
Figure 9C:
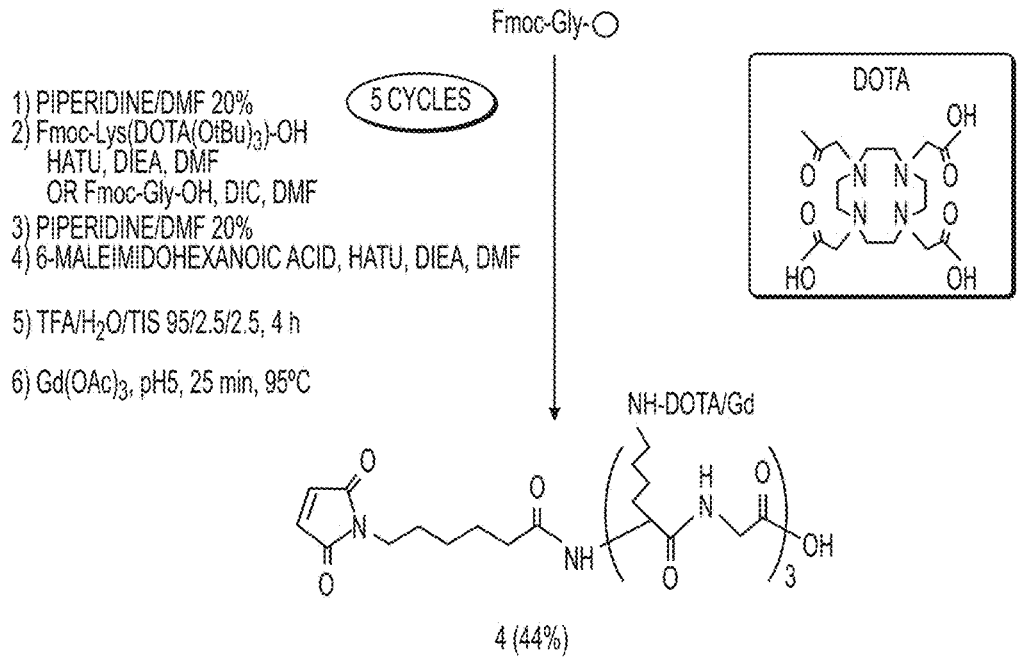

FIG. 9 shows the synthesis of labeled VHH (R3VQ) by non-site specific approach (A) and site specific approach (B). VHHs 1 and 3 were eluted from the affinity column in PBS/NaCl/Imidazole buffer. 1 was subjected to conjugation by a non-site-specific approach after a buffer exchange (A) and 3 was conjugated by a site-specific method (B) with (method 1) or without (method 2) a buffer exchange. The ligation sites are shown on the proteins. The labeling resulted in, respectively, polydisperse mixtures (2f shown as an example, and 2e) and chemically-defined conjugates (5 shown as an example). n'=average amount of DOTA/Gd per VHH (randomly distributed on different sites). m=exact amount of DOTA/Gd per VHH (located on a single site). The overall yield (indicated in brackets) includes all the steps from the starting protein in the affinity column elution buffer (net peptide contents). A solid-phase synthesis of the maleimido-(DOTA/Gd)₃ compound 4 (C) is described in FIG. 9 (C). 4 was prepared by the conventional solid-phase peptide methodology using Fmoc chemistry and HATU/DIEA as the coupling reagent. The overall yield is indicated in bracket. DOTA structural formula is shown in the inset.

FIG. 10 shows (A) the amino-acid sequence alignment of anti-Aβ VHHs A7, B 10, R3VE, R3VQ and F12; CDR1, CDR2, CDR3 are underlined, (B) the amino acid sequence of R3VQ-SH 3, (C) the amino acid sequence of R3VE-SH.

Figure 11B:
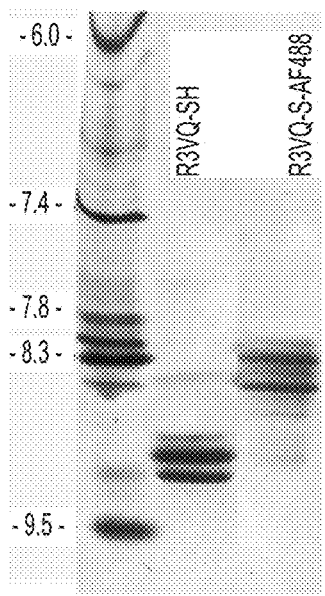
Figure 11C:
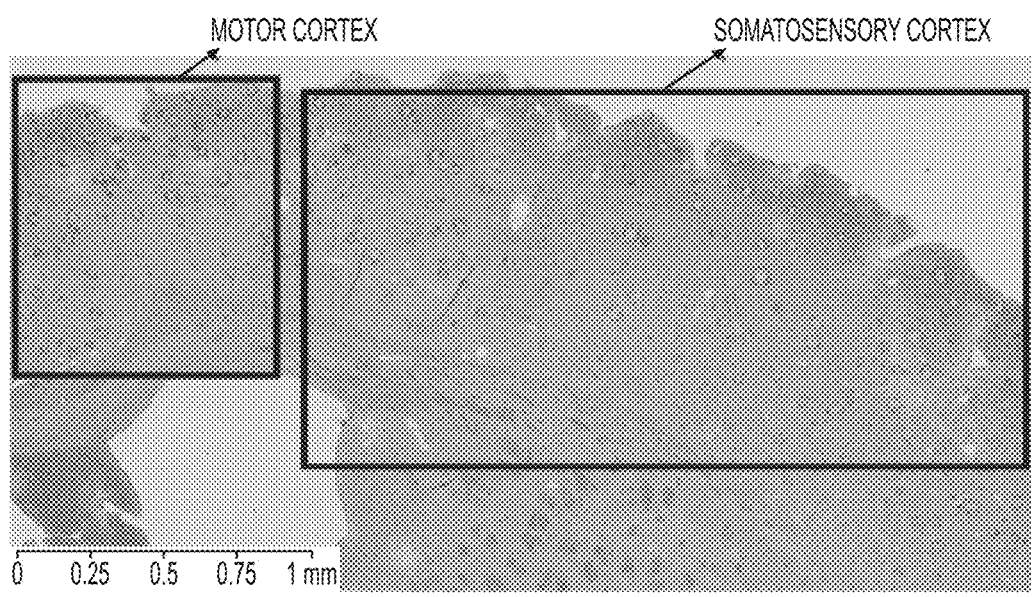

FIG. 11 shows the analysis and assessment of the properties of VHH R3VQ-S-(DOTA/Gd)₃ (compound 5 FIG. 9) obtained by site specific conjugation. (A) HPLC/MS. (B) IEF. (C) Evaluation of BBB crossing by IHC detection of VHHs in the brain after iv injection. Comparison with unconjugated protein R3VQ-SH is showed in A, B.

Figure 12:
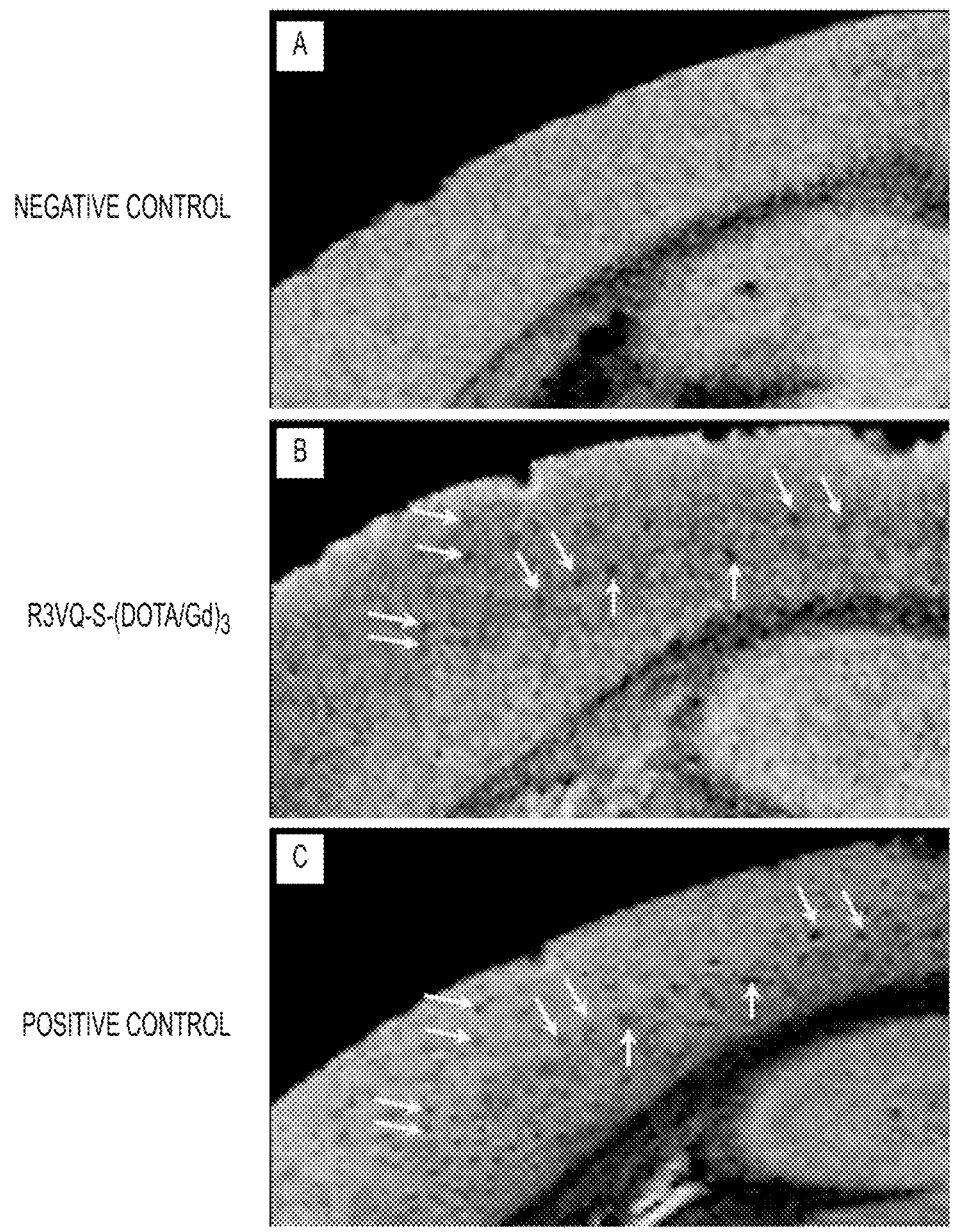

FIG. 12 shows the MRI detection of amyloid plaques after in vitro incubation with R3VQ-S-(DOTA/Gd)₃. Whereas no contrast anomalies could be detected in negative control PS2APP mice brains (A), several hypointense spots were revealed after in vitro incubation of PS2APP mice brains with R3VQ-S-(DOTA/Gd)₃ (B, white arrows). These hypointensity were colocalized with amyloid plaques highlighted by the Gd-staining procedure used as gold standard positive control for amyloid plaques detection by MRI (C, white arrows). Experiments were realized on a 7 T spectrometer.

Figure 13:
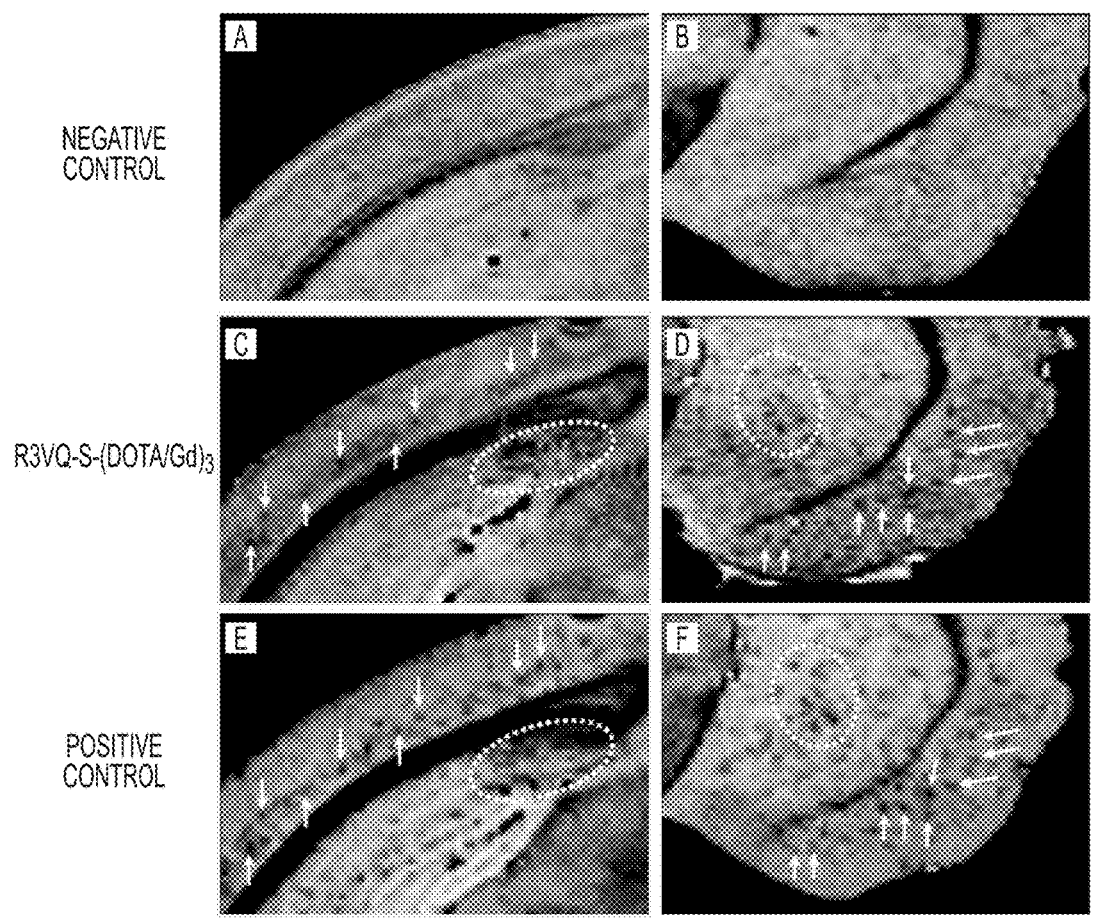

FIG. 13 shows the ex vivo MRI detection of amyloid plaques after iv injection of R3VQ-S-(DOTA/Gd)₃. Mice were iv injected with PBS (negative control, A-B) or R3VQ-S-(DOTA/Gd)₃ at 20 mg/kg (C) or 50 mg/kg (D) and sacrificed after 5 hours. MR images were acquired at 11.7 T on extracted fixed brains. Negative controls did not display strong contrast anomalies (A and B) as compared to injected brains (C and D, white arrows). These hypointense spots were stronger and more abundant at 50 mg/kg as compared to 20 mg/kg. These hypointense spots were colocalized with amyloid plaques revealed by the positive control procedure (E and F, white arrows).

FIG. 14 shows the in vitro analysis and assessment of the properties of VHH R3VQ-S-AF488 obtained by site specific conjugation. (A) HPLC/MS. (B) SDS-PAGE. (C) IEF. (D) IHC on amyloid plaques. Comparison with unconjugated protein R3VQ-SH is showed in A, B, C.

Figure 15:
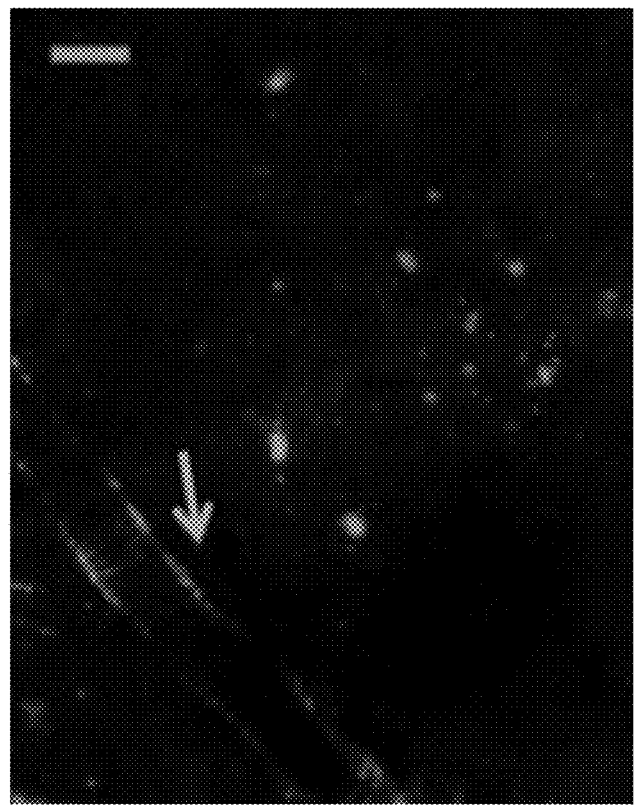

FIG. 15 shows the in vivo imaging of amyloid plaques and CAA after topic brain infusion of R3VQ-S-AF488 on the cortical surface in a 2-year-old PS2APP mouse. Arrow indicates labeling of CAA. Scale bar=50 μm.

FIG. 16 shows the in vivo imaging of R3VQ-S-AF 488 using two-photon microscopy. (A) In vivo imaging in the brain after iv injection of R3VQ-S-AF488 in a 2-year-old PS2APP mouse using a maximum intensity projection (MIP) reconstruction with a projected volume 360 μm deep from the surface of the cortex. T0 represents the baseline imaging before iv injection. The scale bar is 50 μm. Empty arrowheads indicate vascular Aβ and filled arrowheads indicate parenchymal Aβ deposits. (B) In vivo imaging in the brain after iv injection of R3VQ-S-AF488 in a 2-year-old PS2APP mouse 3.5 hours after injection. Empty arrowheads indicate vascular Aβ and filled arrowheads indicate parenchymal Aβ deposits. (C) Immunohistochemical staining of amyloid plaques in the PS2APP mouse that received iv injection of R3VQ-S-AF488 using anti-His mAb. Immunostaining of amyloid plaques by R3VQ was observed throughout the entire brain. (D) Comparison of immunostaining of amyloid plaques between iv 10 mg/kg and iv 50 mg/kg of R3VQ-S-AF488 in PS2APP mice showing a dose-dependent effect on IHC signal.

Figure 17A:
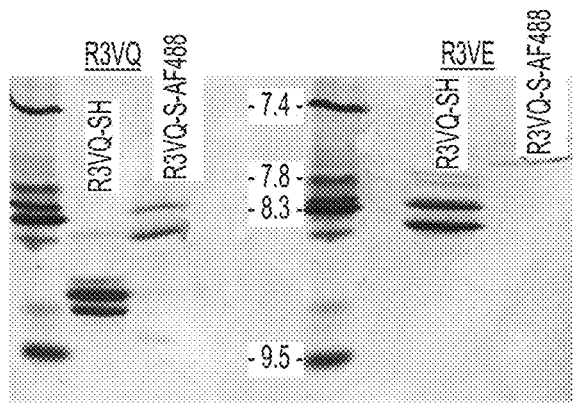
Figure 17B:
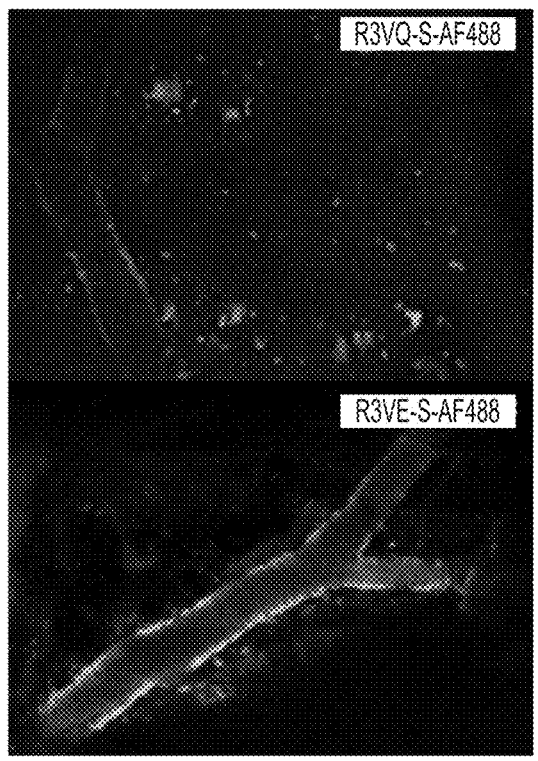
Figure 17C:
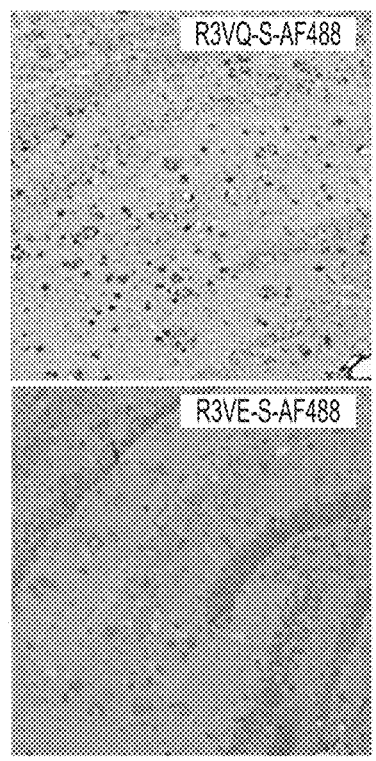

FIG. 17 shows the in vivo imaging of R3VE using two-photon microscopy: the basic pI is crucial to allow VHH to cross the BBB. (A) IEF analysis of R3VQ and R3VE compounds. R3VE is less basic than R3VQ for both VHH and conjugate (pI around 7.5 for R3VE-S-AF488). (B) Compared to mouse receiving R3VQ-S-AF488, only cerebral amyloid angiopathy was observed in the mouse receiving intravenously R3VE-S-AF488, dose: 10 mg/kg. (C) Comparison of histological staining with anti-His mAb in mice injected iv with R3VQ-S-AF488 10 mg/kg and R3VE-S-AF488 10 mg/Kg.

Figure 18:
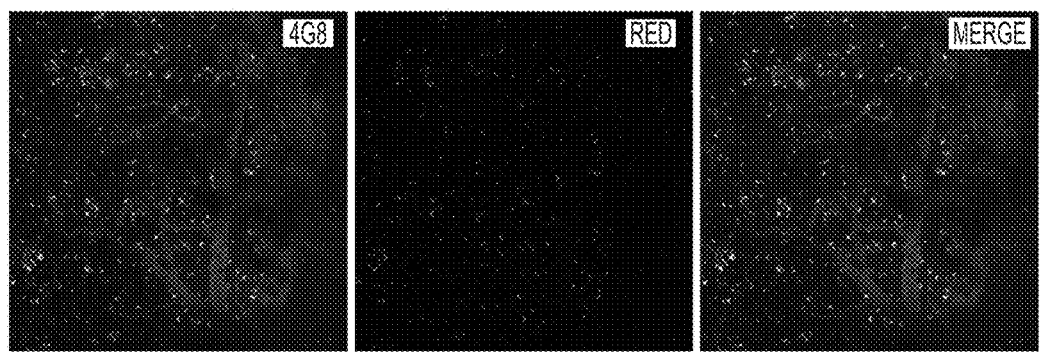

FIG. 18 shows the in vivo imaging in the brain after iv injection of mAb 4G8-AF488 (10 mg/Kg) in a 2-year-old PS2APP mouse. The presence of mAb 4G8 is only observed in the blood vessels. Extra-vascular signal is artefactual because it is also observed in the reference channel (red).

EXAMPLE 1

Generation of Anti-Abeta VHHs Coupled to Gadolinium Contrast Agent and their Evaluation In Vitro/In Vivo Materials and Methods
1. Production, Selection and Purification of VHH R3VQ
Antigen Preparation and Induction of a Humoral Immune Response in Alpaca A-beta 42 peptide (Aβ42) (1 mg-Bachem) was dissolved in 900 μl H₂O and vortexed. 100 μl PBS 10× was added and the mixture was incubated at room temperature for one month before use. 250 μl of the mixture was mixed with 250 μl of Freund complete adjuvant for the first immunization, and with 250 μl of Freund incomplete adjuvant for the following immunizations. One young adult male alpaca (*Lama pacos*) was immunized at days 0, 21 and 35 with 250 μg immunogen. At day 50 a serum sample was taken and the immune response monitored by ELISA using Aβ42 as antigen.

Library Construction and Panning 250 ml of blood of the immunized animal was collected at day 50 and the peripheral blood lymphocytes isolated by centrifugation on a Ficoll (Pharmacia) discontinuous gradient and stored at −80° C. until further use. Total RNA and cDNA was obtained as previously described in Lafaye P. et al. (1995, Res Immunol., 146:373-382), and DNA fragments encoding VHH domains amplified by PCR using CH2FORTA4 and VHBACKA6 primers, which anneal to the 3' and 5' flanking region of the VH genes, respectively. The amplified product was used as template in a second round of PCR using either the primers VHBACKA4 and VHFOR36 or the primers VHBACKA4 and LHH (5' GGACTAGTTGCGGCCGCTGGTTGTGGTTTTGGT-GTCTTGGG-3') (SEQ ID NO. 13) specific for the long hinge homodimeric antibody. The primers were complementary to the 5' and 3' ends of the amplified product and incorporated SfiI and NotI restriction sites at the ends of the VHH genes. The PCR products were digested and ligated into phage expression vector pHEN1. The resulting library was composed of two sub-libraries, one derived from VHH DNA-encoding genes with no hinge and the other from long hinge antibody genes. Phages were produced and isolated using both sub-libraries, and subsequently pooled.

The library was panned for reactivity in parallel with a biotinylated Aβ1-42, Aβ1-40 or Aβ1-16 peptide, as previously described (Lafaye P. et al., 2009, Mol Immunol. 46:695-704). The library ($10^{13}$ transducing units) was panned by incubation with each biotinylated peptide for 1 h at 37° C. under gentle agitation, then the mixture was incubated with streptavidin beads for 15' at 37° C. A different blocking agent was used at each of the three rounds of panning: 2% skimmed milk, Licor diluted 1:4, and 4% BSA were respectively used. The concentration of biotinylated peptides used decreased at every round of panning with respectively 100 nM, 50 nM and 10 nM. Phage clones were screened by standard ELISA procedures using a HRP/anti-M13 monoclonal antibody conjugate (GE Healthcare) for detection (see below).

Expression of VHHs

The coding sequence of the selected nanobodies in vector pHEN1 was sub-cloned into a modified bacterial expression vector pET23 containing a 6-Histidine tag using NcoI and NotI restriction sites. Transformed *E. coli* BL21 (DE3) LysS cells express VHH in the cytoplasm after overnight induction with IPTG (0.5 mM) at 16° C. Purified VHHs were isolated by IMAC from cytoplasmic extracts using a HiTrap crude column charged with $Ni^{2+}$ (GE Healthcare), according to the manufacturer's instructions, followed by size exclusion chromatography with a Superdex 75 column (GE Healthcare). The VHHs (in particular the R3VQ(His)-$NH_2$; compound 1 in FIG. 9) were eluted in 50 mM sodium phosphate buffer, 300 mM NaCl and 500 mM imidazole buffer.

2. Characterization of Biochemical Properties of VHH R3VQ

Immunoblots

A-beta 42 peptide was resuspended in NuPAGE® LDS sample buffer (Invitrogen) containing 8M urea. Following separation by polyacrylamide gel electrophoresis (PAGE) using NuPAGE Novex 4-12% Bis-tris gel (Invitrogen), semi-dry transfer onto Hybond-C (Amersham) and western blotting were carried out using the Xcell II blot module (Invitrogen). Prior to the immunochemical reaction, membranes were blocked in a 4% skimmed milk solution. Immunoblotting of membranes was accomplished with VHH and revealed by rabbit anti-His tag (eBioscience) polyclonal antibodies followed by peroxidase labeled goat anti-rabbit immunoglobulins (Abcam). Finally, peroxidase activity was visualized using a chemiluminescent kit (GE Healthcare).

ELISA

Streptavidin-coated microtiter plates (Thermo Scientific, Denmark) were coated by incubation overnight at 4° C. with 1 µg/ml of biotinylated A-beta 40 or A-beta 42 (preferably A-beta 40) diluted in PBS. Plates were washed with buffer 0.1% Tween 20 in PBS. VHH R3VQ was diluted in buffer 0.5% gelatin 0.1% Tween 20 in PBS. After 2 h incubation at 37° C., plates were washed again before adding respectively a rabbit anti-His tag polyclonal antibody (eBiosciences), followed by peroxidase labeled goat anti-rabbit immunoglobulins (Abcam), and finally revealed by OPD (o-phenylendiamine dihydrochloride, Dako) according to manufacturer's protocol.

Determination of Dissociation Constants by ELISA

The binding affinity of VHHs was determined as previously described (Friguet B. et al., 1985, Immunol Methods, 77:305-19). Briefly, various concentrations of Aβ peptides (A13 fragments 1-16, 10-20, 15-25, 22-35 and 29-40) were incubated in solution overnight at 4° C. with a known quantity of VHH until equilibrium was reached. The VHH concentration used was determined by preliminary ELISA calibrations. Each mixture (100 µl) was transferred to a well of a microtiter plate previously coated with antigen and was incubated for 20 min at 4° C. The plates were washed with buffer 0.1% Tween 20 in PBS and bound VHHs were detected by adding beta-galactosidase-conjugated goat anti-rabbit Igs (Biosys, Compiegne, France) and 4-methylumbelliferyl α-D galactoside (Sigma). Fluorescence was read (Fluoroskan, Labsystem, Finland) at 460 nm, after excitation at 355 nm. KD was estimated from the slope of the regression curve obtained by plotting the reciprocal of the fraction of bound antibody versus the reciprocal of the molar concentration of antigen.

Sequences Analysis

VHH encoded DNAs were sequenced by GATC Biotech and sequences were treated with DNA strider.

Determination of pI

The pI of VHHs was determined by isoelectric focusing using IEF 2-9 Gel (Invitrogen). NEPGHE (non equilibrium pH gradient gel electrophoresis) with sample application at the anode was used because it allows optimal protein analysis in the basic range of the gel including pH 8.5 to 10.5. The protocol was detailed in SERVAGel IEF 3-10 instruction manual.

3. VHH R3VQ Coupling to MRI Contrast Agents and Characterization of the MRI Properties of the Synthesized Contrast Agents VHH R3VQ was conjugated to gadolinium (MRI contrast agent) with 1,4,7,10-tetraazacyclododecane-1,4,7,10-tetraacetic acid (DOTA) (chelating agent). Two strategies based on non-site specific and site specific coupling were used:

The first strategy comprises the steps of (i) conjugation with the chelating agent DOTA to lysine residues of VHH (R3VQ-$NH_2$ 1), and (ii) subsequent chelation with a MRI contrast agent, i.e. gadolinium (Gd) (see FIG. 9A). It resulted in complex polydisperse mixture of conjugates R3VQ-N-(DOTA/Gd)$_n$ 2 with randomly distributed Gd and a range of Gd:VHH stoichiometry, as shown by reverse-phase high performance liquid chromatography/mass spectrometry (RP-HPLC/MS). By varying the conditions of the DOTA conjugation step, several conjugates were prepared with different DOTA/Gd density (overall yield 60-67%). When assessed in vivo by IHC and MRI, the R3VQ-N-(DOTA/Gd)$_n$ conjugate was able to recognize amyloid plaques in mouse after intra cerebro-ventricular injection.

The second strategy was to use a site specific approach which involves the labeling of the VHH R3VQ with a maleimido compound (see FIG. 9B). Cys-engineered R3VQ (R3VQ-SH 3) containing from the N to the C terminus a 6-Histidine tag, a thrombin cleavage site, R3VQ VHH sequence followed by a $G_3S$ spacer and three extra amino acids CSA was cloned in vector pET23 to allow a high level of expression. The single domain products were shown to be pure to homogeneity by SDS-PAGE and by RP-HPLC/MS. The pI value of R3VQ-SH was in the range 8.5-9. A maleimido-(DOTA/Gd)$_3$ compound 4 was prepared by solid-phase peptide synthesis using 9-fluorenylmethoxycarbonyl (Fmoc) chemistry. When conjugated to maleimido-(DOTA/Gd)$_3$ compound by thio-addition, R3VQ-SH was totally converted into the well-defined compound R3VQ-S-(DOTA/Gd)$_3$ 5, as shown by RP-HPLC/MS, with 70% yield. The pI of R3VQ-S-(DOTA/Gd)$_3$ was slightly reduced compared to the one of the unlabeled R3VQ-SH. The binding characteristics of R3VQ-SH and R3VQ-S-(DOTA/Gd)$_3$ were determined in competitive inhibition experiments involving Aβ40 bound to the ELISA plate and soluble Aβ40. The concentration of Aβ40 giving 50% binding inhibition was calculated to be 1 µg/ml for both R3VQ-SH and R3VQ-S-(DOTA/Gd)$_3$ suggesting that the addition of DOTA/Gd does not affect the VHH binding properties. Further, following the distribution of VHH-specific immunoreactivity in transgenic B6 PS2APP mice, R3VQ-SH showed good ability to immunodetect Aβ plaques in mouse paraffin sections after antigen retrieval pretreatment.

3.1. General Synthesis Methods

Unless otherwise specified, the amino-acid derivatives and the reagents are purchased from Novabiochem and Sigma-Aldrich, respectively. The concentration of the peptide and VHH solutions (net protein content) was determined by quantitative amino acid analysis (AAA) using a Beckman 6300 analyser after hydrolysis of the compounds with 6N HCl at 110° C. for 20 h. The RP-HPLC/MS analyses were performed on an Alliance 2695 system coupled to a UV detector 2487 (220 nm) and to a Q-Tof-micro™ spectrometer (Micromass) with an electrospray ionisation (positive mode) source (Waters). The samples were cooled to 4° C. on the autosampler. The linear gradient was performed with acetonitrile+0.025% formic acid (A)/water+0.04% TFA+0.05% formic acid (B) over 10 or 20 min. The column used was a XBridge™ BEH300 C18 (3.5 µm, 2.1×100 mm) (Waters) (gradient 10-100% A). The source temperature was maintained at 120° C. and the desolvation temperature at 400° C. The cone voltage was 40 V. The samples were injected at 0.4-1 mg/ml concentration in their respective buffer added with B. The expected Mr values correspond to the average mass of proteins with N-ter deleted Met and one disulfide bond. The Mr analyses were recorded on the same spectrometer in the positive mode by direct infusion (source temperature and desolvation temperature were maintained at 80° C. and 250° C., respectively). The samples were dissolved at 5 µM concentration in water/acetonitrile (1/1) with 0.1% formic acid. The purity of 4 was analyzed by RP-HPLC using an Agilent 1200 pump system with a UV detector at 220 nm. The column used was a Kromasil C18 (100 Å, 5 µm, 4.6×250 mm) (AIT) and the gradient was performed with acetonitrile (VWR) (C)/water+0.1% TFA (VWR) (D) over 20 min.

3.2. Non-Site Specific Approach

The molar equivalents of all reagents are indicated relative to reactive groups (5 NH$_2$ per R3VQ and an average of 1 DOTA/R3VQ conjugate). The overall yields (see Table 2 below) include all the synthetic steps from the starting protein 1 in the affinity column elution buffer. They were calculated by dividing the actual amount of the final products 2a-f by their expected amount (net protein contents).

The R3VQ(His)-NH$_2$ VHH 1 eluted from the affinity column was dialyzed in PBS buffer containing 300 mM NaCl (PBS/NaCl). 1,4,7,10-Tetraazacyclododecane-1,4,7,10-tetraacetic acid mono (N-hydroxysuccinimide ester) (DOTA-NHS) (274 µg, 4 eq relative to amino groups) dissolved in PBS/NaCl (120 µl) was added to 1 (480 µl, 0.60 mg/ml) and the solution was stirred at room temperature. Aliquots (10 µl) were withdrawn every 15 min, diluted with 100 mM Tris buffer pH 7.3 (90 µl) and analyzed by HPLC/MS to monitor the reaction progress. After 3 h, the solution was cooled to 4° C. and the buffer was exchanged to 0.4M Na acetate buffer pH 5 by using Vivaspin 500 centrifugal filter device (3,000 MWCO PES) (Sartorius). The resulting DOTA-VHH conjugate (480 µl) was added with GdCl$_3$ (149 µg, 45 eq relative to average DOTA groups) in the same buffer (5 µl). The solution was stirred at room temperature for 2.5 h. The buffer was exchanged to PBS/NaCl at 4° C. with the same Vivaspin device as above and the solution was concentrated to afford the R3VQ(His)-N-(DOTA/Gd)$_{0-2}$ conjugate 2f (105 µl, 1.48 mg/ml). The overall yield is 67%.

The conjugate 2e was obtained using the same protocole except that DOTA-NHS was added to 1 portionwise (0.5 eq every 45 min, total of 5.5 eq relative to amino groups). The solution was stirred at room temperature for 8 h15. The overall yield is 60%.

R3VQ(His)-NH$_2$ 1

AAA: Ala 15.8 (16), Arg 9.1 (9), Asp+Asn 13.4 (13), Glu+Gln 16.0 (15), Gly 13.4 (14), His 5.7 (7), Ile 3.1 (3), Leu 8.4 (8), Lys 4.1 (4), Phe 4 (4), Pro 6.1 (7), Ser 11.3 (13), Thr 10.0 (11), Tyr 4.8 (5), Val 11.1 (11).

MS: 15753.0996 ($C_{681}H_{1053}N_{209}O_{216}S_4$ calcd 15752.3949)

R3VQ(His)-N-(DOTA/Gd)$_{0-2}$ 2f

AAA: Ala 16.0 (16), Arg 10.0 (9), Asp+Asn 12.8 (13), Glu+Gln 15.0 (15), Gly 13.8 (14), His 6.7 (7), Ile 3.0 (3), Leu 8.2 (8), Lys 4.5 (4), Phe 4 (4), Pro 8.5 (7), Ser 10.5 (13), Thr 10.1 (11), Tyr 4.8 (5), Val 11.1 (11).

MS: 16293.1328 ((DOTA/Gd)$_1$: $C_{697}H_{1076}N_{213}O_{223}S_4Gd$ calcd 16293.0263)

16833.5586 ((DOTA/Gd)$_2$: $C_{713}H_{1099}N_{217}O_{230}S_4Gd_2$ calcd 16833.6576)

3.3. Site Specific Approach

Production of R3VQ-SH 3

The coding sequence of a Cys-engineered VHH (R3VQ-SH 3) was cloned into a modified bacterial expression vector pET23 using NcoI and XhoI restriction sites. Transformed E. coli BL21 (DE3) pLysS cells express 3 in the cytoplasm after overnight induction with IPTG (0.5 mM) at 16° C. Purified VHHs were isolated by IMAC from cytoplasmic extracts using a HiTrap crude column charged with Ni$^{2+}$ (GE Healthcare), according to manufacturer's instructions. 3 was eluted in PBS/NaCl containing 500 mM imidazole.

AAA: Ala 16.1 (16), Arg 10.2 (10), Asp+Asn 13.6 (13), Glu+Gln 11.9 (11), Gly 19.1 (20), His 6.0 (7), Ile 3.1 (3), Leu 8.5 (8), Lys 2.2 (2), Phe 4 (4), Pro 4.3 (4), Ser 15.5 (18), Thr 9.5 (10), Tyr 4.8 (5), Val 12.9 (12).

MS: 15723.4268 ($C_{671}H_{1041}N_{213}O_{217}S_5$ calcd 15724.2820).

Synthesis of maleimido-(DOTA/Gd)$_3$ 4

The synthesis of 4 was performed stepwise on solid-phase from Fmoc-Gly-Wang resin (143 mg, 0.093 mmol). The building blocks 1,4,7,10-tetraazacyclododecane-1,4,7-tris-tbutyl-acetate-10-(N-α-Fmoc-N-ε-acetamido-L-lysine) [Fmoc-Lys(DOTA(OtBu)$_3$))—OH] (1.1 eq) (Macrocyclics) and 6-maleimidohexanoic acid (3 eq) were incorporated manually using 2-(1H-9-azabenzotriazole-1-yl)-1,1,3,3-tetramethyluronium hexafluorophosphate (HATU) (1.06 and 2.9 eq, respectively)/diisopropylethylamine (DIEA) (2.2 and 6 eq, respectively) as coupling reagents and dimethylformamide (DMF) (Applied Biosystems) as solvent. Fmoc-Gly-OH (3 eq) was incorporated with DIC (3 eq) in DMF. The coupling steps with the Lys, Gly and maleimido derivatives were monitored by the Kaiser test (E. Kaiser et al (1980) *Anal. Biochem.* 34, 595-598) and were completed in, respectively, 3 h, 2 h and 1 h. Fmoc protection was removed with 20% piperidine in DMF. After the third lysine derivative, the last coupling with 6-maleimidohexanoic acid was carried out on three-quarters of the product (0.07 mmol). The peptide-resin was suspended in 10 ml of TFA (Applied Biosystems)/water/triisopropylsilane (95/2.5/2.5 v/v/v) at 4° C. and stirred for 4 h at RT. After filtration of the resin, the solution was concentrated and the crude product precipitated with diethyl ether. After centrifugation, the pellet was dissolved in water and lyophilized to yield 119 mg of the crude DOTA-peptide which was analyzed by NMR, MS, and RP-HPLC (gradient 10-40% C, retention time 9.2 min).

$^1$H NMR (D$_2$O): δ 6.69 (s, 2H, CH Mal), 4.18 (m, 2H, 2CH$_\alpha$), 4.08 (m, 1H, CH$_\alpha$), 3.87-3.78 (m, 6H, CH$_2$ Gly), 3.74-3.48 (b, 24H, CH$_2$CO DOTA), 3.34 (t, 2H, CH$_2$ 6-Mal, J$_{5,6}$=0.017 Hz), 3.30-2.99 (b, 48H, CH$_2$CH$_2$N DOTA), 3.06 (b, 6H, CH$_{2\epsilon}$), 2.14 (m, 2H, CH$_2$ 2-Mal), 1.74-1.53 (m, 6H, CH$_{2\beta}$), 1.49-1.34 (m, 10H, CH$_{2\delta}$, CH$_2$ 3-Mal, CH$_2$ 5-Mal), 1.29-1.18 (m, 6H, CH$_{2\gamma}$), 1.16-1.06 (m, 2H, CH$_2$ 4-Mal).

$^{13}$C NMR (D$_2$O): δ 177.11 (1C, CONH Mal), 175.15, 174.63, 174.36 (3C, CO Lys), 173.26 (2C, CO Mal), 172.93 (1C, COOH Gly), 171.48, 171.21 (2C, CO Gly), 163.04-162.68 (4C, CONH DOTA), 134.22 (2C, CH Mal), 120.59, 117.69, 114.79, 111.90 (TFA), 55.20-53.10 (12C, CH$_2$CO DOTA), 54.04, 53.80, 53.47 (3C, CH$_\alpha$), 52.20-46.80 (24C, CH$_2$CH$_2$N DOTA), 42.38, 41.00 (3C, CH$_2$ Gly), 39.10 (3C, CH$_{2\epsilon}$), 37.37 (1C, CH$_2$ 6-Mal), 35.04 (1C, CH$_2$ 2-Mal), 30.48, 30.24, 30.23 (3C, CH$_{2\beta}$), 27.67, 27.33, 24.67 (3C, CH$_2$ 3-Mal, CH$_2$ 5-Mal, CH$_{2\delta}$), 25.43 (1C, CH$_2$ 4-Mal), 22.43, 22.33, 22.15 (3C, CH$_{2\gamma}$).

MS: [M+H]$^+$ 1925.9888, [M+K]$^+$ 1963.9391 (C$_{82}$H$_{136}$N$_{22}$O$_{31}$ calcd [M+H]$^+$ 1927.1195, [M+H]$^+$ 1965.2098).

The DOTA-peptide intermediate (99 mg) was dissolved in 0.4M Na acetate buffer pH 5 (41 ml) and added with Gd(OAc)$_3$.xH$_2$O (123 mg, 2 eq relative to DOTA). After stirring at 95° C. for 25 min, the solution was cooled and loaded on a C18 reverse-phase column (2 g, diameter 1.5 cm). The column was washed with four volumes of water and the product was eluted with three volumes of water/acetonitrile 1/1 affording 79 mg of product after lyophilisation. The crude DOTA/Gd peptide was purified by reverse-phase flash chromatography (30×200 mm) using a gradient with acetonitrile+0.1% TFA/buffer D over 40 min, from 5/95 to 35/65 (20 ml/min, retention time 18 min). After lyophilization of the main fraction, 61 mg of 4 were obtained with an overall yield of 44% (the overall yield includes all the synthetic steps, it was calculated on the net peptide content of the isolated product 4 based on the first Gly residue loading on the resin). 4 was analyzed by MS and RP-HPLC (gradient 5-35% C, retention time 12.2 min, purity>90%).

MS: 2388.8889 (C$_{82}$H$_{127}$N$_{22}$O$_{31}$Gd$_3$ calcd 2388.7901).

Synthesis of R3VQ-S-(DOTA/Gd)$_3$ 5

The R3VQ-SH VHH 3 eluted from the affinity column was dialyzed in PBS buffer containing 300 mM NaCl (PBS/NaCl). 4 (1.35 mg, 3 eq relative to 1 thiol group per VHH) in aqueous solution (135 µl) was added to 3 (1.5 ml, 2 mg/ml in PBS/NaCl pH 6.8) and the solution was stirred at 4° C. for 3 h. The solution was then diafiltered using Vivaspin 2000 centrifugal filter device (3,000 MWCO PES) (Sartorius). Aliquots (20 µl) of 3 and 5 were diluted with buffer B (20 µl) for RP-HPLC/MS analyses. Moreover, aliquots (10 µl) of 3 and 5 were diluted in 100 mM Tris buffer pH 7.3 (90 µl) for ELISA analyses. 1 ml of 5 (2.36 mg/ml) was obtained with a yield of 70%. It was calculated by dividing the actual amount of the final product 5 by its expected amount (net protein contents).

The same reaction was also performed directly in the affinity column elution buffer (PBS/NaCl containing 500 mM imidazole), and gave a 83% overall yield. The process for obtaining the R3VQ/Gd conjugates is thus improved when the conjugation is directly performed in the affinity column elution buffer (PBS/NaCl/Imidazole)): i) the number of steps is decreased to two, and ii) the overall yield is increased until 83%. This process improvement has also been validated with another VHH (data not shown).

AAA: Ala 14.9 (16), Arg 10.2 (10), Asp+Asn 12.2 (13), Glu+Gln 11.1 (11), Gly 24.6 (23), His* (7), Ile 3.1 (3), Leu 8.5 (8), Lys 11.7* (5), Phe 4 (4), Pro 4.8 (4), Ser 14.9 (18), Thr 9.1 (10), Tyr 5.0 (5), Val 12.6 (12). [*His cannot be determined due to co-elution with ammonium. Lys is overestimated due to co-elution with maleimido derivative in the conditions of the analysis.]

MS: 18113.7383 (C$_{753}$H$_{1168}$N$_{235}$O$_{248}$S$_5$Gd$_3$ calcd 18113.0720).

SDS-PAGE Electrophoresis

Polyacrylamide Gel electrophoresis (PAGE) was performed using NuPAGE Novex 4-12% Bis-Tris gel (Invitrogen) according to manufacturer's instructions.

Determination of pI

The pI of VHHs was determined by isoelectric focusing using IEF 2-9 Gel (Invitrogen). NEPGHE (non equilibrium pH gradient gel electrophoresis) with sample application at the anode was used because it allows optimal protein analysis in the basic range of the gel including pH 8.5 to 10.5. The protocol was detailed in SERVAGel IEF 3-10 instruction manual.

ELISA

Streptavidin-coated microtiter plates (Thermo Scientific, Denmark) were coated by incubation overnight at 4° C. with 1 µg/ml of biotinylated A-beta 40 or A-beta 42 (preferably A-beta 40) diluted in PBS. Plates were washed with buffer 0.1% Tween 20 in PBS. For the non-site specific strategy, R3VQ-NH$_2$ 1, R3VQ-N-(DOTA/Gd)$_{1-2}$ 2e were diluted in buffer 0.5% gelatin 0.1% Tween 20 in PBS. After 2 h incubation at 37° C., plates were washed again before adding respectively a rabbit anti-His tag polyclonal antibody (eBiosciences), followed by peroxidase labeled goat anti-rabbit immunoglobulins (Abcam), and finally revealed by OPD (o-phenylendiamine dihydrochloride, Dako) according to manufacturer's protocol. For the site specific strategy, R3VQ-SH 3 and R3VQ-S-(DOTA/Gd)$_3$ 5 were diluted in the same buffer as described before, after incubation with biotinylated A-beta 40 or A-beta 42 (preferably A-beta 40), a monoclonal anti-His tag antibody (H1029—Sigma) was added, followed by peroxidase labeled goat anti-mouse antibody (ab97265-Abcam), and revealed by the same substrate.

Affinity Determination

The binding properties of 3 and 5 were determined by measuring the amount of soluble A-beta 40 or A-beta 42 (preferably A-beta 40) peptide able to give 50% inhibition of immobilized A-beta 40 or A-beta 42 (preferably A-beta 40) recognition. Briefly, various concentrations of A-beta 40 or A-beta 42 (preferably A-beta 40) were incubated overnight at 4° C. with a defined quantity of 3 or 5 until equilibrium was reached. The VHH concentration used has been deduced from preliminary ELISA calibrations. Each mixture (100 µl) was transferred to a well of microtiter plate previously coated with antigen and was incubated for 15 min at 4° C. After washing with PBS containing 0.1% Tween 20, unbound VHH were detected by the addition of an anti-His mAb (H1029-Sigma) followed by β-galactosidase goat anti-mouse Igs and 4-methylumbelliferyl β-D-galactoside. Fluorescence was read (Fluoroskan, Labsystem, Finland) at 460 nm, after excitation at 355 nm.

Immunohistochemistry

Immunohistochemistry was performed on paraffin coronal brain sections (5 μm in thickness), obtained from transgenic mouse models of amyloidosis (PS2APP mice). The sections were made with a microtome (Microm HM340E). Sections were de-paraffinized in xylene (5 min, 3 times), rehydrated through ethanol (100%×2, 90 and 70%; 5 min/step) and brought to water. They were then pretreated with 98% formic acid for 5 min and finally immersed in water for 5 min. Endogenous peroxidases were neutralized with 3% hydrogen peroxide and 20% methanol, and nonspecific binding sites were blocked with TBS-0.5% tween pH8 BSA 2% for 30 min. In the following steps, the sections were rinsed 3 times, 5 min/time in TBS-tween between steps. The sections were then incubated overnight at 4° C. with the primary antibody R3VQ-SH, diluted to 2 μg/ml in TBS-tween. Sections were then treated with mouse monoclonal anti-His-tag antibodies (H1029-Sigma) for 2 h at room temperature, and finally developed with Dako REAL™ system Peroxidase/DAB Kit (Glostrup, Denmark) according to manufacturer's protocol. After washing with water, sections were counter-stained with Harris hematoxylin and re-rinsed in water. Before being mounted, sections were dehydrated in graded ethanol solution (70, 90 and 100%) and cleared in xylene.

3.4. MRI Properties of the Synthesized Contrast Agents

MRI properties of the contrast agents were assessed on a 7 T-Spectrometer (Agilent, USA) interfaced with a console running VnmrJ 2.3. The spectrometer was equipped with a rodent gradient insert of 700 mT/m. A quadrature birdcage coil (diameter: 23 mm) was used for emission and reception. The longitudinal and transverse relaxivities r1 and r2 (change in the relaxation rate per unit concentration of an agent, meaning "effectiveness" as a MRI contrast agent) were determined from linear fits of R1 (i.e. 1/T1) and R2 (i.e. 1/T2) as a function of contrast agent concentration for concentrations of 0.2, 0.15, 0.1, 0.05, 0.025, 0.01, and 0 mmol/l by using the following equations: R1(C)=R1(0)+r1×C where R1(C) is the R1 in the tubes containing the contrast agent at a concentration C, R1(0) is the R1 in the tube without the contrast agent, and C is the concentration of the contrast agent. R2(C)=R2(0)+r2×C was used to calculate r2. The samples were imaged in hematocrit tubes.

T1 calculation was based on seven successive 2D multi-slice spin echo images with twenty TR values (TR=0.021, 0.04, 0.06, 0.08, 0.1, 0.15, 0.2, 0.3, 0.4, 0.5, 0.6, 0.7, 0.8, 0.9, 1, 1.5, 2, 3, 4, 5 sec), TE=14 ms, Nex=4, FOV=10×10 mm2, Mtx=64×64, 1 slices, slice thickness=3 mm, bandwidth=50 kHz). Parametric maps of relaxation times were calculated from exponential regression curves (S=1−exp(−TR/T1)) where S is the signal intensity, TR is the repetition time and T1 is the longitudinal relaxation time (ImageJ, MRI Analysis Calculator, Karl Schmidt).

T2 calculation were based on 2D multi-echo multi-slice spin echo images by using 16 Echo times (TE=10 to 160 msec); TR=3300 ms; Nex=2; bandwidth=100 kHz, FOV=10×10 mm2, Mtx=64×64, 1 slices, slice thickness=3 mm. Parametric maps of relaxation times were calculated from exponential regression curves (S=exp(−TE/T2)) where S is the signal intensity, TE is the echo time and T2 is the longitudinal relaxation time (ImageJ, MRI Analysis Calculator, Karl Schmidt).

4. In Vitro Characterization of VHH R3VQ, and VHH R3VQ Conjugates by Immunohistochemistry, Biochemistry and In-Vitro MRI Subjects Human cortical brain tissues from AD patients (Braak stage V and VI) were obtained from the NeuroCEB brain bank. This bank is associated to a brain donation program run by a consortium of patients associations (including France Alzheimer Association) and declared to the Ministry of Research and Universities, as requested by French Law. An explicit written consent was obtained for the brain donation in accordance with the French Bioethical Laws.

Preclinical experiments were performed on B6TgPS2APP (Richards J. G., 2003, J Neurosci., 23:8989-9003) and APP/PS1dE9 (Garcia-Alloza M., 2006, Neurobiol Dis., 24:516-24) transgenic mice. Animal experimental procedures were performed in strict accordance with the recommendations of the EEC (86/609/EEC) and the French national committee (decree 87/848) for the care and use of laboratory animals. The animals were sacrificed using a high dose of sodium pentobarbital (100 mg/kg) and then perfusion-fixed with 10% buffered formalin. Their brains were then removed, immersed in formalin for at least 24 hours and stored at 4° C.

Tissue Extracts

Tissue extraction was performed according to Gong, Y. et al. (2003, Proc Natl Acad Sci USA, 100:10417-10422). Frontal cortex from AD brain (0.2 g) was homogenized in 20 volumes of phenol red-free Ham's F12 medium (Gibco) or buffer A (PBS, pH 7.4, 0.32 M sucrose, 50 mM Hepes, 25 mM MgCl2, 0.5 mM DTT) containing protease inhibitors (200 μg/ml PMSF, 2 μg/ml pepstatin A, 4 μg/ml leupeptin, 30 μg/ml benzamidine hydrochloride), and was centrifuged at 100,000×g for 1 h. The pellet was re-homogenized in 10 volumes of phenol red-free Ham's F12 medium or buffer A plus protease inhibitors and was re-centrifuged. The protein concentration of the combined supernatants was determined. An aliquot of protein was then concentrated to a volume of 60 μl or less, by using a Centricon-10 concentrator.

Immunoblots

Brain extracts or A-beta 42 peptide were resuspended in NuPAGE® LDS sample buffer (Invitrogen) containing 8M urea. Following separation by polyacrylamide gel electrophoresis (PAGE) using NuPAGE Novex 4-12% Bis-tris gel (Invitrogen), semi-dry transfer onto Hybond-C (Amersham) and western blotting were carried out using the Xcell II blot module (Invitrogen). Prior to the immunochemical reaction, membranes were blocked in a 4% skimmed milk solution. Immunoblotting of membranes was accomplished with VHH and revealed by rabbit anti-His tag (eBioscience) polyclonal antibodies followed by peroxidase labeled goat anti-rabbit immunoglobulins (Abeam). Finally, peroxidase activity was visualized using a chemiluminescent kit (GE Healthcare).

Immunohistochemistry

Immunohistochemistry was performed on fixed tissues (paraffin-embedded or frozen sections), or alternatively on unfixed fresh tissues (frozen sections). Standard IHC protocols were applied and adapted for each tissue conditions. As most of immunostaining experiments were performed using paraffin sections, a detailed protocol for paraffin-embedded material is presented here. Immunostaining of brain tissue was performed on 4 μm thick paraffin sections. Both human and mouse tissues were used (Human AD patient, TauPS2APP mice [Grueninger F. et al., 2010, Neurobiol Dis., 37:294-306] and PS2APP transgenic mice [Richards, J. G., et al 2003, The Journal of neuroscience 23, 8989-9003]). Sections were de-paraffinized in xylene, rehydrated through ethanol (100%, 90%, and 70%), 5 min for each solution and finally brought to running tap water for 10 min. They were then incubated in 98% formic acid for 5 min, washed again under running tap water, quenched for endogenous peroxidase with 3% hydrogen peroxide and 20% methanol, and finally washed in water. Non-specific binding was blocked by incubating the sections for 30 min in 2% bovine serum albumin in TBS+0.5% Tween. Appropriate dilutions of primary antibodies (5-10 μg/ml of VHH His or Strep tag) were then applied and slices incubated overnight in a humidified chamber at room temperature. Slides were washed with TBS-Tween and incubated with secondary antibodies rabbit anti-His Tag for 1/1000 or home-made biotinylated anti-strep mAb C23-21 in TBS-Tween at room temperature for 1 h. Slides were then incubated with reagents of Dako REAL™ Detection System, Peroxidase/DAB+ according to manufacturer's instructions. Chromogenic (DAB) revelation was developed until a good signal-to-noise ratio was obtained (about 5 min). After washing with TBS-Tween, slides were counter-stained with hematoxylin. For labeling of plaques, biotinylated 4G8 (Wisniewski T et al., 1996, B. Biochem J., 313:575-80) mAb (1/10000) or 6F/3D (Akiyama H. et al., 1996, Neurosci let., 206:169-72) mAb (1/200) was used as a positive control in parallel.

In vitro MRI

MRI were performed on the brains of B6TgPS2APP (Richards J. G., 2003, J Neurosci., 23:8989-9003) and APP/PS1dE9 (Garcia-Alloza M., 2006, Neurobiol Dis., 24:516-24) transgenic mice (n=2, females). MRI were recorded on a 7 T-Spectrometer (Agilent, USA) interfaced with a console running VnmrJ 2.3. The spectrometer was equipped with a rodent gradient insert of 700 mT/m. A birdcage coil (RapidBiomed, GmbH, Germany) and a mouse brain surface coil (RapidBiomed GmbH, Germany) were used for emission and reception, respectively.

After 4 h of membranes permeabilization in a solution of Triton 0.2% in PBS, the brain samples were soaked in a solution of phosphate buffered saline (PBS) and tested contrast agent and stored at 4° C. for at least 24 hours prior to imaging. For scanning, the brains were placed in a tight plastic tube filled with Fluorinert® (3M, Cergy-Pontoise, France), an aprotonic perfluorocarbon-based fluid that provides a black background in MR images.

MR images were based on a 3D gradient-echo sequence was used (FLASH) to acquire T2*w images (TR=40 ms, TE=15 ms, FA=20°, Bw=50 kHz, Nex=16, matrix=512× 512×128, FOV=13×13×13 mm², yielding a resolution of 25×25×100 μm³ for a total Tacq of 11 h 39 min).

Gd-Staining Method: A Gold Standard Method for Amyloid Plaques Detection

This procedure was used to make colocalization between hypointense spots seen on MR images after the in vitro procedure, and a gold standard method revealing amyloid plaques (Petiet A. et al., 2012, Neurobiol Aging, 33:1533-44). Briefly, following in vitro experiments, the samples were soaked in a solution of PBS and 0.5 M gadoterate meglumine at a dilution of 1:200 (2.5 mM) and stored at 4° C. for at least 24 hours prior to imaging. MR images were realized in the same conditions as used for in vitro experiments.

5. In-Vivo Evaluation of VHH R3VQ, and VHH R3VQ Conjugates

Subjects

In vivo evaluation of VHH R3VQ, and VHH R3VQ conjugates was performed on TauPS2APP (Grueninger F. et al., 2010, Neurobiol Dis., 37:294-306) transgenic mice under the authorization previously described.

In Vivo Stereotaxic Injection of VHH

Stereotaxic injections were performed in TauPS2APP (n=2 female) transgenic anesthetized mice with 2 μl of VHH per injection at the rate of 0.5 μl/min. The mice were anesthetized with a mixture of isoflurane (1-2%) and air (1 L/min). They were placed on a stereotaxic frame and the skull was bilaterally perforated with a Dremel. Blunt Hamilton syringes were used to inject MR contrast agent. Each mouse received 4 injections, in the frontal cortex and the hippocampus in each hemisphere. The stereotaxic coordinates in the frontal cortex were +0.86 mm anterior from bregma, ±1.5 mm lateral from the midline, −0.65 mm ventral from dura. The stereotaxic coordinates in the hippocampus were −2.18 mm posterior from bregma, ±1.5 mm lateral from the midline, −1.8 mm ventral from dura. Two or 24 hours after the injection, mice were euthanized and perfused intracardially with 4% paraformaldehyde in PBS (pH 7.6). Brains were removed and postfixed in the same fixative overnight at 4° C. 4 μm thick paraffin sections were prepared. The presence of the VHH in cerebral tissue was detected using either of the standard immunohistochemical procedures described above.

Intracarotid Perfusion of VHH in Mouse Models of Amyloidosis

Intracarotid administration of VHH was performed in anesthetized TauPS2APP mice (n=2, females). The anesthesia was performed by injecting once intraperitoneally a mixture of ketamine hydrochloride (Imalgen, 50 μl of a solution diluted 1/10) and xylazine (Rompun, 50 μl of a solution diluted 1/40). The common carotid artery was exposed and cannulated with fine silicon tubing (PP25_100 FT; Portex, Ashford, UK). VHH was infused into the carotid at a constant rate using a peristaltic pump (Model PHD 2000; Harvard Apparatus, Boston, Mass., USA).

Lateral Tail Vein Injection

Mice were placed in an appropriate inverted beaker with hole for tail access. The animals were warmed before the injection and the tail was soaked with lukewarm water to cause vasodilatation of the vein. Injections before the MR images were performed after insertion of a catheter (27G, Microflex, Vygon, France) into the tail vein of the animals, in order to warrant the proper administration of the contrast agent. Two mg of VHH, VHH R3VQ-DOTA, or VHH R3VQ-S-(DOTA/Gd)$_3$ dissolved in 200 μl PBS was then injected into the lateral tail vein.

In Vivo MRI

In vivo MRI was performed on a 7 T-Spectrometer (Agilent, USA) interfaced with a console running VnmrJ 2.3 as previously described (see in vitro MRI chapter). During the MRI experiment the animals were anesthetized with a mixture of isoflurane (0.75-1.5%) and carbogen (95% O2-5% CO2) and their breathing rate was monitored. Carbogen was used to reduce the signal coming from circulating blood (Thomas et al., 2003).

MR images were recorded using a high-resolution 3D-Gradient Echo sequence (29*29*117 μm³, FOV: 15*15*15 mm³, Mtx=512*512*128, TR=30 ms, TE=15 ms, flip angle=20°, Nex=1, bandwidth=25 kHz, Acquisition Time: 32 min (Petiet, A. et al., 2012, Neurobiol Aging, 33:1533-44).

The T1 calculation was based on seven successive 2D multi-slice spin echo images with five TR values (TR=0.4, 0.75, 1.5, 2.5, and 5 s, TE=14 ms, Nex=1, FOV=25×25 mm2, Mtx=128×128, 6 slices, slice thickness=1 mm, bandwidth=50 kHz). Parametric maps of relaxation times were calculated from exponential regression curves (S=1−exp(−TR/T1)) where S is the signal intensity, TR is the repetition time and T1 is the longitudinal relaxation time (ImageJ, MRI Analysis Calculator, Karl Schmidt). Relaxation times were measured from cortical regions in the frontal part of the brain.

Ex Vivo MRI 6 h after in vivo intracerebroventricular injections of VHH-S-(DOTA/Gd)$_3$ (1 µg/side), mice were perfused (PFA 4%) and their brains were extracted prior to ex vivo MR images. For each procedure, controls were performed by using an equivalent solution of Gd (i.e: 0.1 mM).

Results

1. Library Construction, and Selection of Specific Anti-Aβ VHH

VHHs were amplified by PCR and cloned in vector pHEN1. Subsequent transformations yielded a library of about 10$^8$ clones. VHHs displaying the best affinity were selected by phage display through 3 palming cycles with biotinylated Aβ1-42, Aβ1-40 or Aβ1-16 peptides. 46 individual clones were tested by ELISA from Aβ42 panning, 192 clones from Aβ40 and 192 clones from Aβ16. 46/46, 110/192 and 163/192 were found positive from Aβ42, Aβ40 and Aβ16 pannings, respectively. These positive clones were sequenced and 45, 65 and 118 VHH sequences were respectively identified. Finally 3 families of VHH were selected (A7/B10, F12 and R3VQ) (see Table 1 below). A7/B10 VHHs were found 11, 64 and 117 times after pannings against, respectively, biotinylated Aβ1-42, Aβ1-40 or Aβ1-16. VHH R3VE/Q were found respectively 34 times and once after panning against biotinylated Aβ1-42 and Aβ1-40 while VHH F12 were found once after Aβ16 panning.

These VHHs were subcloned in vector pET23 or in vector pASK IBA2 to allow a high level of expression of VHH with, respectively, a His-tag or a Streptavidin-tag. Yields of 1-2 mg/l of bacterial culture were obtained. The single domain products were shown to be pure to homogeneity by SDS-PAGE (data not shown); their pI values were above 8.5. Subsequent experiments were performed with the two constructs.

R3VQ is kept at 4° C. or for long term storage at −20° C. with glycerol. It is not stable frozen without glycerol.

DLS experiments showed that R3VQ is monomeric and not aggregated after purification.

Amino-acid sequence alignment of anti-Aβ VHHs A7, B10, R3VE, R3VQ and F12 is shown in FIG. 10.

2. Recognition of Amyloid Plaques by VHH R3VQ

Immunoreactivity of VHH R3VQ for Aβ and Amyloid Lesions

Figure 2A:
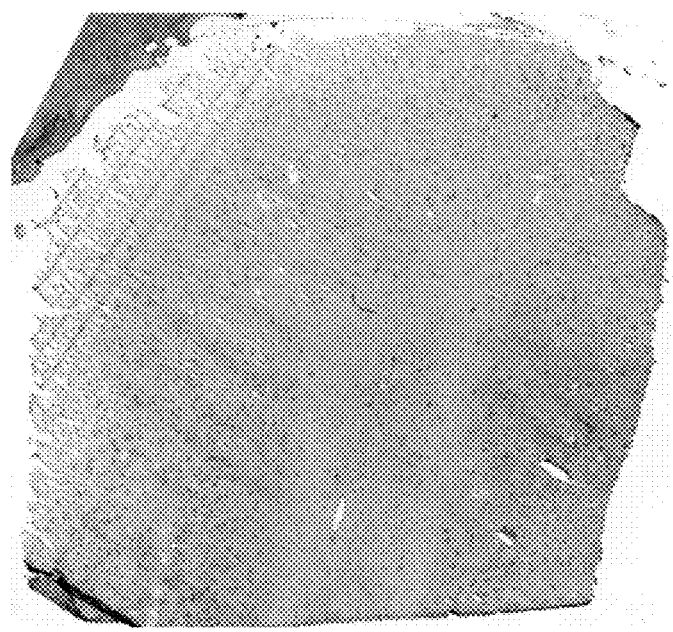
FIG. 2 shows the immunohistochemical staining of amyloid β plaques using the VHH R3VQ on fresh human AD brain tissues (A and B). 4G8 (Wisniewski T. et al., 1996, B. Biochem J., 313:575-80) was used as a reference anti-Aβ antibody (C and D).
Figure 2B:
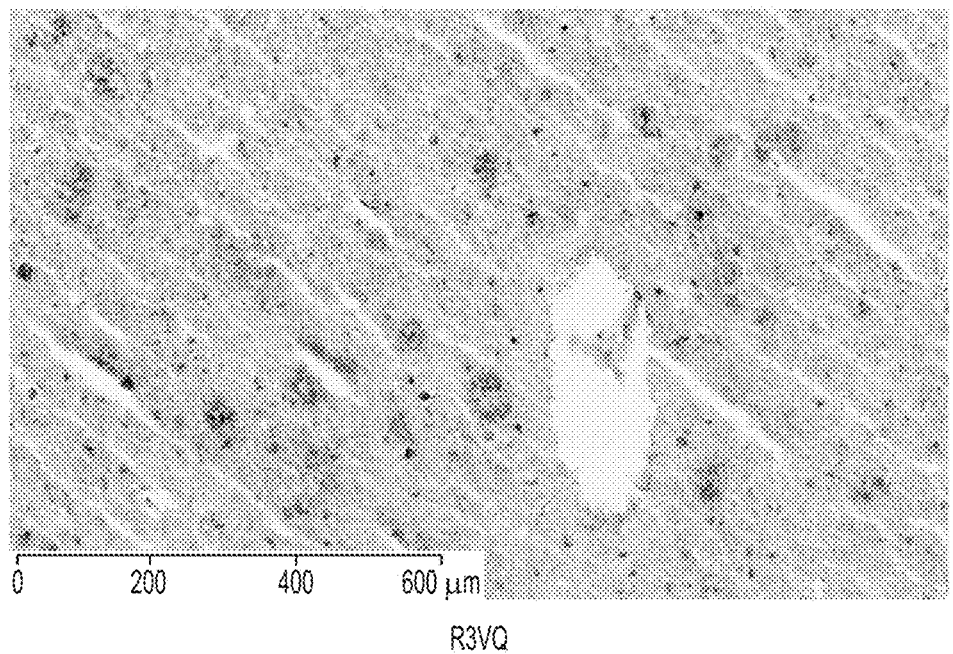
Figure 2C:
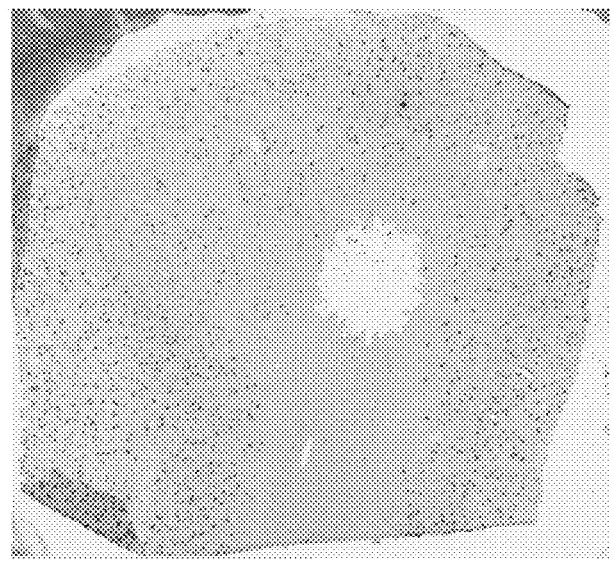
Figure 2D:
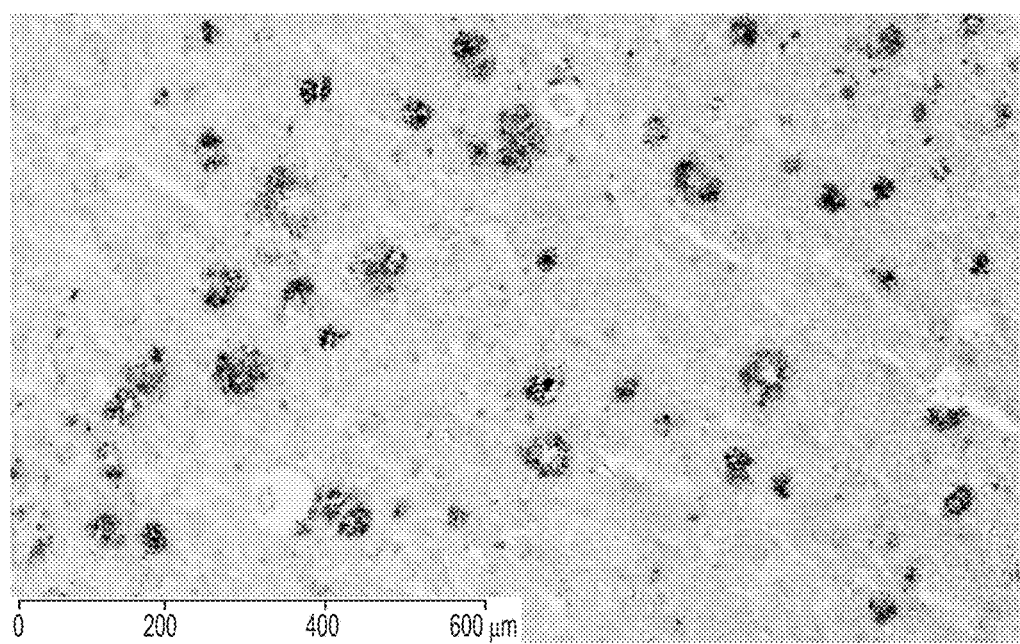
Figure 3A:
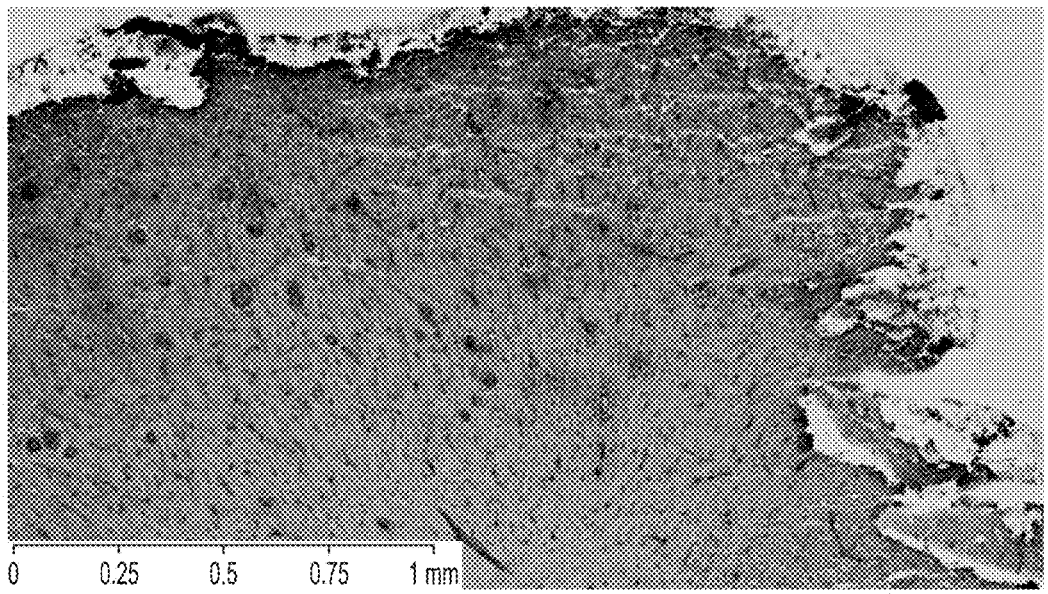
FIG. 3 shows the immunohistochemical staining of amyloid plaques using the VHH R3VQ on fresh brain transgenic TauPS2APP mice tissues (A). 4G8 was used as a reference anti-Aβ antibody (B).
Figure 3B:
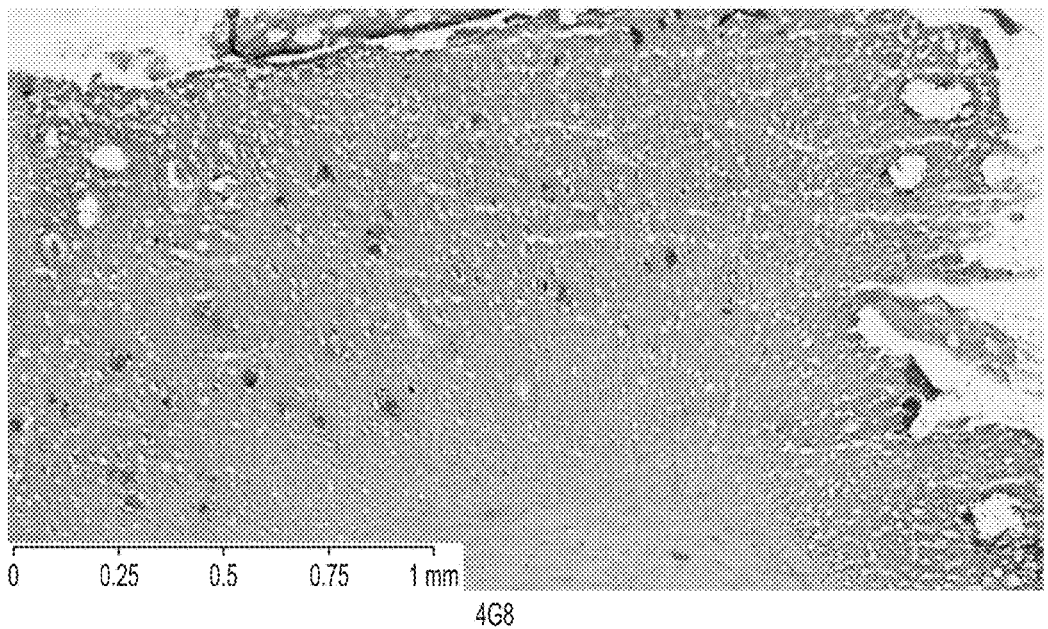

It was examined the distribution of VHH-specific immunoreactivity in human AD brains and transgenic TauPS2APP mice. R3VQ showed good ability to immunodetect Aβ plaques and cerebral amyloid angiopathy (CAA) in human paraffin sections after antigen retrieval pretreatment (FIG. 1). No labelling was observed with wild type mice. Paralleling result on paraffin-embedded tissues, it was showed that Aβ immunodetection using R3VQ can be readily obtained on free-floating vibratome sections (data not shown) and, more importantly, on fresh tissues from AD human brains and from mouse brain sections without the use of any antigen retrieval pre-treatment (FIG. 2-3). Noticeably the strong background signal and low signal/noise ratio observed with free-floating sections obtained on a freezing microtome, precluded the use of this material for R3VQ IHC. Amyloid plaques immunolabelling was undetectable for VHH A7/B10 and F12 and no longer experiments were performed with these VHHs.

Figure 4A:
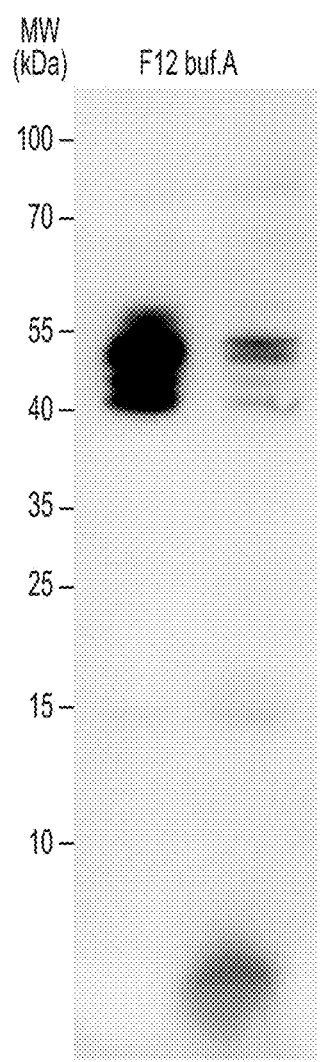
FIG. 4 shows the Western Blot on human brain extracts and on Aβ42 revealed by VHH R3VQ (phenol red-free Ham's F12 medium (Gibco) or buffer A [PBS, pH 7.4, 0.32 M sucrose, 50 mM Hepes, 25 mM MgCl2, 0.5 mM DTT] containing protease inhibitors [200 µg/ml PMSF, 2 µg/ml pepstatin A, 4 µg/ml leupeptin, 30 µg/ml benzamidine hydrochloride]).
Figure 4B:
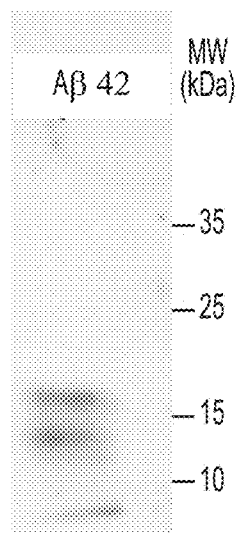

To confirm the immunoreactivity of VHH R3VQ on brain tissues, western-blot immunoassays were performed on brain extracts obtained from AD patients. Four principal bands, corresponding to Aβ oligomers between 40 and 55 kDa, were immunodetected with VHH R3VQ. In parallel R3VQ recognized three bands with Aβ42 peptide between 6 and 17 kDa corresponding to monomers, dimers and trimers (FIG. 4).

R3VQ Recognizes the Central Region of Aβ42

VHH R3VQ was shown to be specific for fibrillar synthetic Aβ42 peptide in inhibition assays using Aβ42. VHH R3VQ had a KD of 17 nM. To further determine the epitope recognized by VHH R3VQ, the concentration required for 50% inhibition (IC50) was determined for Aβ40 and for peptides corresponding to different Aβ fragments (1-16, 10-20, 15-25, 22-35 and 29-40). VHH R3VQ did neither recognize fragments 1-16 nor 29-40. The IC50 of VHH R3VQ for Aβ 16-35 was 16 nM, suggesting that VHH R3VQ recognizes an epitope located in the central part of Aβ42. R3VQ did not recognize APP by flow cytometry using the H4 stable clone provided by Roche (data not shown).

VHH R3VQ Labels Amyloid Plaques In Vivo after Stereotaxic Injection

Figure 5A:
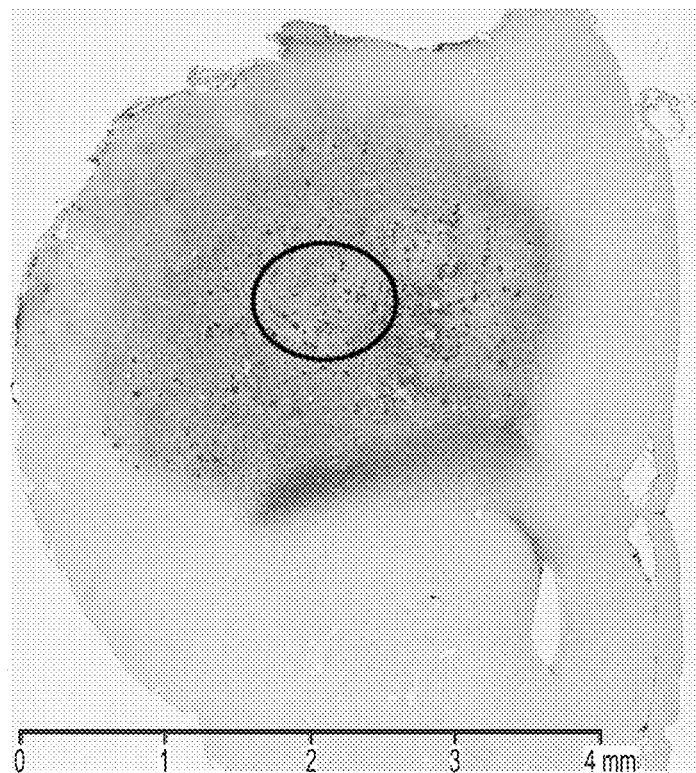
FIG. 5A shows the immunohistochemical staining of amyloid β plaques in transgenic TauPS2APP mice paraffin embedded sections after stereotaxic injections of VHH R3VQ.
Figure 5B:
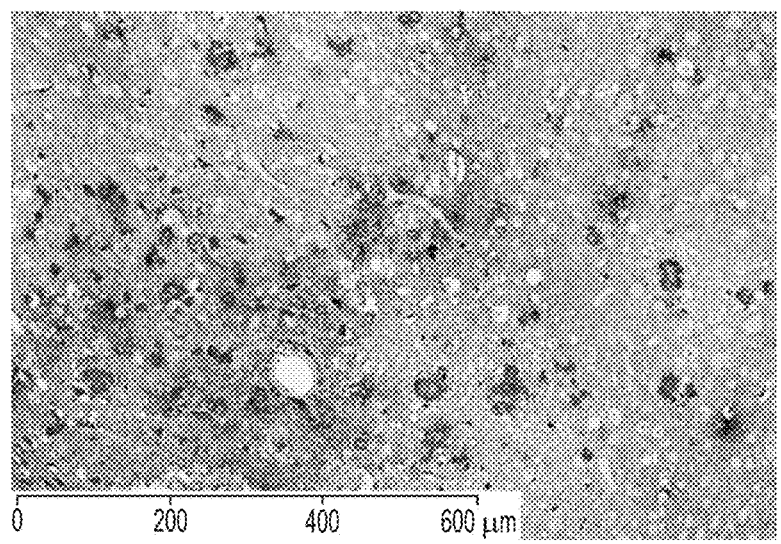
FIG. 5B shows a magnification of the inset of FIG. 5A.

Two µg of VHH R3VQ were injected stereotaxically into the hippocampus or the cortex of the left hemisphere of the mouse brain (2 mice). 2 h or 24 h after the injection, the animals were sacrificed and brain sections were collected Immunostaining of amyloid plaques was observed indicating that VHH R3VQ labeled fibrillar Aβ in vivo. Moreover, it was noticed a brown halo in the cortex indicating the diffusion of VHH R3VQ into brain tissues (FIGS. 5A and 5B).

VHH R3VQ Crosses the BBB In Vivo

VHH R3VQ was tested in vivo for its ability to cross the BBB. Four mgs of VHH was injected via the left carotid artery over a period of 60 min. Following the injection, the diffusion of VHH into cerebral tissues was allowed for 1 hour before the mice were euthanized and perfused with fixative. Immunostaining of amyloid plaques was observed in cortex, hippocampus and thalamus. This staining was faint in the right hemisphere contralateral to the injected carotid.

The experiments showed that unlabeled R3VQ 1) was able to cross BBB following slow intra-carotid infusion, 2) specifically recognized amyloid plaques in vivo, and 3) is a good candidate for MRI studies.

Comparison Between VHH R3VQ and Known VHHs Directed Against Amyloid β

Table 1 below summarizes the labeling of VHHs directed against amyloid obtained by immunization of an alpaca with the peptide Aβ42, the peptide Aβ1-10 coupled to the ovalbumin or fibrillar form of Aβ42. The selections of the VHHs have been carried out by phage display, except for VHHs R1.3, R1.5 and R3.3 which have been selected by ribosome display.

TABLE 1

Labeling of VHHs directed against amyloid β obtained by immunization of an alpaca with the peptide Aβ42, the peptide Aβ1-10 coupled to the ovalbumin or fibrillar form of Aβ42. VHHs L1-3, L35, 61-3, V31-1 are disclosed in Lafaye P. et al., 2009, Molecular Immunology, 49: 695-704. The other VHHs were obtained according to the method disclosed above.

| VHHs clones | Immunogens | Selection | Labeling Amyloid angiopathy (CAA) | Amyloid oligomers | Amyloid plaques |
|---|---|---|---|---|---|
| | Aβ42 oligomer | Aβ42 coated tubes | | | |
| L1-3 | | | 0 | 0 | 0 |
| L35 | | | 0 | 0 | 0 |
| 61-3 | | | 0 | 0 | 0 |
| V31-1 | | | 0 | ++ | 0 |
| | | Aβ1-10 coated tubes | | | |
| L3 | | | 0 | 0 | 0 |
| L4 | | | 0 | 0 | 0 |
| L7 | | | 0 | 0 | 0 |
| V2 | | | 0 | 0 | 0 |
| V17 | | | | 0 | 0 |
| V11 | | | 0 | 0 | 0 |
| | OVA Aβ1-10 | Aβ1-16 coated tubes | | | |
| NN1 | | | ++ | 0 | 0 |
| NN3 | | | ++ | 0 | + |
| NN4 | | | | | |
| | Fibrillar Aβ42 | Aβ42 coated tube | | | |
| 2D5 | | | 0 | 0 | 0 |
| 3F7 | | | 0 | 0 | 0 |
| 2A5 | | | 0 | 0 | 0 |
| 3B4 | | | 0 | 0 | 0 |
| 3B10 | | | 0 | 0 | 0 |
| 3H7 | | | 0 | 0 | 0 |
| | Fibrillar Aβ42 | Ribosome display + Aβ42 coated tubes | | | |
| R1.3 | | | ++ | 0 | 0 |
| R1.5 | | | 0 | 0 | 0 |
| R2.3 | | | ++ | 0 | 0 |
| R3.3 | | | ++ | 0 | + |
| | Fibrillar Aβ42 | Biotinylated Aβ40 or biotinylated Aβ16 biotinyle + magnetic beads | | | |
| B10 | | | 0 | 0 | 0 |
| A7 | | | 0 | 0 | 0 |
| F12 | | | 0 | 0 | 0 |
| | Fibrillar Aβ42 | Biotinylated Aβ42 + magnetic beads | | | |
| R3VE R3VQ | | | ++ | 0 | +++ |
| | | Control | | | |
| AcM 6F/3D | | | +++ | | +++ |

The results show that among the 27 VHHs tested only VHH R3VE/Q is able to label amyloid angiopathy and amyloid plaques but not amyloid oligomers.

3. Antibody Coupling to MRI Contrast Agent

Non-Site Specific Approach:

Conjugation was performed with NHS-activated DOTA to VHH lysine residues. Subsequent chelation with Gd has resulted in conjugates with variable ratios of DOTA/Gd on the protein (Table 2). Monitoring of both steps by HPLC/MS has allowed to optimize the process. Nearly complete chelation could be achieved at room temperature.

Two initial conjugates (2a and b) have showed no Aβ binding activity due to instability during storage at −20° C. without glycerol. By varying experimental conditions, four new conjugates have been prepared in 0.5-1 mg scale with a good recovery (64-74%). The first series (2c and d) has a higher DOTA/Gd density than the second series (2e and f). Compared to the original VHH 1 Aβ recognition in ELISA, the binding of 2c and 2d is low (~10%) while the binding of 2e and 2f is hardly affected (50 to 100%). This difference might be due to the overall lower density of DOTA/Gd and/or inherent stability of the VHH.

TABLE 2

Characteristics of R3VQ(His)-N-(DOTA/Gd) conjugates

| Compound | Experimental conditions | | | Average DOTA/ protein[b] | Average Gd/ protein[b] | Overall yield (%) | ELISA vs original VHH |
|---|---|---|---|---|---|---|---|
| | Initial storage | Conjugation[a] | Chelation[a] | | | | |
| 2a | −20° C. | 12 × 2 eq, 12 h | 20° C., 2 h 30 | (3) 4 5 (6) | (3) 4 (5) | 67 | − |
| 2b | −20° C. | 12 × 2 eq, 12 h | 60° C., 15 min | (3) 4 (5) | (3) 4 (5) | 65 | − |
| 2c | −20° C. + glycerol | 12 × 2 eq, 12 h | 20° C., 2 h 30 | (1) 2 (3) | (1) 2 (3) | nd | + |
| 2d | −20° C. + glycerol | 12 × 2 eq, 12 h | 60° C., 20 min | (1) 2 (3) | (1) 2 (3) | nd | + |
| 2e | +4° C. | 11 × 0.5 eq, 8 h 15 | 20° C., 2 h 30 | (0) 1 2 (3) | (0) 1 2 (3) | 60 | ++ |
| 2f | +4° C. | 4 eq, 3 h | 20° C., 2 h 30 | (0) 1 (2) | (0) 1 (2) | 67 | ++ |

[a]The reactions are performed at room temperature.
[b]Determined by MS. The minor compounds are in brackets.

Site Specific Approach:

This strategy involves the labeling of the Cys-engineered R3VQ VHH (R3VQ-SH 3) (SEQ ID NO 8) with a maleimido-(DOTA/Gd)$_3$ compound 4 (see FIG. 9B).

DOTA is represented as the monoacyl moiety. The overall yield is indicated in brackets.

When conjugated to 4 by thioaddition, 3 was totally converted into the well-defined compound R3VQ-S-(DOTA/Gd)$_3$ 5, as shown by RP-HPLC/MS, with 79% yield. The pI of 5 was slightly reduced compared to the one of the unlabeled R3VQ-SH. The binding characteristics of R3VQ-SH and R3VQ-S-(DOTA/Gd)$_3$ were determined in competitive inhibition experiments involving Aβ40 bound to the ELISA plate and soluble Aβ40. The concentration of Aβ40 giving 50% binding inhibition was calculated to be 1 μg/ml for both R3VQ-SH and R3VQ-S-(DOTA/Gd)$_3$ suggesting that the addition of DOTA/Gd does not affect the VHH binding properties. Further, following the distribution of VHH-specific immunoreactivity in transgenic B6.PS2APP mice, R3VQ-SH showed good ability to immunodetect Aβ plaques in mouse paraffin sections after antigen retrieval pretreatment.

R3VQ-SH was constructed with a C-terminal Cys residue for coupling to Maleimido-DOTA/Gd (FIG. 9). 15 mg of purified protein is expressed per L of culture. However several constructs have been realized before and are summarized below:

Strep-R3VQSSfree-Cys-Thr-His containing from the Cter to the Nter a strep tag, VHH R3VQ with Cys mutated to Val and Ser, a Cys, a thrombin cleavage site and a his tag. This protein was expressed at very low yield Gig protein/1).

Tag-R3VQSSfree-Cys and His Tag-R3VQSSfree-Cys containing from the Cter to the Nter a tag (either Strep or His tag), VHH R3VQ with Cys mutated to Val and Ser and a Cys; Both proteins were expressed at very low yield (μg protein/1).

Tag-R3VQSSfree-Cys-Ser-Ala containing from the Cter to the Nter a tag (either Strep or His tag), VHH R3VQ with Cys mutated to Val and Ser, a Cys, a Ser and an Ala. These proteins were expressed at very low yield (μg protein/I).

Tag-Thr R3VQSSfree-Cys-Ser-Ala containing from the Cter to the Nter a tag (either Strep or His tag), a thrombin cleavage site, VHH R3VQ with Cys mutated to Val and Ser, a Cys, a Ser and an Ala. These proteins were expressed at very low yield (μg protein/1).

4. Detection of Amyloid Plaques with VHH R3VQ Conjugated with Gd Contrast Agent

Figure 6A:
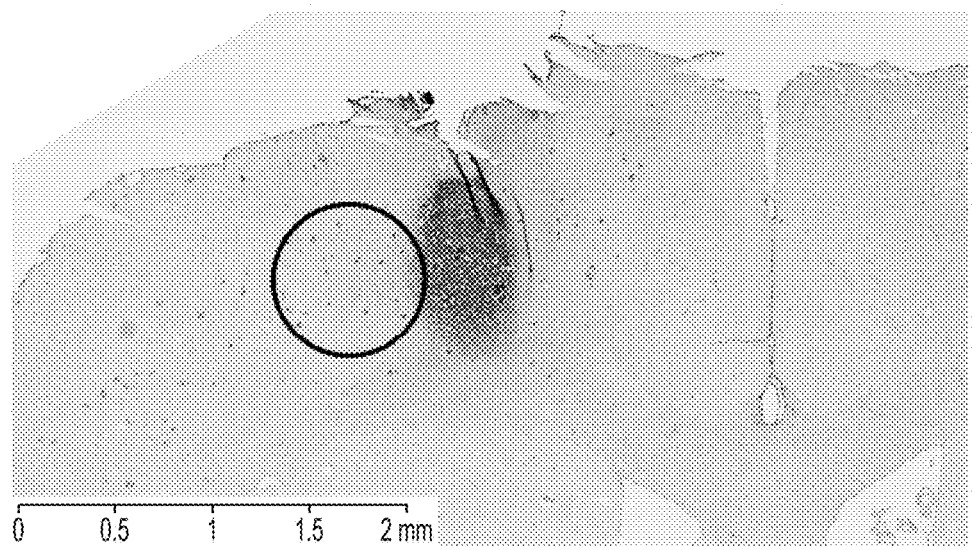
FIG. 6A shows the immunohistochemical staining of amyloid β plaques in transgenic TauPS2APP mice paraffin embedded sections after stereotaxic injections of R3VQ-N-(DOTA/Gd)$_{1-2}$ 2e.
Figure 6B:
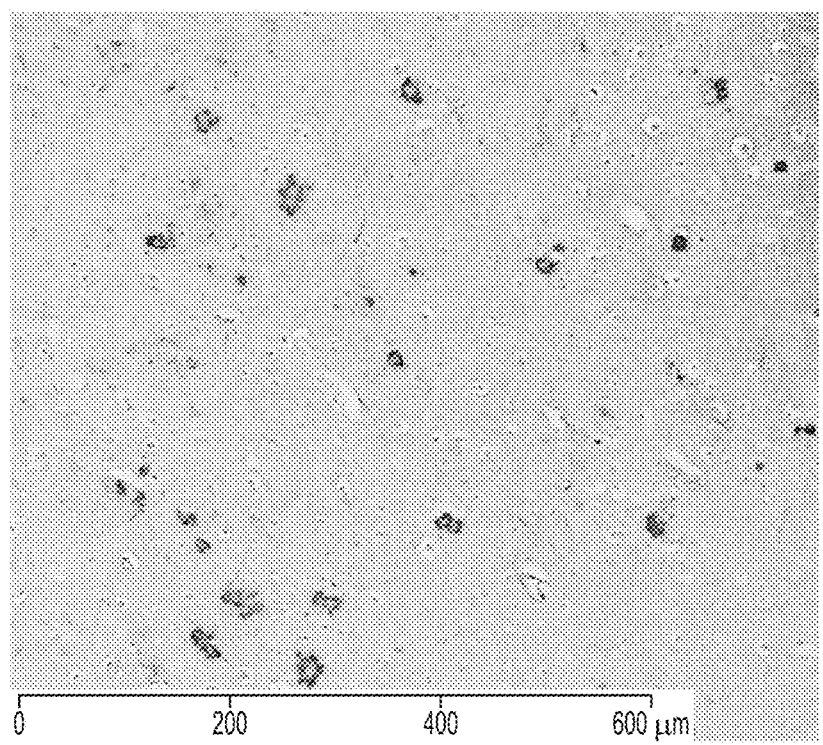
FIG. 6B shows a magnification of the inset of FIG. 6A.
Figure 6C:
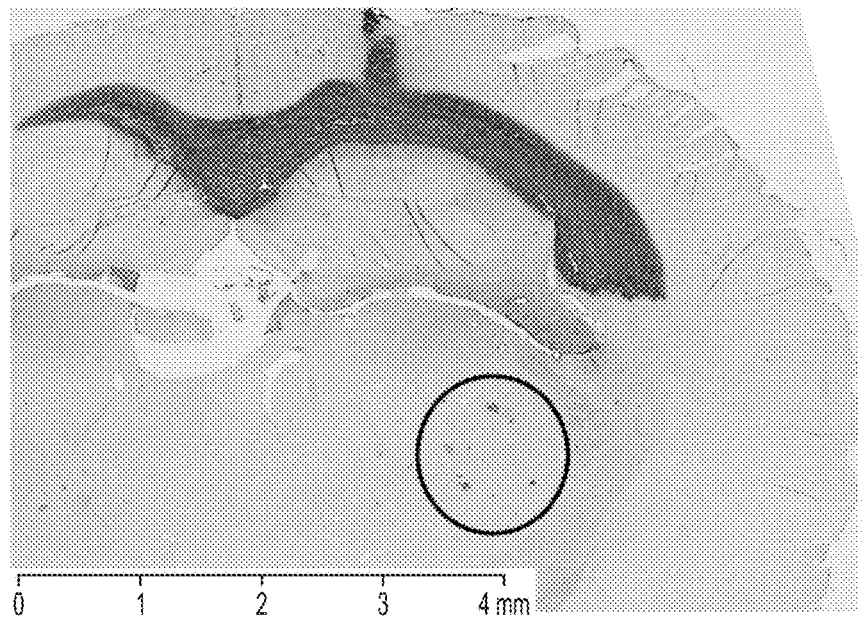
FIG. 6C shows labeling of amyloid β plaques present in the thalamus, at distance from the injection site.
Figure 6D:
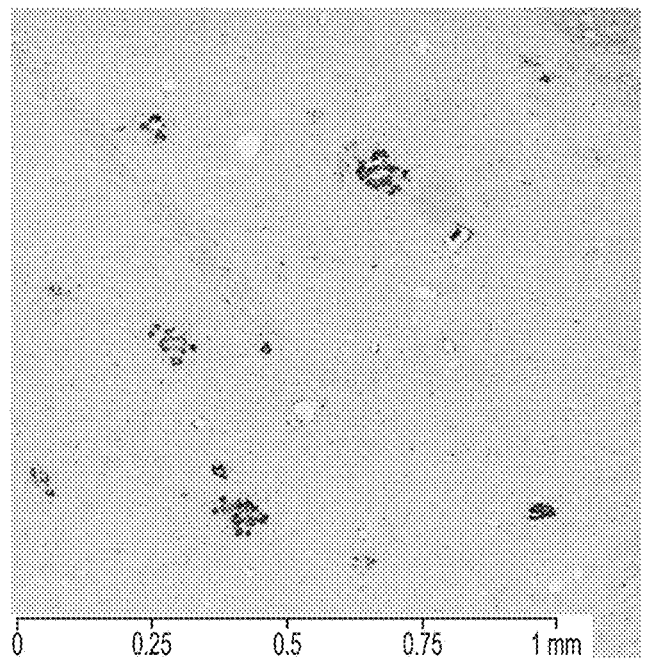
FIG. 6D shows a magnification of the inset of FIG. 6C.
Figure 6E:
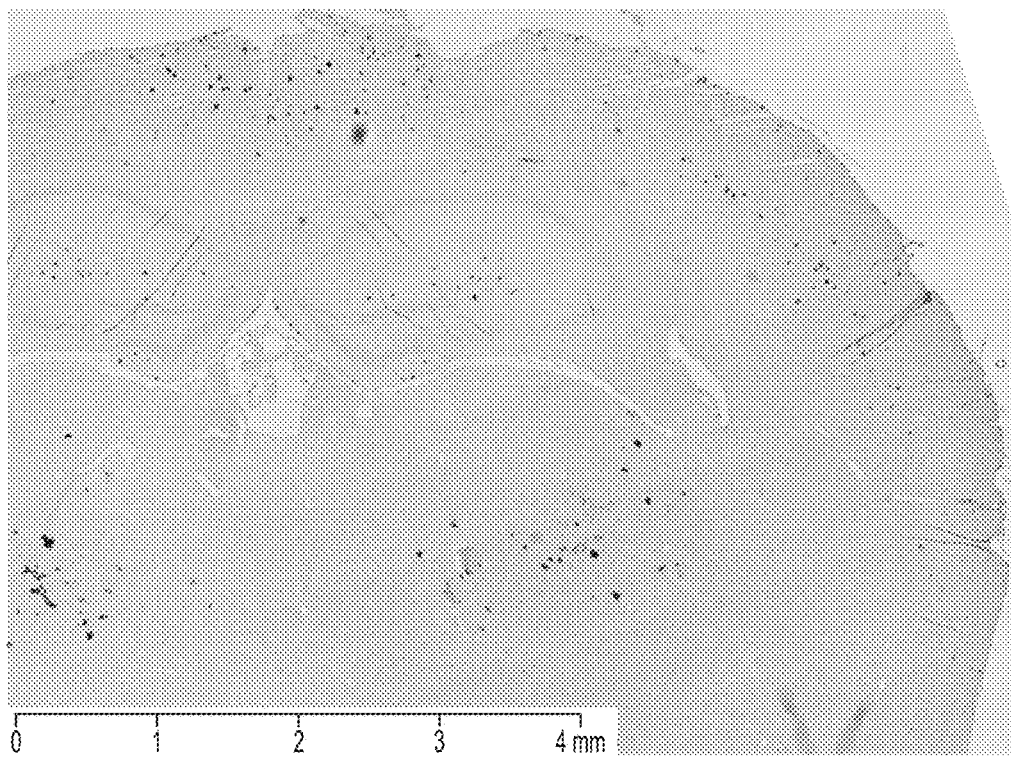
FIG. 6E shows the control performed with 4G8 antibody on the same mouse to label amyloid plaques.

R3VQ-N-(DOTA/Gd)$_{(1-2)}$ Labels Amyloid Plaques In Vivo after Stereotaxic Injection Two μg of VHH R3VQ-N-(DOTA/Gd)$_{1-2}$ (2e) were injected stereotaxically into the hippocampus or the cortex of the left hemisphere of the mouse brain (2 mice). 4 h after the injection, the animals were sacrificed and brain sections were collected. Immunostaining of amyloid plaques was observed indicating that R3VQ-N-(DOTA/Gd)$_n$, labeled fibrillar Aβ in vivo (FIGS. 6A and 6B). FIGS. 6C and 6D shows labeling of amyloid β plaques present in the thalamus, at distance from the injection site. A control was performed with 4G8 antibody on the same mouse to label amyloid plaques (FIG. 6E).

In-Vitro Imaging

Imaging of brains of TauPS2APP mice soaked in a solution of R3VQ-N-(DOTA/Gd)$_{1-2}$ (2e contrast agent at a final concentration of 0.02 mg/ml, equivalent to a 0.01 mM of Gd) revaled several hypointense spots (n=2; FIG. 7A, arrows) that could not be detected in the brains of control mice images in the same condition (data not shown) that could be colocalized with amyloid plaques revealed by the Gd-staining method (FIG. 7B, arrows). IHC confirmed the large diffusion of VHH-DOTA/Gd and the labeling of amyloid plaques in the same area (FIG. 7C, arrows), even if the distortion induced by the paraffin procedure did not allow point-to-point registration between MRI and IHC. Moreover, no hypointense spots could be detected in the brains of control mice images in the same condition (n=2; data not shown) or in the brains of TauPS2APP mice soaked in Gadolinium solution at the same concentration (i.e., 0.01 mM; FIG. 7D).

Ex-Vivo Imaging after Intracerebral, Intracarotid or IV Injection

After intracerebroventricular injection, the anti-Aβ VHH-Gd 2e (R3VQ-N-(DOTA/Gd)$_{1-2}$) showed hypointense spots on ex vivo images in the hippocampus (FIG. 8A, arrows) that correspond to amyloid plaques as confirmed by Gd-staining on the same mouse (FIG. 8B, arrows). IHC confirmed the labeling of amyloid plaques in the same area (FIG. 8C, arrows), even if the distortion induced by the paraffin procedure did not allow point-to-point registration between MRI and IHC. Moreover, no hypointense spots could be detected with the injection in a transgenic TauPS2APP mouse of a Gadolinium solution at the same concentration (0.1 mM) used with R3VQ-N-(DOTA/Gd)$_{1-2}$.

Evaluation of R3VQ-S-(DOTA/Gd)$_3$ by In Vitro MRI

R3VQ-S-(DOTA/Gd)$_3$ was synthesized by site specific approach as described above. The HPLC/MS, pI, and IHC assays confirm the biochemical properties (i.e. purity by HPLC/MS, pI, and IHC reactivity against Aβ) of R3VQ-S-(DOTA/Gd)$_3$ (see FIG. 11).

The potential of R3VQ-S-(DOTA/Gd)$_3$ to induce MR contrast modification was evaluated after in vitro incubation of brains from PS2APP mice (Richards, J. G., et al., 2003, The Journal of neuroscience: the official journal of the Society for Neuroscience 23, 8989-9003) (n=2) with R3VQ-S-(DOTA/Gd)$_3$ at 0.1 mg/ml as described above. Images acquired at 7 T revealed hypointense spots in the cortex as compared to brains of PS2APP mice under negative control condition (FIGS. 12A and B). To confirm the nature of these hypointense spots as amyloid plaques, brains were submitted to a Gd-staining procedure used as the gold-standard method for MRI detection of amyloid plaques (FIG. 12C). Analyses of images obtained after the Gd-staining procedures allowed the co-registration of the amyloid plaques detected by Gd-staining with the hypointense spots revealed by the R3VQ-S-(DOTA/Gd)$_3$ (FIG. 12, white arrows). These results suggest that R3VQ-S-(DOTA/Gd)$_3$ passively diffuses in postmortem tissues and targets amyloid deposits allowing their detection by in vitro MRI.

Evaluation of R3VQ-S-(DOTA/Gd)$_3$ by Ex-Vivo MRI after Peripheral (Intravenous) Injections R3VQ-S-(DOTA/Gd)$_3$ ability to reveal amyloid plaques by MRI was then investigated after intravenous injection in the tail vein (20 mg/kg and 50 mg/kg) of 18-month-old PS2APP mice as described above. The MR images acquired at 11.7 T of the PS2APP mice injected intravenously with R3VQ-S-(DOTA/Gd)$_3$ were acquired after brain extraction 5 hours following injection. Contrary to MR images of the control condition (PS2APP mice injected with PBS) (FIGS. 13A and B), images obtained on ex vivo brains that received intravenous injection of R3VQ-S-(DOTA/Gd)$_3$ showed numerous hypointense spots (FIGS. 13C and D). These hypointense spots were co-registered with contrast anomalies corresponding to amyloid plaques as detected with a gold-standard Gd-staining procedure (FIGS. 13E and F). These spots were more intense with the 50 mg/kg dose suggesting, according to the two-photons results, that R3VQ brain penetration and its potency to label brain AB lesions were dose-dependent.

EXAMPLE 2

Generation of Anti-Abeta VHHs Coupled to a Fluorophore Agent and its Evaluation In Vitro/In Vivo 1. Materials and Methods Unless explicitly mentioned hereafter the materials and methods are the same as described for Example 1.

2. In Vivo Targeting of Aβ-Positive Lesions

Conjugation of R3VQ-SH with AF488 Fluorophore

In order to realize the coupling between R3VQ VHH and a fluorophore, a site specific conjugation was implemented as described above. Briefly, an additional cysteine residue was inserted in the C terminal part of the sequence of R3VQ (referred to as R3VQ-SH), thus allowing a C terminal thio-addition of a maleimido-Alexa Fluor® 488 (AF488). By this way, it was obtained a well defined conjugate, referred to as R3VQ-S-AF488, with a single AF488 on the VHH (FIG. 14).

Figure 14A:
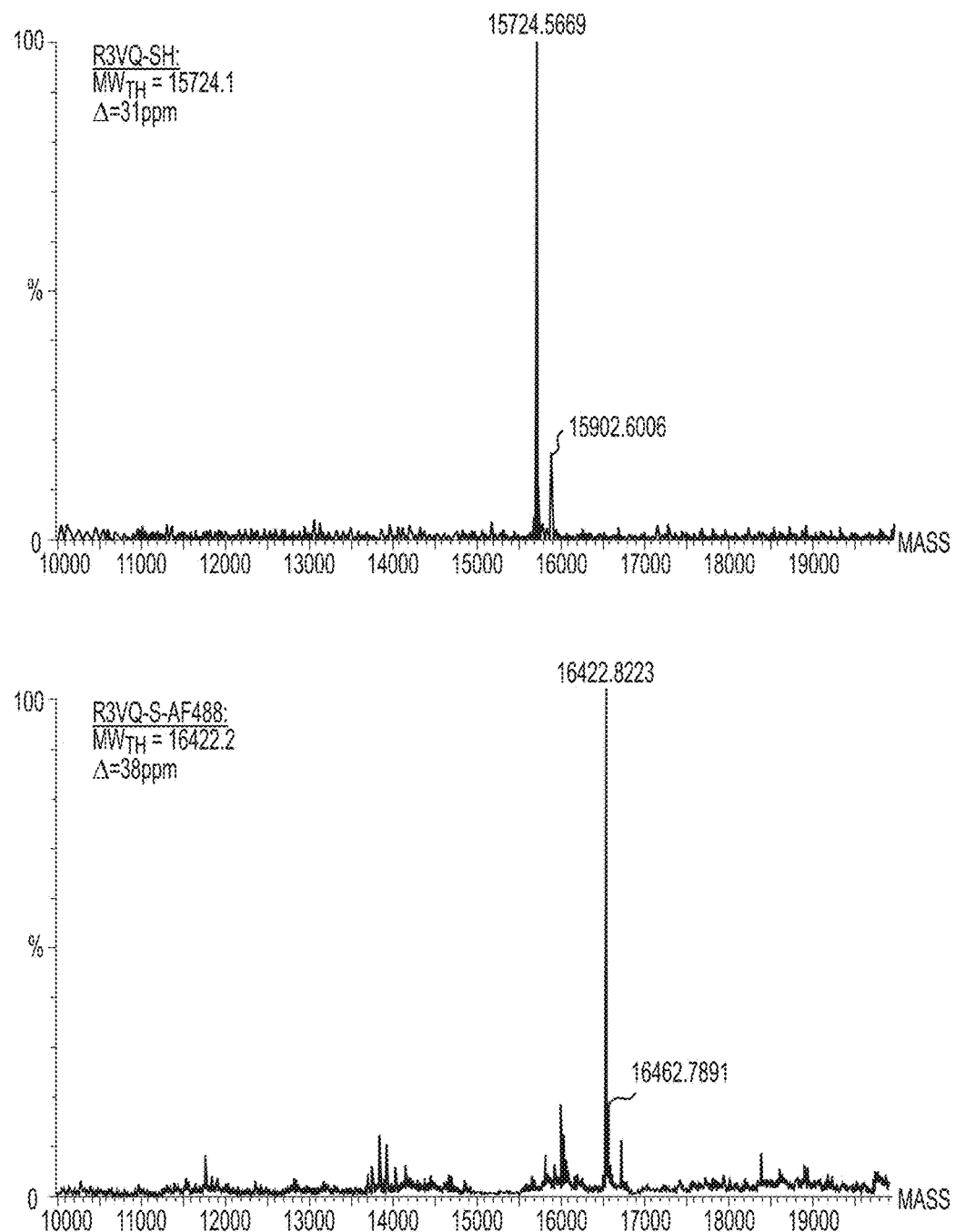
Figure 14B:
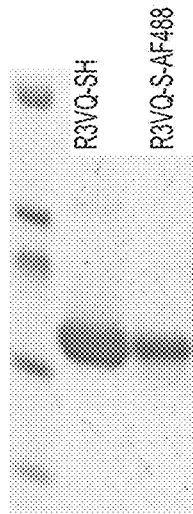

SDS-PAGE and HPLC/MS analyses showed the expected molecular weight (increase of 698 Da) corresponding to the addition of AF488 to the molecule. These data confirm the labeling and the purity of the conjugate (FIGS. 14A and B).

Figure 14C:
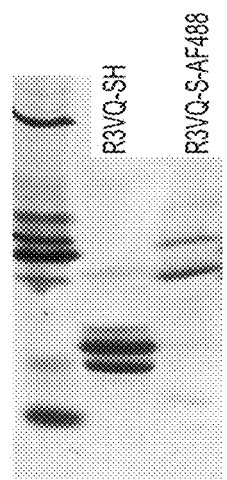
Figure 14D:
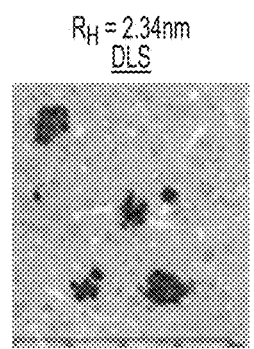

The isoelectric point (pI) of R3VQ-SH and R3VQ-S-AF488 were analyzed by NEPHGE using IEF 3-10 gel. The pI of R3VQ-SH was between 8.5 and 9.5 (FIG. 14C), similar to R3VQ's pI. The addition of AF488 to R3VQ-SH slightly decreased its pI, which was around 8.3, however, still basic (FIG. 14C). The hydrodynamic radius ($R_H$) of R3VQ-SH and R3VQ-S-AF488 were measured by DLS. The size distribution over time showed an average $R_H$ of 2.66±0.0788 nm for R3VQ-SH and an average $R_H$ of 2.34±0.106 nm for R3VQ-S-AF488, which suggested that both of them were in monomeric form in solution. Immunostaining of amyloid plaques by R3VQ-S-AF488 was confirmed in vitro by IHC using brain slices from PS2APP mice (FIG. 14D).

Diffusion of R3VQ-S-AF488 after Topic Brain Infusion (Two-Photon Imaging)

Craniotomy was performed on a PS2APP mouse to obtain a skull window over the right posterior cortex. 15 μg (10 μl) of R3VQ-S-AF488 was applied directly onto the exposed brain after peeling off the dura. R3VQ-S-AF488 diffusion was followed up for about 2 hours by two-photon microscopy. Typical specific staining of amyloid plaques and CAA was detected in brain parenchyma, suggesting that R3VQ-S-AF488 was able to diffuse and detect in vivo extracellular and vascular AB-positive lesions after pericortical infusion (FIG. 15).

Diffusion of R3VQ-S-AF488 after Intravenous Injection (Two-Photon Imaging)

The integrity of the blood-brain barrier (BBB) of the tested mice was first checked by MRI (see control experiments below) to ensure absence of leakages that may artificially favor brain penetration of the intravenous (iv) injected VHHs.

Figure 16A:
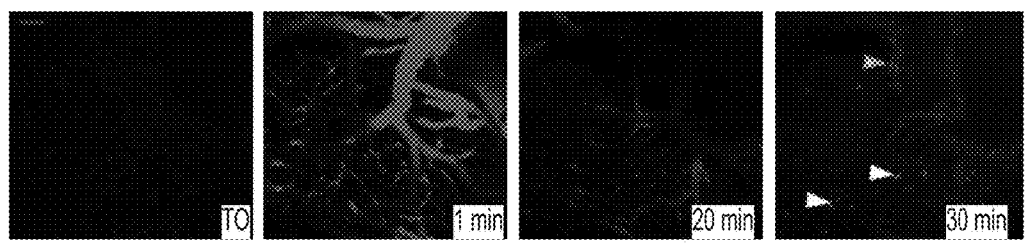
Figure 16B:
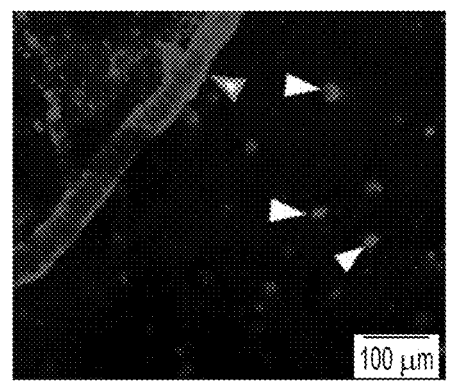
Figure 16C:
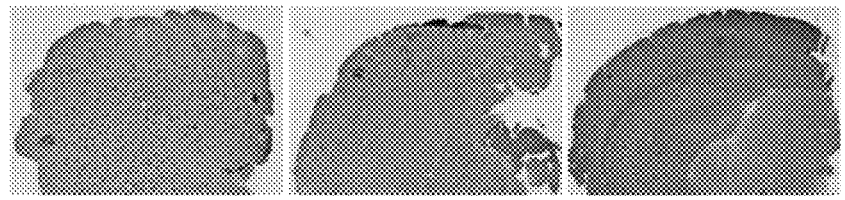
Figure 16D:
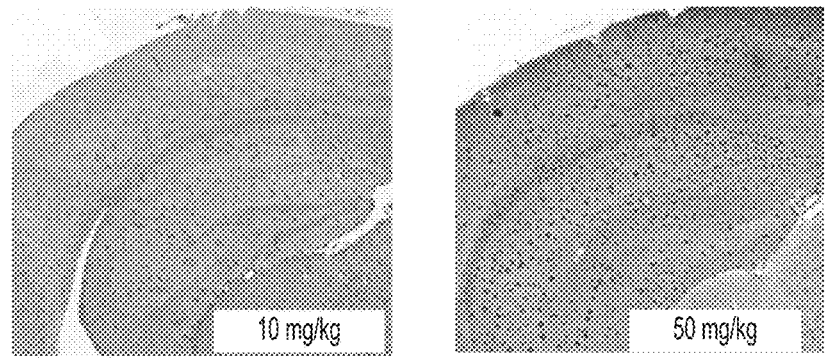

A 50-mg/kg dose of R3VQ-S-AF488 was injected in the tail vein of one mouse. The conjugate extravasation and staining in the brain was recorded for 3.5 hours post injection using two-photon microscopy on brain window (z=from the surface up to 360 μm deep). FIG. 16A displays in vivo imaging reconstruction (Maximum Intensity Projection—MIP) of R3VQ-S-AF488 over time up to 30 min in the same region. Few seconds after iv injection, strong staining of arborescent vessels was observed and declined dramatically 20 min later with only few capillary vessels remaining stained. This suggested a short half-life of conjugated VHH in the circulation (10-20 min). Shortly after injection a green fluorescent "cloud" formed and spread in the parenchymal space, presenting similarities with the spherical diffusion observed following stereotaxic injection of R3VQ (see above). 30 min after iv injection, amyloid plaques began to be visualized. Vascular Aβ (CAA) was also observed. The absence of signal in the red channel demonstrated that the fluorescent signal was specific (data not shown) and not due to general autofluorescence. Further imaging showed that in vivo staining of Aβ deposition in plaques and vessels remained up to 3.5 hours after injection (FIG. 16B), suggesting a brain half-life of R3VQ-S-AF488 extending over several hours. Four hours after the intravenous injection of R3VQ-S-AF488, the brain was harvested and 5 μm-thick paraffin sections were prepared. IHC was then performed with anti-His mAb to confirm the diffusion and labeling of amyloid plaques by R3VQ-S-AF488. Immunostaining of amyloid plaques by R3VQ-S-AF488 was observed throughout the entire brain with an accompanying brown background which could correspond to the diffusion halo of the VHH (FIG. 16C). Additional experiments were performed with a lower dose of R3VQ-S-AF488 (10 mg/kg) and in vivo detection of Aβ deposition was observed but with decreased intensity. These results suggested that R3VQ brain penetration and its potency to label brain Aβ lesions were dose-dependent, which was confirmed by IHC (FIG. 16D).

Basic pI of VHH is a Key Factor for its Ability to Transmigrate Across the BBB

Maleimido-AF488 conjugated R3VE was also prepared, whose pI was around 7.5 (FIGS. 17A and B) (VHH R3VE was described above). A 10 mg/kg dose of R3VE-S-AF488 was intravenously injected in a PS2APP mouse. 45 minutes after injection, only cerebral amyloid angiopathy was observed without labeling of amyloid plaques (FIG. 17C). 4 hours after the intravenous injection of R3VE-S-AF488, the brain was harvested and 5 μm-thick paraffin sections were prepared. IHC was then performed with anti-His mAb to detect the presence of intrinsic R3VE-S-AF488 in the brain (FIG. 17D). Compared with the result obtained with R3VQ-S-AF488 using the same dose (see above and FIG. 16D), only a very limited labeling of amyloid plaques was observed throughout the entire brain, suggesting that the positive electric charges present on the surface of VHHs play a role for brain penetration of these antibodies across the BBB.

Control Experiments

Evaluation in Amyloid Free Mouse

R3VQ-S-AF488 was intravenously injected in a wild type, amyloid-free, C57BL/6 mouse. No specific in vivo staining in the brain parenchyma was observed using two-photon microscopy assay (data not shown).

Comparison with Conventional IgG Antibody

Injection of mAb 4G8-AF488 iv in a PS2APP mouse only allowed to detect CAA by two-photon imaging but not amyloid plaques indicating no significant extravasation of this standard anti-AB immunoglobulin (FIG. 18).

Assessment of Blood-Brain Barrier Integrity in Mice Used for Two Photon Imaging

BBB permeability of the PS2APP mice (2-year-old) used for two-photon experiments was tested using DOTAREM iv injection (0.2 ml Gd 500 mM). This MRI contrast agent is unable to cross the BBB with the exception of pathological conditions leading to local leakages of the barrier. This MRI exam, used also in human, shows an increase of signal in areas where the BBB is disrupted (V. M. Runge et al., American Journal of Roentgenology, 1994, 162, 431-435; M. A. Ibrahim et al., Investigative radiology, 1998, 33, 153-162). The absence of signal modification in the tested mice suggested the integrity of their BBB. Two other age-matched PS2APP mice were also MRI-assessed using the same method and no disruption of the BBB was observed (data not shown).

The invention claimed is:

1. An isolated variable domain of a camelid heavy-chain antibody (VHH) directed against the fibrillar form of amyloid β, characterized in that its amino acid sequence comprises, from the N-terminus to the C-terminus, the amino acid sequence SEQ ID NO:1 (corresponding to the CDR1), the amino acid sequence SEQ ID NO:2 (corresponding to the CDR2) and the amino acid sequence SEQ ID NO:3 (corresponding to the CDR3).

2. The VHH according to claim 1, characterized in that it comprises an amino acid sequence selected from the group consisting of: SEQ ID NO:4, SEQ ID NO:5, SEQ ID NO:6, and SEQ ID NO:7.

3. A VHH derivative consisting of a polypeptide comprising the VHH of claim 1, provided that said VHH comprised in said polypeptide is able to bind the fibrillar form of amyloid β.

4. A VHH derivative characterized in that it has the amino acid sequence SEQ ID NO:8.

5. An isolated polynucleotide encoding the VHH of claim 1.

6. A recombinant expression cassette comprising the polynucleotide of claim 5 under the control of a transcriptional promoter allowing the regulation of the transcription of said polynucleotide in a host cell.

7. A recombinant vector comprising the polynucleotide of claim 5.

8. A host cell containing the recombinant expression cassette of claim 6.

9. A host cell containing the recombinant vector of claim 7.

10. A composition comprising the VHH of claim 1 linked to a substance of interest.

11. The composition of claim 10, wherein the substance of interest is selected from a peptide, an enzyme, a nucleic acid, a virus and a chemical entity.

12. The composition of claim 11, wherein the substance of interest is a NMR or MRI contrast agent selected from paramagnetic agents gadolinium (Gd), dysprosium (Dy) and manganese (Mn), and the superparamagnetic agents based on iron oxide or iron platinium, and the X-nuclei $^{18}$F, $^{13}$C, $^{23}$Na, $^{17}$O, and $^{15}$N.

13. The composition of claim 10, wherein the substance of interest is selected from the group consisting of an enzyme, a fluorophore, a NMR or MRI contrast agent, a radioisotope, or a nanoparticle.

14. The composition of claim 10, wherein the substance of interest is selected from the group consisting of an analgesic compound, an anti-inflammatory compound, an antidepressant compound, a cytotoxic compound, an anti-convulsant compound or an anti-neurodegenerative compound.

15. The composition of claim 10, wherein the substance of interest is a liposome or a polymeric entity.

16. A pharmaceutical composition comprising the composition of claim 10 and a pharmaceutically acceptable carrier.

17. A kit for brain imaging, or for diagnosing or monitoring a disorder mediated by amyloid β deposits comprising a VHH of claim 1 and a diagnostic agent.

18. An in vitro or ex vivo method for diagnosing a disorder mediated by amyloid β deposits in a subject, comprising the steps of:
   a) contacting in vitro a biological sample from said subject with the composition of claim 13, and
   b) determining the presence or the absence of amyloid β deposits in said biological sample,
   the presence of said amyloid β deposits indicating that said subject has a disorder mediated by amyloid β deposits.

19. An in vitro or ex vivo method for monitoring the progression or regression of a disorder mediated by amyloid β deposits in a subject, comprising the steps of:
   a) contacting in vitro a biological sample from said subject with the composition of claim 13,
   b) determining the amount of fibrillar form of amyloid β in said biological sample, and
   c) comparing the amount determined in step (b) with the amount of fibrillar form of amyloid β previously obtained for said subject,
   wherein a significant increase in amount of fibrillar form of amyloid β constitutes a marker of the progression of said disorder mediated by amyloid β deposits and a significant decrease of fibrillar form of amyloid β constitutes a marker of the regression of said disorder mediated by amyloid β deposits.

20. A method for in vivo imaging amyloid β deposits in a subject comprising the steps of
   a) administrating a detectable quantity of the composition of claim 13 to a subject, and,
   b) detecting the substance of interest in said subject by an imaging method.

21. An in vitro or ex vivo method for detecting the presence or the absence of amyloid β deposits in a subject, comprising the steps of:
   a) contacting in vitro a biological sample from said subject with the composition of claim 13, and
   b) determining the presence or the absence of amyloid β deposits in said biological sample.

22. A non-site specific method for coupling a VHH of claim 1 with a substance of interest, said method comprising a conjugation step of a substance of interest with the VHH.

23. The non-site specific method of claim 22, wherein the substance of interest is a compound selected from the group consisting of a peptide, an enzyme, a nucleic acid, a virus, a fluorophore, a NMR or MRI contrast agent, a chemical entity, a radioisotope and a nanoparticle.

24. The non-site specific method of claim 23, wherein the substance of interest is a compound selected from NMR or MRI contrast agents and metallic radioisotopes.

25. The non-site specific method of claim 24 comprising the following steps:
   (i) the conjugation of a chelating agent activated in the form of an ester or an anhydride with lysine residues of a VHH directed against the fibrillar form of amyloid β, characterized in that its amino acid sequence comprises, from the N-terminus to the C-terminus, the amino acid sequence SEQ ID NO:1 (corresponding to the CDR1), the amino acid sequence SEQ ID NO:2 (corresponding to the CDR2) and the amino acid sequence SEQ ID NO:3 (corresponding to the CDR3), and
   (ii) the chelation of the ligand of step (i) with the substance of interest.

26. The non-site specific method of claim 25, wherein the substance of interest is a NMR or MRI contrast agent selected from the paramagnetic agents gadolinium (Gd), dysprosium (Dy) and manganese (Mn), and the superparamagnetic agents based on iron oxide or iron platinium, and the X-nuclei $^{18}$F, $^{13}$C, $^{23}$Na, $^{17}$O, and $^{15}$N.

27. The non-site specific method of claim 25, wherein the chelating agent is selected from 1,4,7,10-tetraazacyclododecane-1,4,7,10-tetracetic acid (DOTA), diethylene triamine penta-acetic acid (DTPA), 1,4,7-tris(carboxymethylaza)cyclododecane-10-azaacetylamide (DO3A), nitrilotriacetic acid (NTA), D-penicillamine (Pen), 2,3-dimercaptosuccinic acid (DMSA), 2,3-dimercapto-1-propanesulfonic acid (DMPS), 2,3-dimercaptopropanol (BAL), triethylenetramine (Trien), the ammonium tetrathiomolybdate (TTM) anion, ethylenediaminetetraacetic acid (EDTA), 2-(p-isothiocyanatobenzyl)-6-methyl-diethylenetriaminepentaacetic acid (IB4M) or hydroxypyridinone (HOPO).

28. The non-site specific method of claim 25, wherein the substance of interest is gadolinium (Gd), and the chelating agent is DOTA.

29. The non-site specific method of claim 24 comprising the following steps:
   (i') the chelation of a substance of interest with a chelating agent activated in the form of an ester or an anhydride and
   (ii') the conjugation of the pre-chelated substance of interest of step (i') with lysine residues of a VHH directed against the fibrillar form of amyloid β, characterized in that its amino acid sequence comprises, from the N-terminus to the C-terminus, the amino acid sequence SEQ ID NO:1 (corresponding to the CDR1), the amino acid sequence SEQ ID NO:2 (corresponding to the CDR2) and the amino acid sequence SEQ ID NO:3 (corresponding to the CDR3).

30. The non-site specific method of claim 29, wherein the substance of interest is a NMR or MRI contrast agent selected from the paramagnetic agents gadolinium (Gd), dysprosium (Dy) and manganese (Mn), and the superparamagnetic agents based on iron oxide or iron platinium, and the X-nuclei $^{18}$F, $^{13}$C, $^{23}$Na, $^{17}$O, and $^{15}$N.

31. The non-site specific method of claim 29, wherein the chelating agent is selected from 1,4,7,10-tetraazacyclododecane-1,4,7,10-tetracetic acid (DOTA), diethylene triamine penta-acetic acid (DTPA), 1,4,7-tris(carboxymethylaza)cyclododecane-10-azaacetylamide (DO3A), nitrilotriacetic acid (NTA), D-penicillamine (Pen), 2,3-dimercaptosuccinic acid (DMSA), 2,3-dimercapto-1-propanesulfonic acid (DMPS), 2,3-dimercaptopropanol (BAL), triethylenetramine (Trien), the ammonium tetrathiomolybdate (TTM) anion, ethylenediaminetetraacetic acid (EDTA), 2-(p-isothiocyanatobenzyl)-6-methyl-diethylenetriaminepentaacetic acid (IB4M) or hydroxypyridinone (HOPO).

32. The non-site specific method of claim 29, wherein the substance of interest is gadolinium (Gd), and the chelating agent is DOTA.

* * * * *

SEQUENCE LISTING

```
<160> NUMBER OF SEQ ID NOS: 17

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      CDR1 of VHH R3VE/Q peptide

<400> SEQUENCE: 1

Ala Asp Ser Gly Ser Thr Phe Arg Asn Tyr Asn Ile Gly
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR2 of VHH R3VE/Q peptide

<400> SEQUENCE: 2

Ala Val Ser Arg Thr Gly Ile Ser Thr His Val Ala Asp Ser Leu Gln
1               5                   10                  15

Gly

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      CDR3 of VHH R3VE/Q peptide

<400> SEQUENCE: 3
```

```
Ala Ala Gly Arg Pro Gly Val Gly Ala Val Asn Arg Ala Met Asp Tyr
1               5                   10                  15

Asp Tyr

<210> SEQ ID NO 4
<211> LENGTH: 127
<212> TYPE: PRT
<213> ORGANISM: Lama pacos

<400> SEQUENCE: 4

Met Ala Glu Val Gln Leu Gln Ala Ser Gly Gly Gly Leu Val Gln Thr
1               5                   10                  15

Gly Asp Ser Leu Arg Leu Ser Cys Ala Asp Ser Gly Ser Thr Phe Arg
                20                  25                  30

Asn Tyr Asn Ile Gly Trp Phe Arg Gln Thr Pro Gly Gln Ala Arg Glu
            35                  40                  45

Phe Val Ala Ala Val Ser Arg Thr Gly Ile Ser Thr His Val Ala Asp
        50                  55                  60

Ser Leu Gln Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Val Tyr
                85                  90                  95

Ser Cys Ala Ala Gly Arg Pro Gly Val Gly Ala Val Asn Arg Ala Met
            100                 105                 110

Asp Tyr Asp Tyr Trp Gly Gln Gly Thr Gln Val Thr Val Ser Ser
        115                 120                 125

<210> SEQ ID NO 5
<211> LENGTH: 127
<212> TYPE: PRT
<213> ORGANISM: Lama pacos

<400> SEQUENCE: 5

Met Ala Glu Val Gln Leu Glu Ala Ser Gly Gly Gly Leu Val Gln Thr
1               5                   10                  15

Gly Asp Ser Leu Arg Leu Ser Cys Ala Asp Ser Gly Ser Thr Phe Arg
                20                  25                  30

Asn Tyr Asn Ile Gly Trp Phe Arg Gln Thr Pro Gly Gln Ala Arg Glu
            35                  40                  45

Phe Val Ala Ala Val Ser Arg Thr Gly Ile Ser Thr His Val Ala Asp
        50                  55                  60

Ser Leu Gln Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Val Tyr
                85                  90                  95

Ser Cys Ala Ala Gly Arg Pro Gly Val Gly Ala Val Asn Arg Ala Met
            100                 105                 110

Asp Tyr Asp Tyr Trp Gly Gln Gly Thr Gln Val Thr Val Ser Ser
        115                 120                 125

<210> SEQ ID NO 6
<211> LENGTH: 122
<212> TYPE: PRT
<213> ORGANISM: Lama pacos

<400> SEQUENCE: 6

Val Gln Leu Gln Ala Ser Gly Gly Gly Leu Val Gln Thr Gly Asp Ser
1               5                   10                  15
```

```
Leu Arg Leu Ser Cys Ala Asp Ser Gly Ser Thr Phe Arg Asn Tyr Asn
            20                  25                  30

Ile Gly Trp Phe Arg Gln Thr Pro Gly Gln Ala Arg Glu Phe Val Ala
        35                  40                  45

Ala Val Ser Arg Thr Gly Ile Ser Thr His Val Ala Asp Ser Leu Gln
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Ser Cys Ala
                85                  90                  95

Ala Gly Arg Pro Gly Val Gly Ala Val Asn Arg Ala Met Asp Tyr Asp
            100                 105                 110

Tyr Trp Gly Gln Gly Thr Gln Val Thr Val
            115                 120

<210> SEQ ID NO 7
<211> LENGTH: 122
<212> TYPE: PRT
<213> ORGANISM: Lama pacos

<400> SEQUENCE: 7

Val Gln Leu Glu Ala Ser Gly Gly Gly Leu Val Gln Thr Gly Asp Ser
1               5                   10                  15

Leu Arg Leu Ser Cys Ala Asp Ser Gly Ser Thr Phe Arg Asn Tyr Asn
            20                  25                  30

Ile Gly Trp Phe Arg Gln Thr Pro Gly Gln Ala Arg Glu Phe Val Ala
        35                  40                  45

Ala Val Ser Arg Thr Gly Ile Ser Thr His Val Ala Asp Ser Leu Gln
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Ser Cys Ala
                85                  90                  95

Ala Gly Arg Pro Gly Val Gly Ala Val Asn Arg Ala Met Asp Tyr Asp
            100                 105                 110

Tyr Trp Gly Gln Gly Thr Gln Val Thr Val
            115                 120

<210> SEQ ID NO 8
<211> LENGTH: 151
<212> TYPE: PRT
<213> ORGANISM: Artificial Sequence
<220> FEATURE:
<223> OTHER INFORMATION: Description of Artificial Sequence: Synthetic
      R3VQ-SH polypeptide
<220> FEATURE:
<221> NAME/KEY: DOMAIN
<222> LOCATION: (5)..(6)
<223> OTHER INFORMATION: 6xHis tag
<220> FEATURE:
<221> NAME/KEY: DOMAIN
<222> LOCATION: (14)..(19)
<223> OTHER INFORMATION: Thrombin cleavage site
<220> FEATURE:
<221> NAME/KEY: DOMAIN
<222> LOCATION: (23)..(144)
<223> OTHER INFORMATION: VHH R3VQ
<220> FEATURE:
<221> NAME/KEY: DOMAIN
<222> LOCATION: (145)..(148)
<223> OTHER INFORMATION: Spacer
<220> FEATURE:
```

```
<221> NAME/KEY: DOMAIN
<222> LOCATION: (150)..(151)
<223> OTHER INFORMATION: Spacer

<400> SEQUENCE: 8

Met Gly Ser Ser His His His His His His Ser Ser Gly Leu Val Pro
1               5                   10                  15

Arg Gly Ser Ala Ala Ala Val Gln Leu Gln Ala Ser Gly Gly Gly Leu
            20                  25                  30

Val Gln Thr Gly Asp Ser Leu Arg Leu Ser Cys Ala Asp Ser Gly Ser
        35                  40                  45

Thr Phe Arg Asn Tyr Asn Ile Gly Trp Phe Arg Gln Thr Pro Gly Gln
    50                  55                  60

Ala Arg Glu Phe Val Ala Ala Val Ser Arg Thr Gly Ile Ser Thr His
65              70                  75                  80

Val Ala Asp Ser Leu Gln Gly Arg Phe Thr Ile Ser Arg Asp Asn Ala
            85                  90                  95

Lys Asn Thr Val Tyr Leu Gln Met Asn Ser Leu Lys Pro Glu Asp Thr
            100                 105                 110

Ala Val Tyr Ser Cys Ala Ala Gly Arg Pro Gly Val Gly Ala Val Asn
        115                 120                 125

Arg Ala Met Asp Tyr Asp Tyr Trp Gly Gln Gly Thr Gln Val Thr Val
    130                 135                 140

Gly Gly Gly Ser Cys Ser Ala
145                 150

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      thrombin cleavage site peptide

<400> SEQUENCE: 10

Leu Val Pro Arg Gly Ser
1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      spacer peptide

<400> SEQUENCE: 11

Gly Gly Gly Ser
1
```

<210> SEQ ID NO 12
<211> LENGTH: 42
<212> TYPE: PRT
<213> ORGANISM: Artificial Sequence
<220> FEATURE:
<223> OTHER INFORMATION: Description of Artificial Sequence: Synthetic amyloid beta 42 polypeptide

<400> SEQUENCE: 12

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ggactagttg cggccgctgg ttgtggtttt ggtgtcttgg g                                   41

<210> SEQ ID NO 14
<211> LENGTH: 123
<212> TYPE: PRT
<213> ORGANISM: Lama pacos

<400> SEQUENCE: 14

```
Met Ala Glu Val Gln Leu Gln Ala Ser Gly Gly Gly Leu Val Gln Ala
1               5                   10                  15

Gly Gly Ser Arg Arg Leu Ser Cys Ala Val Ser Gly Arg Thr Phe Ser
            20                  25                  30

Ser Tyr Asn Met Gly Trp Phe Arg Gln Ala Pro Gly Glu Glu Arg Glu
        35                  40                  45

Phe Val Ala Ala Ile Asn Trp Ser Ala Ser Thr Tyr Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Asn Leu His Val Ala Thr Thr Ser Tyr Phe Gln Thr Ser Asp Tyr
            100                 105                 110

Trp Gly Gln Gly Thr Gln Val Thr Val Ser Ser
        115                 120
```

<210> SEQ ID NO 15
<211> LENGTH: 123
<212> TYPE: PRT
<213> ORGANISM: Lama pacos

<400> SEQUENCE: 15

```
Met Ala Glu Val Gln Leu Gln Ala Ser Gly Gly Gly Leu Val Gln Ala
1               5                   10                  15

Gly Gly Ser Leu Arg Leu Ser Cys Ala Val Ser Gly Arg Thr Phe Ser
            20                  25                  30

Ser Tyr Asn Met Gly Trp Phe Arg Gln Ala Pro Gly Lys Glu Arg Glu
```

```
                35                  40                  45
Phe Val Ala Ala Ile Asn Trp Ser Ala Ser Thr Tyr Tyr Ala Asp Ser
         50                  55                  60
Val Lys Gly Arg Phe Thr Ile Ser Arg Asp Asn Ala Lys Asn Thr Val
 65                  70                  75                  80
Tyr Leu Gln Met Asn Ser Leu Lys Pro Glu Asp Thr Ala Val Tyr Tyr
                 85                  90                  95
Cys Asn Leu His Val Ala Thr Thr Ser Tyr Phe Gln Thr Ser Asp Tyr
            100                 105                 110
Trp Gly Gln Gly Thr Gln Val Thr Val Ser Ser
        115                 120

<210> SEQ ID NO 16
<211> LENGTH: 124
<212> TYPE: PRT
<213> ORGANISM: Lama pacos

<400> SEQUENCE: 16

Met Ala Asp Val Gln Leu Gln Ala Ser Gly Gly Gly Leu Val Gln Pro
 1               5                  10                  15
Gly Gly Ser Leu Glu Leu Ser Cys Ala Ala Ser Gly Ser Thr Phe Ser
             20                  25                  30
Ile Asn Val Met Gly Trp Tyr Arg Gln Ser Pro Asp Gly Val Arg Asp
         35                  40                  45
Leu Val Ala Thr Ile Thr Ala Asn Gly Val Thr Asn Tyr Ala Ala Ser
     50                  55                  60
Val Lys Gly Arg Phe Thr Ile Ser Lys Asp Asn Ala Lys Asn Thr Val
 65                  70                  75                  80
Phe Leu Gln Met Asn Ser Val Lys Pro Glu Asp Thr Ala Val Tyr Ile
                 85                  90                  95
Cys Asn Val Glu Gly Glu Tyr Ser Gly Ser Tyr Val Ala Asp Phe Asp
            100                 105                 110
Ser Trp Gly Gln Gly Thr Gln Val Thr Val Ser Ser
        115                 120

<210> SEQ ID NO 17
<211> LENGTH: 465
<212> TYPE: DNA
<213> ORGANISM: Artificial Sequence
<220> FEATURE:
<223> OTHER INFORMATION: Description of Artificial Sequence: Synthetic
      polynucleotide encoding R3VQ-SH

<400> SEQUENCE: 17
atgggcagca gccatcatca tcatcatcac agcagcggcc tggtgccgcg cggcagcgcg      60
gccgcagtcc agctgcaggc gtctggagga ggattggtgc agactgggga ctctctgaga     120
ctctcctgtg cagactctgg aagtacattc agaaactata acataggctg gttccgccag     180
actccaggac aggcgcgtga atttgtcgca gctgttagtc ggacgggaat tagcacacac     240
gttgcagact ccctccaggg ccgattcacc atctccagag acaacgccaa gaacacggtg     300
tatctgcaaa tgaacagcct gaaacctgag gacacggccg tttattcctg tgcagcgggg     360
cgaccgggcg taggagctgt caacagggcg atggattatg actactgggg ccaggggacc     420
caggtcaccg tcggtggcgg atcctgttcc gcgtaataac tcgag                     465
```